United States Patent [19]

Barnish et al.

[11] Patent Number: 5,030,654

[45] Date of Patent: Jul. 9, 1991

[54] GLUTARAMIDE DIURETIC AGENTS

[75] Inventors: Ian T. Barnish, Ramsgate; John C. Danilewicz, Ash; Keith James, Great Mongeham; Gillian M. R. Samuels, Barham; Nicholas K. Terrett, Worth; Michael T. Williams, Deal; Martin J. Wythes, Sutton, all of United Kingdom

[73] Assignee: Pfizer Inc., New York, N.Y.

[21] Appl. No.: 354,170

[22] Filed: May 19, 1989

Related U.S. Application Data

[63] Continuation-in-part of Ser. No. 131,157, Dec. 10, 1987, abandoned.

[30] Foreign Application Priority Data

Dec. 11, 1986 [GB] United Kingdom ................ 8629663
Jul. 3, 1987 [GB] United Kingdom ................ 8715722

[51] Int. Cl.$^5$ ............................................. A61K 31/21
[52] U.S. Cl. ............................... 514/510; 514/237.5; 514/255; 514/259; 514/269; 514/311; 514/319; 514/331; 514/365; 514/381; 514/396; 514/406; 514/408; 514/427; 514/438; 514/450; 514/471; 514/529; 514/530; 514/533; 544/159; 544/163; 544/165; 544/225; 544/283; 544/335; 544/336; 544/391; 544/400; 544/406; 546/168; 546/172; 546/175; 546/205; 546/226; 546/233; 546/336; 548/200; 548/204; 548/236; 548/247; 548/248; 548/252; 548/342; 548/352; 548/356; 548/482; 548/486; 548/491; 548/537; 548/561; 548/568; 549/72; 549/347; 549/426; 549/493; 560/41; 560/106; 560/107; 560/119; 560/122; 560/125; 562/450; 562/501; 562/504; 562/507

[58] Field of Search .............. 560/41, 119, 122, 125, 560/106, 107; 562/450, 501, 504, 507; 546/205, 226, 233, 336, 168, 172, 175; 544/225, 335, 283, 391, 400, 406, 336, 159, 163, 165; 548/200, 204, 236, 247, 248, 252, 341, 342, 352, 356, 482, 486, 491, 537, 561, 568; 549/72, 347, 426, 493; 514/234, 255, 259, 269, 311, 319, 331, 365, 381, 396, 406, 427, 408, 438, 450, 471, 510, 530, 533, 529

[56] References Cited

U.S. PATENT DOCUMENTS

4,513,009 4/1985 Roques et al. ...................... 514/513
4,749,688 6/1988 Haslanger et al. .................... 514/19

FOREIGN PATENT DOCUMENTS

0225292 6/1987 European Pat. Off. .
WO86/00066 1/1986 PCT Int'l Appl. .
2167748 6/1986 United Kingdom .

Primary Examiner—Michael L. Shippen
Attorney, Agent, or Firm—Peter C. Richardson; Paul H. Ginsburg

[57] ABSTRACT

A series of novel spiro-substituted glutaramide derivatives have been prepared, including the pharmaceutically acceptable salts thereof and bioprecursors therefor, wherein the spiro-substituent completes a 5- or 6-membered carbocyclic ring and is located at the carbon atom adjacent to the carbamoyl group. These particular compounds are inhibitors of the neutral endopeptidase E.C.3.4.24.11 enzyme and are therefore useful in therapy as diuretic agents for the treatment of hypertension, heart failure, renal insufficiency and other disorders. Methods for preparing these compounds from known starting materials are provided.

38 Claims, No Drawings

GLUTARAMIDE DIURETIC AGENTS

CROSS REFERENCE TO RELATED APPLICATION

This application is a continuation-in-part of co-pending Ser. No. 07/131,157, filed Dec. 10, 1987, now abandoned.

BACKGROUND OF THE INVENTION

This invention relates to a series of spiro-substituted glutaramide derivatives which are diuretic agents having utility in a variety of therapeutic areas including the treatment of various cardiovascular disorders such as hypertension and heart failure.

The compounds are inhibitors of the zinc-dependent, neutral endopeptidase E.C.3.4.24.11. This enzyme is involved in the breakdown of several peptide hormones, including atrial natriuretic factor (ANF), which is secreted by the heart and which has potent vasodilatory and diuretic/natriuretic activity. Thus, the compounds of the invention, by inhibiting the neutral endopeptidase E.C.3.4.24.11, can potentiate the biological effects of ANF. Thus, in particular the compounds are diuretic agents having utility in the treatment of a number of disorders, including hypertension, heart failure, renal insufficiency, premenstrual syndrome, cyclical oedema, Menieres disease and hypercalciuria. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of asthma, inflammation, pain, epilepsy, affective disorders, dementia and geriatric confusion, obesity and gastrointestinal disorders (especially diarrhoea and irritable bowel syndrome), the modulation of gastric acid secretion and the treatment of hyperreninaemia.

SUMMARY OF THE INVENTION

The compounds are of the formula:

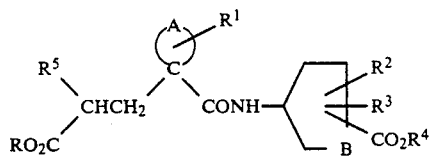

(I)

wherein

A completes a 5 or 6 membered carbocyclic ring which may be saturated or mono-unsaturated and which may optionally be fused to a further saturated or unsaturated 5 or 6 membered carbocyclic ring;

B is $(CH_2)_m$ wherein m is an integer of from 1 to 3;

each of R and $R^4$ is independently H, $C_1$-$C_6$ alkyl, benzyl or an alternative biolabile ester-forming group;

$R^1$ is H or $C_1$-$C_4$ alkyl;

$R^2$ and $R^3$ are each independently H, OH, $C_1$-$C_4$ alkyl or $C_1$-$C_4$ alkoxy; and $R^5$ is $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ alkoxy, $-NR^6R^7$, $-NR^8COR^9$, $-NR^8SO_2R^9$ or a saturated heterocyclic group; or $C_1$-$C_6$ alkyl substituted by one or more substituents chosen from halo, hydroxy, $C_1$-$C_6$ alkoxy, $C_2$-$C_6$ hydroxyalkoxy, $C_1$-$C_6$ alkoxy($C_1$-$C_6$ alkoxy), $C_3$-$C_7$ cycloalkyl, $C_3$-$C_7$ cycloalkenyl, aryl, aryloxy, aryloxy($C_1$-$C_4$ alkoxy), heterocyclyl, heterocyclyloxy, $-NR^6R^7$, $-NR^8COR^9$, $-NR^8SO_2R^9$, $-CONR^6R^7$, $-SH$, $-S(O)_pR^{10}$, $-COR^{11}$ or $-CO_2R^{12}$; wherein $R^6$ and $R^7$ are each independently H, $C_1$-$C_4$ alkyl, $C_3$-$C_7$ cycloalkyl (optionally substituted by hydroxy or $C_1$-$C_4$ alkoxy), aryl, aryl($C_1$-$C_4$ alkyl), $C_2$-$C_6$ alkoxyalkyl, or heterocyclyl; or the two groups $R^6$ and $R^7$ are taken together with the nitrogen to which they are attached to form a pyrrolidinyl, piperidino, morpholino, piperazinyl or N-($C_1$-$C_4$ alkyl)-piperazinyl group;

$R^8$ is H or $C_1$-$C_4$ alkyl;

$R^9$ is $C_1$-$C_4$ alkyl, $CF_3$, aryl, aryl($C_1$-$C_4$ alkyl), aryl($C_1$-$C_4$ alkoxy), heterocycyl, $C_1$-$C_4$ alkoxy or $NR^6R^7$ wherein $R^6$ and $R^7$ are as previously defined;

$R^{10}$ is $C_1$-$C_4$ alkyl, aryl, heterocyclyl or $NR^6R^7$ wherein $R^6$ and $R^7$ are as previously defined;

$R^{11}$ is $C_1$-$C_4$ alkyl, $C_3$-$C_7$ cycloalkyl, aryl or heterocyclyl;

$R^{12}$ is H or $C_1$-$C_4$ alkyl; and p is 0, 1 or 2;

and pharmaceutically acceptable salts thereof and bioprecursors therefor.

In the above definition, unless otherwise indicated, alkyl groups having three or more carbon atoms may be straight or branched-chain. The term aryl as used herein means an aromatic hydrocarbon group such as phenyl or naphthyl which may optionally be substituted with, for example, one or more OH, CN, $CF_3$, $C_1$-$C_4$ alkyl, $C_1$-$C_4$ alkoxy, halo, carbamoyl, amino, mono or di($C_1$-$C_4$ alkyl) amino or ($C_1$-$C_4$ alkanoyl)amino groups. Halo means fluoro, chloro, bromo or iodo.

The term heterocyclyl means a 5 or 6 membered nitrogen, oxygen or sulphur containing heterocyclic group which, unless otherwise stated, may be saturated or unsaturated and which may optionally include a further oxygen or one to three nitrogen atoms in the ring and which may optionally be benzofused or substituted with for example, one or more halo, $C_1$-$C_4$ alkyl, hydroxy, carbamoyl, benzyl, oxo, amino or mono or di-($C_1$-$C_4$ alkyl)amino or ($C_1$-$C_4$ alkanoyl)amino groups. Particular examples of heterocycles include pyridyl, pyrazinyl, pyrimidinyl, pyridazinyl, pyrrolyl, imidazolyl, pyrazolyl, triazolyl, tetrazolyl, furanyl, tetrahydrofuranyl, tetrahydropyranyl, dioxanyl, thienyl, oxazolyl, isoxazolyl, thiazolyl, isoindolinyl, quinolyl, quinoxalinyl, quinazolinyl and benzimidazolyl, each being optionally substituted as previously defined.

The compounds of formula (I) may contain several asymmetric centres and thus they can exist as enantiomers and diastereomers. The invention includes both the separated individual isomers as well as mixtures of isomers.

The pharmaceutically acceptable salts of the compounds of formula (I) containing an acidic centre are those formed with bases which form non-toxic salts. Examples include the alkali metal salts such as the sodium, potassium or calcium salts or salts with amines such as diethylamine. Compounds having a basic centre can also form acid addition salts with pharmaceutically acceptable acids. Examples include the hydrochloride hydrobromide, sulphate or bisulphate, phosphate or acid phosphate, acetate, citrate, fumarate, gluconate, lactate, maleate, succinate and tartrate salts.

The term bioprecursor in the above definition means a pharmaceutically acceptable biologically degradable derivative of the compound of formula (I) which, upon administration to an animal or human being, is converted in the patient's body to produce a compound of the formula (I).

One group of preferred compounds of formula (I) are those compounds wherein A is $(CH_2)_n$ and n is an integer of from 2 to 6 and wherein each of R and $R^4$ is independently H, $C_1$–$C_6$ alkyl or benzyl.

A particularly preferred group of compounds of the formula (I) are those wherein A is $(CH_2)_4$, $R^1$ is H and B is $(CH_2)_2$, i.e. compounds of the formula (II) wherein $R^2$, $R^3$, $R^4$ and $R^5$ are as previously defined for formula (I):

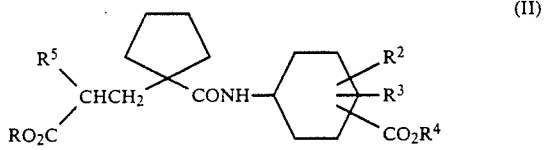

(II)

Also preferred are those compounds of formulae (I) and (II) wherein R and $R^4$ are both H (diacids) as well as biolabile mono and di-ester derivatives thereof wherein one or both of R and $R^4$ is a biolabile ester-forming group.

The term biolabile ester-forming group is well understood in the art as meaning a group which provides an ester which can be readily cleaved in the body to liberate the corresponding diacid of formula (I) wherein R and $R^4$ are both H. A number of such ester groups are well known, for example in the penicillin area or in the case of the ACE-inhibitor antihypertensive agents.

In the case of the compounds of formulae (I) and (II) such biolabile pro-drug esters are particularly advantageous in providing compounds of the formula (I) suitable for oral administration. The suitability of any particular ester-forming group can be assessed by conventional animal or in vitro enzyme hydrolysis studies. Thus, desirably for optimum effect, the ester should only be hydrolysed after absorption, accordingly, the ester should be resistant to hydrolysis before absorption by digestive enzymes but should be readily hydrolyzed by for example, liver enzymes. In this way the active diacid is released into the bloodstream following oral absorption.

In addition to lower alkyl esters (particularly ethyl) and benzyl esters, suitable biolabile esters include alkanoyloxymethyl esters, including alkyl, cycloalkyl and aryl substituted derivatives thereof, aroyloxyalkyl ester, arylesters, aralkylesters, and haloalkyl esters wherein said alkanoyl or alkyl groups have from 1 to 8 carbon atoms and are branched or straight chain and said aryl groups are phenyl, naphthyl or indanyl optionally substituted with one or more $C_1$–$C_4$ alkyl or $C_1$–$C_4$ alkoxy groups or halo atoms.

Thus examples of R and $R^4$ when they are biolabile ester-forming groups other than ethyl and benzyl include:
1-(2,2-diethylbutyryloxy)ethyl
2-ethylpropionyloxymethyl
1-(2-ethylpropionyloxy)ethyl
1-(2,4-dimethylbenzoyloxy)ethyl
α-benzoyloxybenzyl
1-(benzoyloxy)ethyl
2-methyl-1-propionyloxy-1-propyl
2,4,6-trimethylbenzoyloxymethyl
1-(2,4,6-trimethylbenzoyloxy)ethyl
pivaloyloxymethyl
phenethyl
phenpropyl
2,2,2-trifluoroethyl
1- or 2-naphthyl
2,4-dimethylphenyl
4-t-butylphenyl and
5-indanyl.

Of these a particularly preferred biolabile ester-forming group is 5-indanyl.

Compounds of the formulae (I) and (II) wherein one or both of R and $R^4$ are $C_1$–$C_6$ alkyl, particularly ethyl, or benzyl, are also active by virtue of their hydrolysis in vivo, and, in addition, are valuable intermediates for the preparation of the diacids wherein R and $R^4$ are both H. The mono-benzyl and mono-ethyl esters in particular have been found to be rapidly hydrolysed in vivo to give the diacid.

In a further group of preferred compounds of formula (II), R is H, $R^2$ is H, $R^3$ is $CH_3$ or $C_2H_5$ and $R^4$ is H. Particularly preferred are those compounds wherein the carboxy group is attached at the 3- or 4-position of the cyclohexane ring, most especially those compounds having cis-stereochemistry relative to the amide group.

Of particular interest because of their good oral activity are the mono-ethyl esters of formula (II) wherein R is H and $R^4$ is ethyl, $R^2$ is H, $R^3$ is H, $CH_3$ or $C_2H_5$ and wherein the ester group is attached at the 3-position of the cyclohexane ring and has cis-stereochemistry relative to the amide group.

The group $R^5$ is preferably $C_2$–$C_4$ alkyl, $C_2$–$C_4$ alkenyl, $C_2$–$C_5$ alkynyl, $C_5$–$C_6$ cycloalkyl, $C_5$–$C_6$ cycloalkenyl, $C_1$–$C_4$ alkylsulphonamido, or tetrahydrofuranyl or wherein $R^5$ is $C_1$–$C_3$ alkyl substituted by $C_1$–$C_3$ alkoxy, $C_1$–$C_6$ alkoxy($C_2$–$C_4$ alkoxy), $C_3$–$C_6$ cycloalkyl, 4-pyridyl, 2-imidazolyl, $C_2$–$C_4$ alkanoyl, $C_2$–$C_4$ alkoxycarbonylamino, $C_1$–$C_4$ alkylsulphonyl, $C_1$–$C_4$ alkylsulphonamido, benzenesulphonamido or benzoylamino.

Thus in one particular and preferred aspect, the invention provides dicarboxylic acids of the formula (II) wherein R and $R^4$ are both H, and wherein $R^2$ and $R^3$ are both H, the group $CO_2R^4$ is attached at the 4-position of the cyclohexane ring and has cis-stereochemistry relative to the amide group and wherein $R^5$ is n-propyl, methoxyethyl, 2-methoxyethoxymethyl, 2-butynyl, cyclohexenyl, tetrahydrofuranyl, 4-pyridylmethyl, 2-imidazolylmethyl, acetonyl, ethylsulphonylmethyl, benzenesulphonamidomethyl, n-propylsulphonamido or 1-methoxycarbonylaminoethyl.

Particularly preferred individual compounds include
3-{1-[(cis-4-carboxycyclohexyl)carbamoyl]cyclopentyl}-2-(n-propyl)propanoic acid.

3-{1-[(cis-4-carboxycyclohexyl)carbamoyl]cyclopentyl}2-(2-methoxyethyl)propanoic acid.

3-{1-[(cis-4-carboxycyclohexyl)carbamoyl]cyclopentyl}2-(2-methoxyethoxymethyl)propanoic acid.

3-{1-[(cis-4-carboxycyclohexyl)carbamoyl]cyclopentyl}2-(2-butynyl)propanoic acid.

3-{1-[(cis-4-carboxycyclohexyl)carbamoyl]cyclopentyl}2-(3-tetrahydrofuranyl)propanoic acid.

3-{1-[(cis-4-carboxycyclohexyl)carbamoyl]cyclopentyl}2-(n-propylsulphonamido)propanoic acid.

In another particular and preferred aspect, the invention provides dicarboxylic acids of the formula (II) wherein R and $R^4$ are both H, $R^2$ and $R^3$ are both H, the group $CO_2R^4$ is attached at the 3-position of the cyclohexane ring and has cis-stereochemistry relative to the amide group and wherein $R^5$ is n-propyl, 2-methoxyethoxymethyl, 2-butynyl, 2-propenyl, 2-butenyl, cyclopentyl, cyclohexyl, cyclohexenyl, cyclopropylmethyl, tetrahydrofuranyl, 4-pyridylmethyl, n-propylsulphonylamino, benzenesulphonylaminomethyl, or benzoylaminomethyl.

Particularly preferred individual compounds include
3-{1-[(cis-3-carboxycyclohexyl)carbamoyl]cyclopentyl}-2-(n-propyl)propanoic acid,
3-{1-[(cis-3-carboxycyclohexyl)carbamoyl]cyclopentyl}-2-(2-methoxyethoxymethyl)propanoic acid,
3-{1-[(cis-3-carboxycyclohexyl)carbamoyl]cyclopentyl}-2-(2-butynyl)propanoic acid, and
3-{1-[(cis-3-carboxycyclohexyl)carbamoyl]cyclopentyl}-2-(n-propylsulphonamido)propanoic acid.

In a further particular and preferred aspect, the invention provides mono ethyl esters of the formula (II) wherein R is H and $R^4$ is ethyl and wherein $R^2$ and $R^3$ are both H, the ethoxycarbonyl group is attached at the 3-position of the cyclohexane ring and has cis-stereochemistry and $R^5$ is 2-methoxyethoxymethyl, n-propyl, 2-butynyl, 2-propenyl, cyclohexenyl, cyclohexyl, cyclopentyl, cyclopropylmethyl, tetrahydrofuranyl, 4-pyridylmethyl, benzenesulphonamidomethyl, benzoylaminomethyl, or n-propylsulphonamido.

Particularly preferred individual compounds include
3-{1-[(cis-3-ethoxycarbonylcyclohexyl)carbamoyl]cyclopentyl}-2-(2-methoxyethoxymethyl)propanoic acid.
3-{1-[(cis-3-ethoxycarbonylcyclohexyl)carbamoyl]cyclopentyl}2-(n-propyl)propanoic acid,
3-{1-[(cis-3-ethoxycarbonylcyclohexyl)carbamoyl]cyclopentyl}2-(2-butynyl)propanoic acid, and
3-{1-[(cis-3-ethoxycarbonylcyclohexyl)carbamoyl]cyclopentyl}2-(n-propylsulphonamido)propanoic acid.

In a yet further particular and preferred aspect, the invention provides biolabile ester derivatives of formula (II) wherein one or both of R and $R^4$ is 5-indanyl.

Particularly preferred individual compounds include:
3-{1-[(cis-4-carboxycyclohexyl)carbamoyl]cyclopentyl}-2-(2-methoxyethoxymethyl)propanoic acid 5-indanyl ester, and
3-{{1-[(cis-4-{5-indanyloxycarbonyl}cyclohexyl)carbamoyl]-cyclopentyl}}-2-(2-methoxyethoxymethyl)-propanoic acid.

In a further particular and more preferred aspect, the invention provides compounds of the formula (II) wherein R, $R^3$ and $R^4$ are each hydrogen, $R^2$ is butyl or $C_3$-$C_4$ alkoxy and $R^5$ is as previously defined for formula (I),. Particularly preferred compounds within this category include those where $R^4$ in —$COOR^4$ is hydrogen and said carboxy group is attached at the 4-position of the cyclohexane ring and has cis-stereochemistry relative to the amide group at the 1-position of the molecule, $R^2$ is butyl and $R^5$ is n-propyl, 2-methoxyethoxymethyl, 2-methoxyethyl, methoxymethyl or allyl. Especially preferred compounds within this group include those wherein $R^2$ is n-butyl attached at the 3-position of the cyclohexane ring. Specific examples of such particularly preferred compounds are as follows:
3-{1-[(cis-4-carboxy-cis-3-n-butylcyclohexyl)-rel-1-carbamoyl]-cyclopentyl}-2S-(2-methoxyethoxymethyl)propanoic acid;
3-{1-[(cis-4-carboxy-trans-3-n-butylcyclohexyl)-rel-1-carbamoyl]cyclopentyl}-2S-(2-methoxyethoxymethyl)propanoic acid; and
3-{1-[(cis-4-carboxy-cis-3-n-butylcyclohexyl)-rel-1-carbamoyl]cyclopentyl}-2-(2-methoxyethyl)propanoic acid.

In a further particular and even more preferred aspect, the invention also provides compounds of the formula (II) wherein $R^2$ and $R^3$ are each hydrogen and $R^5$ is 2-methoxyethoxymethyl, said compounds being (S)-enantiomers of cis-isomeric acids of the formula:

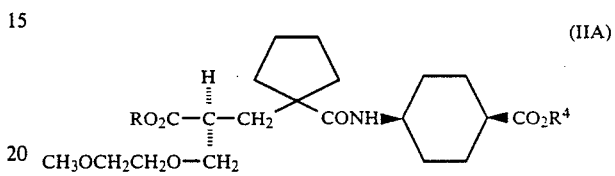

wherein each of R and $R^4$ is hydrogen, or one of R and $R^4$ is hydrogen and the other is a biolabile ester-forming group, with each of said enantiomeric compounds being substantially free of the R-enantiomer. By substantially free of the R-enantiomer is meant that the compounds of formula (IIA) contain less than 10%, and preferably less than 5% of the R-enantiomer. Particularly preferred compounds within this category include those where each R and $R^4$ is hydrogen and those where one of R and $R^4$ is hydrogen and the other is a biolabile ester-forming group such as benzyl or (and most preferably) 5-indanyl. Especially preferred compounds within this latter group include those wherein R and $R^4$ are each hydrogen and those wherein R is 5-indanyl and $R^4$ is hydrogen. Specific examples of such particularly preferred compounds are listed below:

(S)-cis-4-{1-[2-carboxy-3-(2-methoxyethoxy)propyl]-1-cyclopentanecarboxamido}-1-cyclohexanecarboxylic acid, and (S)-cis-4-{1-[2-(5-indanyloxycarbonyl)-3-(2-methoxyethoxy)-propyl]-1-cyclopentanecarboxamido}-1-cyclohexanecarboxylic acid.

DETAILED DESCRIPTION OF THE INVENTION

The compounds of formula (I) are prepared by a number of different processes. The basic procedure involves the synthesis of a partially protected spiro-substituted glutaric acid derivative which is coupled to an amine to give the desired glutaramide. The carboxylic acid group in the amine, if free, or any reactive groups in $R^5$, may require protection during the coupling step and such protecting groups are removed in the final stage of the process.

The synthetic route is illustrated in scheme 1 wherein A, B, $R^1$, $R^2$ and $R^3$ are as previously defined, $R^{5'}$ is as defined for $R^5$ with any reactive group therein protected if necessary and $R^{13}$ and $R^{14}$ are as defined for R and $R^4$ excluding H, or they are conventional carboxylic acid protecting groups:

Scheme 1

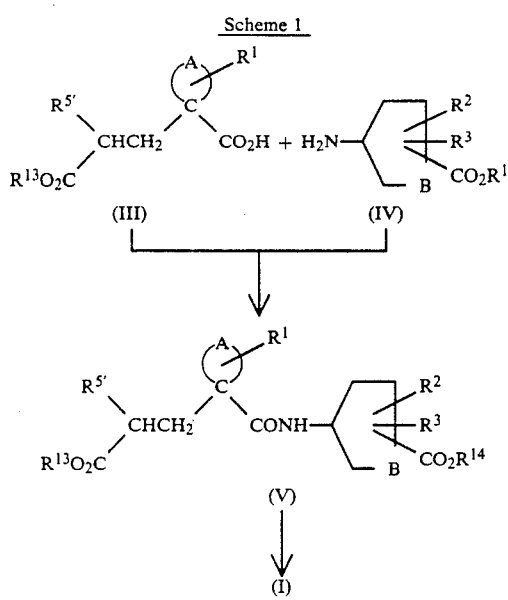

The reaction of the compounds of formula (III) and (IV) is achieved using conventional amide coupling techniques. Thus in one process the reaction is achieved with the reactants dissolved in an organic solvent, e.g. dichloromethane, using a diimide condensing agent, for example 1-ethyl-3-(dimethylaminopropyl)carbodiimide, or N,N'-dicyclohexylcarbodiimide, advantageously in the presence of 1-hydroxybenzotriazole and an organic base such as N-methylmorpholine. The reaction is generally complete after a period of from 12 to 24 hours at room temperature and the product is then isolated by conventional procedures, i.e. by washing with water or filtration to remove the urea biproduct and evaporation of the solvent. The product may be further purified by crystallisation or chromatography, if necessary. The compounds of formula (V) include compounds of formula (I) wherein R and $R^4$ are $C_1$-$C_6$ alkyl or benzyl.

In some cases the coupled product, in protected form, may be subjected to conventional chemical transformation reactions to allow preparation of further compounds of formula (V). Thus for example compounds of formula (V) wherein $R^{5'}$ contains an ester group may be hydrolysed or hydrogenated to generate the carboxylic acid which may be further reacted, for example with an amine, to give amide derivatives.

Similarly compounds wherein $R^{5'}$ contains a substituted or protected amino group (for example a benzylamino, dibenzylamino, benzyloxycarbonylamino or t-butyloxycarbonylamino group) may be converted to the free amines by hydrogenation or hydrolysis as appropriate. The amines produced may be further reacted, thus for example reaction with a sulphonyl halide yields the corresponding sulphonamides, acylation with an acid chloride or anhydride yields the corresponding amides, reaction with an isocyanate yields urea derivatives and reaction with a chloroformate or N-(aryloxycarbonyl)succinimide yields the alkoxycarbonylamino and aryloxycarbonylamino products respectively. Other reactions include, for example, oxidation of a sulphide to yield the corresponding sulphoxide or sulphone derivative; Wacker oxidation of a terminal olefin to give the corresponding methyl ketone which in turn may be further reacted, for example by reductive amination to yield the corresponding amine; hydrogenation of a benzyloxy containing compound to yield the alcohol, reduction of an azide group to give an amine, or reduction of a cycloalkene to a cycloalkane. All these transformations are entirely conventional and appropriate conditions and reagents for their performance will be well known to those skilled in the art as will other variations and possibilities.

The diesters of formula (V) may be further reacted to give the monoester or diacid derivatives of formula (I) wherein one or both of R and $R^4$ are H. The conditions used will depend on the precise nature of the groups $R^{13}$ and $R^{14}$ present in the compound of formula (V) and a number of variations are possible. Thus for example when both of $R^{13}$ and $R^{14}$ are benzyl, hydrogenation of the product will yield the diacid of formula (I) wherein R and $R^4$ are both H. Alternatively if one of $R^{13}$ and $R^{14}$ is benzyl and the other is alkyl, hydrogenation will yield a monoester product. This can then be hydrolysed, if desired, to again yield the diacid product. When one of $R^{13}$ and $R^{14}$ is t-butyl, treatment of the compound of formula (V) with trifluoroacetic acid yields the corresponding acid. The diester product wherein $R^{13}$ and $R^{14}$ are benzyl or lower alkyl can also be treated with trimethylsilyl iodide to produce the dicarboxylic acid product. If some other carboxylic acid protecting group is used for $R^{13}$ or $R^{14}$ then clearly appropriate conditions for its removal must be employed in the final step to give the ester or diacid product of formula (I). In the case where the ring A or the substituent $R^5$ is unsaturated, the deprotection must be effected by non-reductive methods, thus for example if either of R and $R^4$ is benzyl, they may be removed by treatment with trimethylsilyl iodide.

As well as removing any protecting group which may be present in $R^{5'}$, a number of chemical transformation reactions are possible on the final mono-ester or diacid products as previously described. In each case the product may be obtained as the free carboxylic acid or it may be neutralised with an appropriate base and isolated in salt form.

The starting spiro-substituted glutaric acid mono esters of formula III may be prepared by a number of different processes as illustrated by the following reaction scheme:

Scheme 2

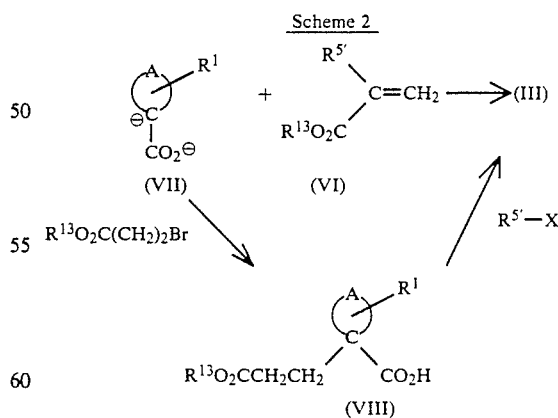

The acrylates of formula (VI) are either known compounds which are commercially available or they may be prepared by conventional methods in accordance with literature methods (for example by reaction of an appropriately substituted malonic acid mono-ester with paraformaldehyde with concomitant decarboxylation).

The acrylate is reacted directly with the dianion derived from the appropriate cycloalkane carboxylic acid by treatment with a strong base (e.g. lithium diisopropylamide) to give the glutaric acid mono ester of formula (III). Alternatively, the acid is reacted with a 3-bromopropionate to give the corresponding ester (VIII). This is then alkylated by reaction with a strong base (e.g. lithium diisopropylamide) at low temperature to generate the dianion followed by addition of the appropriate compound of formula $R^{5'}$—X, wherein X is a leaving group, e.g. trifluoromethane sulphonyloxy or halo, preferably bromo, to again yield the glutaric acid mono ester of formula (III).

The amines of formula (IV) are generally known compounds which are commercially available or they may be prepared by conventional methods in accordance with literature methods (for example, in the case where B is $(CH_2)_2$, by reduction of the corresponding benzoic acid).

Compounds of the formula (I) wherein one or both of R and $R^4$ is a biolabile ester forming group are prepared following similar procedures to those described above.

Thus, in one variant of the process outlined in Scheme 1, a compound of formula (III) wherein $R^{13}$ is a biolabile ester-forming group is coupled to the appropriate compound of formula (IV) wherein $R^{14}$ is a benzyl group, and the product is hydrogenated to give the compound of formula (I) wherein R is a biolabile ester-forming group and $R^4$ is H.

The glutaric mono esters of formula (III) wherein $R^{13}$ is a biolabile ester-forming group are prepared from the corresponding compounds of formula (III) wherein $R^{13}$ is a conventional selectively removable carboxylic acid protecting group, for example t-butyl, by first protecting the free carboxyl group, for example as its phenacyl ester; removing $R^{13}$ by conventional methods appropriate to the particular protecting group employed; forming an ester with the desired biolabile ester-forming group, for example by reaction with a halide of formula $R^{17}X'$ or by reaction with an alcohol of formula $R^{17}OH$ and a diimide condensing agent, wherein $R^{17}$ is a biolabile ester-forming group and X' is chloro, bromo or iodo, preferably chloro; and finally removing the phenacyl protecting group by conventional procedures, for example by reaction with zinc and glacial acetic acid.

The product is then reacted with the amine of formula (IV) using the coupling techniques previously described and the benzyl group $R^{14}$ is finally removed by a conventional catalytic hydrogenation to give the product of formula (I) wherein R is a biolabile ester-forming group and $R^4$ is H.

In an alternative variant of this process, an amine of formula (IV) wherein $R^{14}$ is a biolabile ester-forming group is coupled with a compound of formula (III) wherein $R^{13}$ is a conventional selectively removable protecting group, for example a benzyl group. The coupled product is then deprotected; thus in the case where $R^{13}$ is benzyl, the product is hydrogenated to give the compound of formula (I) wherein R is H and $R^4$ is a biolabile ester-forming group.

In an alternative process, compounds of the formula (I) wherein one of R and $R^4$ is a biolabile ester-forming group, are prepared from the appropriate compound of formula (V) wherein $R^{13}$ and $R^{14}$ are both selectively removable protecting groups by deprotection to remove one of $R^{13}$ or $R^{14}$ followed by esterification, for example by reaction with a halide of formula $R^{17}X'$ wherein $R^{17}$ and X' are as previously defined, and finally removing the other protecting group to give the mono ester product.

Thus in one variant of this procedure, the compound of formula (V) wherein $R^{13}$ is t-butyl and $R^{14}$ in benzyl is deprotected with trifluoroacetic acid to give the compound of formula (I) wherein R is H and $R^4$ is benzyl. Esterification is achieved by, for example, first converting the mono-benzyl ester to its caesium salt by neutralising with caesium carbonate, followed by reaction with the halide of formula $R^{17}X$ by stirring in an inert organic solvent, for example dimethylformamide, for an overnight period. The benzyl group $R^4$ is then removed by a conventional catalytic hydrogenation to give the compound of formula (I) wherein R is a biolabile ester-forming group and $R^4$ is H.

In an alternative variant of this procedure $R^{14}$ is removed from the compound of formula (V), esterification and deprotection gives the compound of formula (I) wherein R is H and $R^4$ is a biolabile ester-forming group.

Finally, in a further process, compounds wherein both of R and $R^4$ are biolabile ester-forming groups may be prepared from the corresponding diacid of formula (I) wherein both of R and $R^4$ are H by a single esterification step, for example by reaction with a halide of formula $R^{17}X$ as previously described or by reaction with an alcohol in the presence of a carbodiimide coupling agent.

Appropriate coupling and protecting methods for all of the above steps and alternative variations and procedures will be well known to those skilled in the art by reference to standard text books and to the examples provided hereafter.

As previously mentioned, the compounds of the invention are potent inhibitors of the neutral endopeptidase (E.C.3.4.24.11). This enzyme is involved in the breakdown of a number of peptide hormones and, in particular we have discovered that it is involved in the breakdown of atrial natriuretic factor (ANF). This hormone consists of a family of related natriuretic peptides, secreted by the heart, of which the major circulating form in humans is known to be the 28 amino-acid peptide referred to as α-hANP (see for example G. A. Sagnella and G. A. MacGreggor, Nature, 1984, 309, 666 and S. A. Atlas and others, Nature, 1984, 309, 717-725). Thus, the compounds of the invention, by preventing the degradation of ANF by endopeptidase E.C.3.4.24.11, can potentiate its biological effects and the compounds are thus diuretic and natriuretic agents of utility in a number of disorders as previously described.

Activity against neutral endopeptidase E.C.3.4.24.11 is assessed using a procedure based on the assay described by J. T. Gafford, R. A. Skidgel, E. G. Erdos and L. B. Hersh, *Biochemistry*, 1983, 32, 3265-3271. The method involves determining the concentration of compound required to reduce by 50% the rate of release of radiolabelled hippuric acid from hippuryl-L-phenylalanyl-L-arginine by a neutral endopeptidase preparation from rat kidney.

The activity of the compounds as diuretic agents is determined by measuring their ability to increase urine output and sodium ion excretion in saline loaded conscious mice. In this test, male mice (Charles River CD1, 22–28 g) are acclimatised and starved overnight in metabowls. The mice are dosed intravenously via the tail vein, with the test compound dissolved in a volume of saline solution equivalent to 2.5% of body weight. Urine samples are collected each hour for two hours in pre-weighed tubes and analysed for electrolyte concentration. Urine volume and sodium ion concentration from the test animals are compared to a control group which received only saline.

For administration to man in the curative or prophylactic treatment of hypertension, congestive heart failure or renal insufficiency, oral dosages of the compounds will generally be in the range of from 10–1500 mg daily for an average adult patient (70 kg). Thus for a typical adult patient, individual tablets or capsules contain from 2 to 300 mg of active compound, in a suitable pharmaceutically acceptable vehicle or carrier for administration singly, or in multiple doses, once or several times a day. Dosages for intravenous administration would typically be within the range 5 to 500 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The compounds may be administered alone but may also be administered together with such other agents as the physician shall direct to optimise control of blood pressure or to treat congestive heart failure, renal insufficiency or other disorders in any particular patient in accordance with established medical practice. Thus the compounds can be co-administered with a variety of cardiovascular agents, for example with an ACE inhibitor such as captopril or enalapril to facilitate the control of blood pressure in treatment of hypertension; or with digitalis, or another cardiac stimulant or with an ACE inhibitor, for the treatment of congestive heart failure. Other possibilities include co-administration with a calcium antagonist (e.g. nifedipine or diltiazem) a beta-blocker (e.g. atenolol) or an alpha-blocker (e.g. prazosin) as shall be determined by the physician as appropriate for the treatment of the particular patient or condition involved.

In addition to the above, the compounds may also be administered in conjunction with exogenous ANF, or a derivative thereof or related peptide or peptide fragment having diuretic/natriuretic activity or with other ANF-gene related peptides (e.g. as described by D. L. Vesely et al, Biochem. Biophys. Res. Comm., 1987, 143, 186).

Thus in a further aspect the invention provides a pharmaceutical composition comprising a compound of the formula (I) or (II), or a pharmaceutically acceptable salt thereof or bioprecursor therefor, together with a pharmaceutically acceptable diluent or carrier.

The invention also includes a compounds of the formula (I) or (II), or a pharmaceutically acceptable salt thereof or bioprecursor therefor, for use in medicine, in particular in the treatment of hypertension, congestive heart failure or renal insufficiency in a human being.

Finally, based on our discovery that the neutral endopeptidase E.C.3.4.24.11 is involved in the breakdown of atrial natriuretic factor (ANF) and that compounds which are inhibitors of neutral endopeptidase E.C.3.4.24.11 can be used to prevent degradation of ANF by endopeptidase E.C.3.4.24.11 and thus potentiate its diuretic and natriuretic activity; the invention includes the use of a compound having the ability to inhibit the neutral endopeptidase E.C.3.4.24.11 for the manufacture of a medicament to prevent degradation of ANF and thus potentiate its diuretic and natriuretic action in the treatment of hypertension, heart failure, angina, renal insufficiency, premenstrual syndrome, cyclical oedema, Menières disease, hyperaldosteronism (primary and secondary), hypercalciuria or glaucoma.

The preparation of the compounds of the invention and of intermediates for use in their preparation is illustrated by the following Examples, in which Examples 1–14 describe the preparation of certain starting materials of formula (VI), Examples 15–69 describe the preparation of glutaric acid derivatives of formula (III), Examples 70–80 describe the preparation of certain amine starting materials of formula (IV), Examples 81–216 describe the preparation of diesters of formula (V), Examples 217–405 and 429–430 describe the preparation of mono and dicarboxylic acids of formula (I) wherein one or both of R and $R^4$ is H, and Examples 406–428 describe the preparation of various pro-drug esters where one or both of R and $R^4$ is a biolabile ester-forming group. Additionally, Examples 431–445 describe the preparation of certain (S)-enantiomers of the compounds of the invention and their biological activity, while Examples 446–454 describe the step-wise preparation and biological activity of certain compounds of the invention wherein $R^2$ is restricted exclusively to n-butyl.

In Examples 431–445, it should be noted that the compounds have been named according to an alternate system of nonenclature. However, as those skilled in the art will well appreciate, the final products of say, for instance, Examples 434 (or 444) and 439, which are now named (S)-cis-4-{1-[2-carboxy-3-(2-methoxyethoxy)-propyl]-1-cyclopentane carboxamido}-1-cyclohexanecarboxylic acid and (S)-cis-4-{1-[2-(5-indanyloxycarbonyl)-3-(2-methoxyethoxy)propyl]-1-cyclopentanecarboxamido}-1-cyclohexanecarboxylic acid, correspond exactly in structure to (S)-3-{1-[(cis-4-carboxycyclohexyl)carbamoyl]cyclopentyl}-2-(2-methoxyethoxymethyl)propanoic acid and its 5-indanyl ester, respectively. The purity of the compounds in these particular examples was routinely monitored by thin layer chromatography using Merck Kieselgel 60 $F_{254}$ plates. $^1$H-Nuclear magnetic resonance spectra were recorded using a Nicolet QE-300 spectrometer and were in all cases consistent with the proposed structures.

EXAMPLE 1

2-(2-Methoxyethyl)propenoic acid benzyl ester

Dibenzyl malonate (28.43 g, 0.1 mole) was added dropwise over 1 hour to a stirred suspension of sodium hydride (3.15 g, 80% dispersion in oil; 0.105 mole) in dry tetrahydrofuran (100 ml) under nitrogen, the temperature being allowed to rise to 40° C. 2-Methoxyethyl bromide (13.9 g, 0.1 mole) was added to the resulting clear solution, which was stirred at room temperature for two hours, and then refluxed overnight. Water was added, and the mixture extracted with methylene chloride. The organic extract on washing with water, drying (MgSO$_4$) and evaporation under vacuum gave a crude liquid (30.94 g). Chromatography on silica gel (700 g) eluting with a mixture of ether and hexane (2:8 by volume) gave 2-methoxyethyl-malonic acid dibenzyl ester as a colourless liquid (15.6 g). This was dissolved in dioxan (150 ml) and a solution of potassium hydroxide (2.55 g, 45.44 mmole) in water (40 ml) added at 0° C. with stirring. The mixture was stirred overnight at room temperature and the solvent was evaporated under vacuum. Water was added and the mixture was extracted with ether to remove unreacted diester. The aqueous phase was then acidified with 2N hydrochloric acid (50 ml) and extracted with ether. The organic extract on washing with water, drying (MgSO$_4$) and evaporation under vacuum gave the mono-ester as a colourless oil (8.95 g, 78%).

Paraformaldehyde (1.6 g, 53.34 mmole) was added to a stirred solution of the crude mono-ester (8.95 g, 35.48 mmole) and piperidine (502 mg, 5.9 mmole) in pyridine (70 ml). After stirring at 60° C. for two and a half hours, the mixture was cooled, poured onto ice, acidified with concentrated hydrochloric acid, and extracted with ether. The organic extract was sequentially washed with water, saturated aqueous sodium bicarbonate and water, dried (MgSO$_4$), and evaporated under vacuum to give a liquid (7.42 g) which was chromatographed on silica gel (300 g). Elution with a mixture of ether and hexane (2:8 by volume) gave the required propenoic acid benzyl ester as a colourless liquid (7.13 g, 92%). Found: C,70.69; H,7.42. C$_{13}$H$_{16}$O$_3$ requires C,70.89; H,7.32%.

EXAMPLES 2–4

The following compounds were prepared by the general procedure of Example 1 using propyliodide, 2-vinylpyridine or t-butyl acrylate respectively as starting material instead of 2-methoxyethyl-bromide.

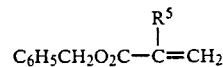

| Example No. | R$^5$ | C | H | N |
|---|---|---|---|---|
| 2 | CH$_3$(CH$_2$)$_2$— | 76.37 (76.44 | 8.01 7.90) | |
| 3 | ![pyridyl]—(CH$_2$)$_2$— | 75.95 (76.38 | 6.41 6.41 | 5.20 5.24) |
| 4 | (CH$_3$)$_3$CO$_2$C(CH$_2$)$_2$— | 70.48 | 7.72 | |
| | | (70.32 | 7.64) | |

Analysis % (Theoretical in brackets)

EXAMPLE 5

2-(2-Methylthioethyl)propenoic acid benzyl ester

Sodium hydride (0.96 g, 50% suspension in mineral oil) was added to a stirred solution of t-butyl benzyl malonate (5 g) in dry dimethylformamide (50 ml), maintained at 0° C. under an atmosphere of nitrogen. After stirring for 15 minutes, 2-chloroethyl-methyl sulphide (2.21 g) in dimethylformamide (10 ml) was added dropwise, while the temperature of the reaction was maintained below 10° C. The reaction was allowed to warm to room temperature and stirred for 15 hours when water was cautiously added. The reaction mixture was extracted with ethyl acetate (2×100 ml), the ethyl acetate extracts were washed with water (4×), dried (Na$_2$SO$_4$) and evaporated to give 4-methylthio-2-t-butyloxycarbonyl-butanoic acid benzyl ester as an oil (6.4 g). This product was dissolved in trifluoroacetic acid (50 ml) with vigorous stirring at 0° C. under nitrogen. After stirring for 45 minutes, the trifluoroacetic acid was evaporated under reduced pressure at below 35° C. Final traces of trifuoroacetic acid were removed by azeotroping with carbon tetrachloride (3×20 ml), to leave an oily residue, which was dissolved in pyridine (20 ml). To this solution were added piperidine (0.44 ml) and paraformaldehyde (1.47 g), and the mixture heated at 60° C. under nitrogen for 2 hours. The reaction mixture was cautiously poured onto iced water, and the pH adjusted to 1 using concentrated sulphuric acid. The mixture was extracted with ether (2×100 ml), and the ether extracts dried (Na$_2$SO$_4$) and evaporated under reduced pressure to yield the crude product (5.4 g) as an oil. This was chromatographed over silica gel, eluting with a mixture of hexane and ethyl acetate, to yield the title ester as a colourless oil (1.22 g). Found: C,64.69; H,6.55. C$_{13}$H$_{16}$O$_2$S (0.25 H$_2$O) requires C,64.85; H,6.91%.

EXAMPLE 6

2-(2-Phenethyl)propenoic acid benzyl ester

Titanium tetraethoxide (7.72 g, 33.8 mmole), rinsed in with benzyl alcohol (50 ml) was added under nitrogen to a solution of 2-(2-phenylethyl)propenoic acid ethyl ester (20.23 g, 99 mmole) in benzyl alcohol (400 ml). The resulting solution was stirred at 100° C. under nitrogen for 18 hours, cooled to room temperature, and acidified with 1N hydrochloric acid (140 ml). The mixture was then extracted with a mixture of ether and hexane (1:1 by volume). Washing the organic extract with saturated aqueous sodium bicarbonate caused a thick precipitate to form in the aqueous phase, which when separated was re-extracted with ether/hexane. The combined organic extracts were washed with saturated sodium chloride solution, dried (MgSO$_4$), and the solvent evaporated under vacuum. Distillation of excess benzyl alcohol (63° C., 2 torr) gave the crude product as a brown oil. Chromatography on silica gel (600 g), eluting with hexane containing increasing proportions of methylene chloride (2:8 to 4:6 by volume) gave the required ester (19.04 g, 72%) which was used without further purification.

EXAMPLE 7

2-[2-(1-Oxoisoindolinyl)methyl]propenoic acid t-butyl ester

A solution of isoindolinone (2.13 g, 16 mmole) in dimethylformamide (20 ml) was added to a stirred suspension of 80% sodium hydride (0.53 g, 17.6 mmole) in dry dimethylformamide (20 ml) under nitrogen at room temperature. After 2 hours the orange suspension was cooled to 0° C. and a solution of t-butyl 2-bromomethylpropenate (3.52 g, 16 mmole) in dry dimethylformamide (5 ml) was added slowly. After 0.5 hours at 0° C. the reaction mixture was poured into diethyl ether and the solution washed with water (4×), dilute hydrochloric acid (2×) and dilute aqueous sodium hydrogen carbonate (2×). After drying ($Na_2SO_4$), evaporation of the solvent under vacuum yielded a yellow oil (3.0 g). Chromatography on silica eluting with dichloromethane/hexane and dichloromethane/diethyl ether mixtures gave the pure title propenate as a colourless oil (2.06 g, 47%). Found: C,70.12; H,7.10; N,5.03. $C_{16}H_{19}NO_3$ requires C,70.31; H,7.01; N,5.12%.

EXAMPLES 8–11

The following compounds were prepared following the procedure of Example 7 using appropriate amine starting materials and using potassium carbonate as the base and acetonitrile as the solvent instead of sodium hydride and dimethylformamide respectively.

$$(CH_3)_3CO_2C-\overset{R^5}{\underset{|}{C}}H=CH_2$$

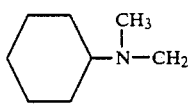

| Example | $R^5$ | Analysis % (Theoretical in brackets) or Thin layer chromatography | | |
|---|---|---|---|---|
| | | C | H | N |
| 8 | $C_6H_5CH_2N-CH_2$ with $CH_3$ | Rf 0.5 (silica; $Et_2O$, $CH_2Cl_2$, 1:9) | | |
| 9 | cyclohexyl-N($CH_3$)-$CH_2$ | Rf 0.65 (silica; $Et_2O$) | | |
| 10 | $C_6H_5CH_2N-CH_2$ with $CH_2CH_3$ | 74.41 (74.14 | 9.39 9.15 | 5.38 5.09) |
| 11 | $(C_6H_5CH_2)_2N-CH_2$ | 78.09 (78.30 | 8.20 8.06 | 4.18 4.15) |

EXAMPLE 12

2-(Benzyloxycarbonylmethyl)propenoic acid t-butyl ester

To a stirred solution of 2-(benzyloxycarbonylmethyl)propenoic acid (25.0 g, 114.0 mmole) in dichloromethane (200 ml) at −78° C. was added condensed isobutylene (50 ml) and concentrated sulphuric acid (1 ml). The mixture was allowed to warm to room temperature and kept for 72 hours. After this time the solution was washed with 10% sodium carbonate solution (3×200 ml), dried over magnesium sulphate and evaporated to give the required ester as a pale yellow oil (28.4 g, 90%). Found: C,69.60; H,7.35. $C_{16}H_{20}O_4$ requires: C,69.55; H,7.30%.

EXAMPLE 13

2-(t-Butoxycarbonylamino)propenoic acid benzyl ester 1,1'-Carbonyldiimidazole (8.10 g, 50 mmole) was added in small portions to a stirred solution of t-butoxycarbonylserine benzyl ester (14.75 g, 50 mmole) and triethylamine (5.05 g, 50 mmole) in dry tetrahydrofuran (100 ml) at room temperature. After stirring at room temperature for 16 hours, the reaction mixture was poured into diethyl ether, the organic phase washed sequentially with dilute hydrochloric acid, water and aqueous sodium carbonate, dried over sodium sulphate and evaporated under vacuum to give an oil (14 g). Chromatography on silica eluting with a mixture of hexane and dichloromethane gave the title propenoate as a yellow oil (10.98 g, 79%). Rf 0.5 (silica; dichloromethane, hexane 1:1).

EXAMPLE 14

2-(Benzyloxycarbonylamino)propenoic acid t-butyl ester

The title compound was obtained via N-benzyloxycarbonyl-O-benzyl-L-serine t-butyl ester which was prepared by a different route to that described in the literature (Recl. Trav. Chim. Pays-Bas, 1964, 83, 99). To a stirred solution of O-benzyl-L-serine (25.0 g, 128 mmole) in water (200 ml) and dioxane (100 ml) was added sodium carbonate (7.46 g, 70 mmole) at room temperature. A solution of dibenzyldicarbonate (36.1 g, 126 mmole) in dioxane (100 ml) was added dropwise and the mixture stirred for 18 hours. Dioxane was evaporated under vacuum and the aqueous residue extracted with diethyl ether. Evaporation of the dried ($Na_2SO_4$) extracts under vacuum gave a white solid which was washed with hexane to yield crude N-benzyloxycarbonyl-O-benzyl-L-serine (39.57 g, 95%). This material was treated with isobutylene (360 ml) and concentrated sulphuric acid (2 ml) in dichloromethane. The reaction mixture was shaken at room temperature in a pressure vessel for 3 days. The mixture was washed with dilute sodium hydrogen carbonate and the dichloromethane evaporated. The residue was dissolved in diethyl ether, washed with dilute sodium hydrogen carbonate, dried ($Na_2SO_4$) and evaporated under vacuum. Purification by column chromatography on silica eluting with diethyl ether-dichloromethane mixtures gave N-benzyloxycarbonyl-O-benzyl-L-serine t-butyl ester (36.66 g, 79%) as an oil. Found: C,68.90; H,7.06; N,3.46. $C_{22}H_{27}NO_5$ requires C,68.55; H,7.06; N,3.63%.

The above compound (36.06 g, 94 mmole) was dissolved in dry t-butanol (500 ml) and treated with potassium t-butoxide (12.59 g, 112 mmole) at room temperature under nitrogen. After 2 hours the reaction mixture was poured into 2N hydrochloric acid (50 ml) and water (350 ml) and extracted with diethyl ether. The extract was washed with brine, dried ($Na_2SO_4$) and the solvent evaporated under vacuum. The residue was purified by column chromatography on silica eluting with dichloromethane-hexane mixtures to yield the title compound as an oil (22.50 g, 80%). Rf. 0.65 (silica; 50% diethyl ether-hexane). Elemental analysis was precluded by polymerisation at room temperature. The product was stored below 0° C.

EXAMPLE 15

3-(1-Carboxycyclopentyl)-2-(2-methoxyethyl)-propanoic acid benzyl ester n-Butyl lithium (2.5M in hexane, 18.16 ml, 45.4 mmole) was added dropwise under nitrogen to a stirred solution of diisopropylamine (4.59, 45.4 mmole) in dry tetrahydrofuran (20 ml) keeping the temperature between −40° and −20° C. Stirring was continued at −20° C. for half an hour and cyclopentane carboxylic acid (2.59 g, 22.7 mmole) in dry tetrahydrofuran (10 ml) was added over five minutes, keeping the temperature at −20° C. The mixture was allowed to attain room temperature over one and a half hours, stirred for a further one hour and then cooled to −73° C. 2-(2-Methoxyethyl)propenoic acid benzyl ester (5.0 g, 22.7 mmole) in dry tetrahydrofuran (10 ml) was added dropwise keeping the temperature below −70° C. After two hours at −77° C., the mixture was quickly warmed to 0° C., acidified with 5N hydrochloric acid, and extracted with hexane. The hexane extract was washed (×7) with a mixture of water and saturated aqueous sodium bicarbonate (1:1 by volume) to remove unreacted cyclopentane carboxylic acid. The extract was washed with water, dried (MgSO4) and evaporated under vacuum to give a pale yellow oil (6.3 g) which was chromatographed on silica gel (600 g). Gradient elution starting with a mixture of ethyl acetate and hexane (3:7 by volume) changing to neat ethyl acetate gave the required product as a colourless oil (4.0 g, 53%). Found: C,68.39; H,7.99. $C_{19}H_{26}O_5$ requires C,68.24; H,7.84%. On prolonged standing the material solidified and when recrystallized from hexane gave a white solid, m.p. 41°-2° C.

EXAMPLES 16–28

The following compounds were prepared by the procedure of Example 15 using as starting material the appropriate propenoic acid ester of Examples 2 to 14. Apart from Examples 16 and 17 the products were obtained as oils. Examples 24 and 25 were isolated as hydrochloride salts. Two molar equivalents of dilithiocyclopentane carboxylic acid dianion were used in the preparation of Examples 20 and 28.

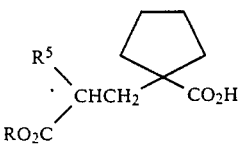

| Example No. | R | R⁵ | Analysis % (Theoretical in brackets) | | |
|---|---|---|---|---|---|
| | | | C | H | N |
| 16 | $C_6H_5CH_2-$ | $CH_3(CH_2)_2-$ | 71.93 (71.67 | 8.09 8.23) | — — |
| 17 | $C_6H_5CH_2-$ | $C_6H_5(CH_2)_2-$ | 75.77 (75.76 | 7.49 7.42) | — — |
| 18 | $C_6H_5CH_2-$ | ⟨pyridyl⟩-(CH₂)₂— | Rf 0.2 (silica: CH₃OH, CH₂Cl₂ CH₃CO₂H, 10:90:1) | | |
| 19 | $C_6H_5CH_2-$ | $(CH_3)_3CO_2C(CH_2)_2-$ | Rf 0.7 (silica; Et₂O) | | |
| 20 | $C_6H_5CH_2-$ | $(CH_3)_3CO_2CNH-$ | 64.40 (64.43 | 7.67 7.47 | 3.55 3.58) |
| 21 | $C_6H_5CH_2-$ | $CH_3S(CH_2)_2-$ | 64.88 (65.12 | 7.29 7.48) | — |
| 22 | $(CH_3)_3C-$ | $C_6H_5CH_2O_2CCH_2-$ | 67.52 (67.67 | 7.88 7.74) | — |
| 23 | $(CH_3)_3C-$ | phthalimidomethyl–N—CH₂— | Rf 0.3 (silica; CH₃OH, CH₂Cl₂, 1:9) | | |
| 24 | $(CH_3)_3C-$ | $C_6H_5CH_2N(CH_3)CH_2-$ | Rf 0.5 (silica: CH₃OH, CH₂Cl₂, 1:9) | | |
| 25 | $(CH_3)_3C-$ | cyclohexyl-N(CH₃)—CH₂— | Rf 0.5 (silica, CH₃OH, CH₂Cl₂, 1:9) | | |
| 26 | $(CH_3)_3C-$ | $C_6H_5CH_2N(CH_2CH_3)CH_2-$ | 69.76 (69.70 | 9.06 8.91 | 3.55 3.52)[1] |
| 27 | $(CH_3)_3C-$ | $(C_6H_5CH_2)_2NCH_2-$ | 74.38 | 8.41 | 2.91 |

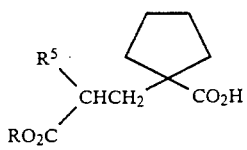

| Example No. | R | R⁵ | Analysis % (Theoretical in brackets) | | |
|---|---|---|---|---|---|
| | | | C | H | N |
| 28 | $(CH_3)_3C-$ | $C_6H_5CH_2OCONH-$ | (74.47<br>64.33<br>(64.43 | 8.26<br>7.71<br>7.47 | 3.10)<br>3.29<br>3.58) |

[1]Solvate with 0.1 $CH_2Cl_2$.

EXAMPLES 29–34

The following compounds were prepared following the procedure of Example 15 but using as starting materials the appropriate cycloalkane or cycloalkene carboxylic acid instead of cyclopentane carboxylic acid, and reacting the anion with 2-propylpropenoic acid benzyl ester or 2-(2-methoxyethyl)propenoic acid benzyl ester as appropriate.

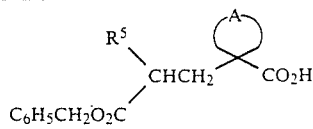

| Example No. | R |  | Analysis % (Theoretical in brackets) | |
|---|---|---|---|---|
| | | | C | H |
| 29 | $CH_3(CH_2)_2-$ | cyclopentane | 72.27<br>(72.12 | 7.76<br>7.65) |
| 30 | $CH_3O(CH_2)_2-$ | cyclopentene | 68.22<br>(68.65 | 7.31<br>7.28) |
| 31 | $CH_3O(CH_2)_2-$ | cyclohexane | 69.10<br>(68.94 | 8.44<br>8.10) |
| 32 | $CH_3O(CH_2)_2-$ | cyclohexene | 69.03<br>(69.34 | 7.85<br>7.57) |
| 33 | $CH_3O(CH_2)_2-$ | methylcyclopentane | 68.95<br>(68.94 | 8.38<br>8.10) |
| 34 | $CH_3O(CH_2)_2-$ | indane | 71.48<br>(72.23 | 6.75<br>6.85) |

EXAMPLE 35

3-(1-Carboxycyclopentyl)propanoic acid t-butyl ester

To a stirred solution of lithium diisopropylamide (0.43 mole) in dry tetrahydrofuran (300 ml) at −20° C. under nitrogen atmosphere was added cyclopentane carboxylic acid (22.7 g; 0.20 mole). The solution was allowed to warm to room temperature and after 2 hours was cooled to −10° C. and added by cannula to a stirred solution of t-butyl 3-bromopropionate (44.4 g, 0.21 mole) in tetrahydrofuran (100 ml). The resulting solution was allowed to warm to room temperature and kept overnight. Hydrochloric acid (3N, 250 ml) was cautiously added, followed by diethyl ether (500 ml) and the layers allowed to separate. The aqueous layer was washed with diethyl ether (300 ml) and the ether layers were combined, washed with water (300 ml), dried over magnesium sulphate and evaporated to give an oil. The oil was taken up in diethyl ether (300 ml) and washed with saturated sodium hydrogen carbonate solution (3×100 ml) until no further cyclopentane carboxylic acid remained. The diethyl ether solution was then extracted with 10% sodium carbonate solution, (4×150 ml), the aqueous phase separated, acidified with 2N hydrochloric acid, and extracted with diethyl ether (3×200 ml). The diethyl ether layer was separated, washed with water (300 ml), dried over magnesium sulphate and evaporated to give an oil that readily crystallised. Recrystallisation from pentane gave a colourless solid (10.4 g, 21%) m.p. 78°–81° C. (from pentane). Found: C,64.70;; H,9.18. $C_{13}H_{22}O_4$ requires: C,64.44; H,9.15%.

EXAMPLE 36

3-(1-Carboxycyclopentyl)propanoic acid ethyl ester was prepared following the procedure of Example 35 starting with ethyl 3-bromopropionate. Found: C,61.91; H,8.53. $C_{11}H_{18}O_4$ requires C,61.66; H,8.47%.

EXAMPLE 37

3-(1-Carboxycyclopentyl)propanoic acid benzyl ester was prepared from benzyl 3-bromopropionate following the procedure of Example 35 to give the benzyl ester as an oil. Found: C,69.76; H,7.18. $C_{16}H_{20}O_4$ requires C,69.55; H,7.29%.

EXAMPLE 38

3-(1-Carboxycyclopentyl)-2(methoxymethyl)propanoic acid t-butyl ester

A solution of t-butyl 3-(1-carboxycyclopentyl)-propanoate (1.0 g, 4.13 mmole) in dry tetrahydrofuran was added to a stirred solution of lithium diisopropylamide (9.29 mmole) in dry tetrahydrofuran (50 ml) at −78° C. under nitrogen. After 0.5 hours, chloromethyl methyl ether (0.53 g, 6.58 mmole) was added and the mixture was allowed to warm to room temperature over 16 hours. The solution was poured into water, acidified to pH 3 with 2N hydrochloric acid and extracted with ethyl acetate (3×50 ml). The organic layer was separated, dried over magnesium sulphate and evaporated to give a colourless oil that was chromatographed on silica gel eluting with a mixture of diethyl ether and dichloromethane (1:9–1:4 by volume). Evaporation of the appropriate fractions gave the title compound as a colourless oil (0.78 g, 66%). Found: C,62.75; H,8.94. $C_{15}H_{26}O_5$ requires: C,62.91; H,9.15%.

EXAMPLES 39–69

The following compounds were prepared by the procedure of Example 38 using as starting materials the appropriate propanoic ester of Example 35, 36 or 37 and the appropriate chloro, bromo, iodo or trifluoromethanesulphonyloxy derivative of formula $R^{5'}X$. Example 50 was obtained as a solid (m.p. 94°–6° C.), the other products were oils.

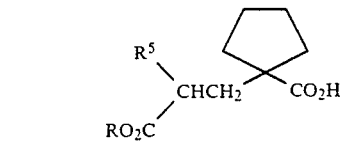

| Example No. | R | $R^5$ | Analysis % (Theoretical in brackets) | | |
|---|---|---|---|---|---|
| | | | C | H | N |
| 39 | $(CH_3)_3C-$ | (pyridin-2-yl)$-CH_2-$ | 62.38 (61.94 | 7.40 7.72 | 3.47 3.42[1] |
| 40 | $(CH_3)_3C-$ | $CH_3O(CH_2)_3-$ | Rf 0.45 (silica, $Et_2O$, hexane, 2:1) | | |
| 41 | $(CH_3)_3C-$ | $C_2H_5O(CH_2)_2-$ | 64.94 (64.94 | 9.55 9.62) | — — |
| 42 | $(CH_3)_3C-$ | $CH_3O(CH_2)_2OCH_2-$ | 61.86 (61.79 | 9.15 9.15) | — — |
| 43 | $(CH_3)_3C-$ | (pyrimidin-2-yl)$-CH_2-$ | 64.35 (64.65 | 8.06 7.84 | 8.14 8.38) |
| 44 | $(CH_3)_3C-$ | $CH_2=CH-CH_2-$ | 67.72 (68.05 | 9.47 9.28) | — |
| 45 | $(CH_3)_3C-$ | $C_6H_5CH_2-N$(imidazolyl)$-CH_2-$ | 69.28 (69.87 | 7.58 7.82 | 6.55 6.79) |
| 46 | $(CH_3)_3C-$ | (pyrrol-2-yl)$-CH_2-$ | 67.52 (67.53 | 8.01 8.20 | 4.24 4.15)[2] |
| 47 | $(CH_3)_3C-$ | $CH_3-C\equiv C-CH_2-$ | 68.70 (69.36 | 8.78 8.90) | — — |
| 48 | $(CH_3)_3C-$ | $C_6H_5CH_2O-(CH_2)_4-$ | Rf 0.85 (silica; $Et_2O$, $CH_2Cl_2$ 1:4) | | |
| 49 | $(CH_3)_3C-$ | $Br-(CH_2)_4-$ | 55.35 (55.07 | 7.87 8.27) | —[3] |

-continued

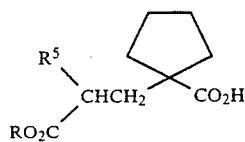

| Example No. | R | R⁵ | Analysis % (Theoretical in brackets) | | |
|---|---|---|---|---|---|
| | | | C | H | N |
| 50 | $(CH_3)_3C-$ | $C_6H_5-\overset{CH_3O}{\underset{\|}{CH}}-$ | 69.90 (69.59 | 8.41 8.34) | — — |
| 51 | $(CH_3)_3C-$ | cyclohexenyl- | 70.55 (70.77 | 9.44 9.38) | — — |
| 52 | $(CH_3)_3C-$ | tetrahydrofuran-CH₂- (4) | Rf 0.4 (silica; Et₂O, CH₂Cl₂ 1:2) | | |
| 53 | $C_2H_5-$ | $CH_3OCH_2CH_2OCH_2-$ | Rf 0.15 (silica; Et₂O, hexane 1:1) | | |
| 54 | $C_2H_5$ | $CH_3(CH_2)_2-$ | 65.40 (65.60 | 9.51 9.44) | — — |
| 55 | $(CH_3)_3C-$ | $CH_3CH_2CO-$ | 64.22 (64.41 | 8.94 8.78) | — — |
| 56 | $C_2H_5-$ | $CH_2=CHCH_2-$ | 65.91 (66.11 | 8.60 8.72) | — — |
| 57 | $(CH_3)_3C-$ | $ClCH_2CH_2-$ | | | |
| 58 | $(CH_3)_3C-$ | cyclopropyl-CH₂- | Rf 0.91 (silica; ethylacetate, toluene, 1:1) | | |
| 59 | $(CH_3)_3C-$ | cyclopentyl- | 69.32 (69.64 | 9.47 9.74 | |
| 60 | $(CH_3)_3C-$ | tetrahydrofuran-2-yl | 65.42 (65.36 | 8.49 9.03) | |
| 61 | $(CH_3)_3C-$ | tetrahydrofuran-3-yl | 66.03 (65.36 | 9.11 9.03) | |
| 62 | $(CH_3)_3C-$ | 1,3-dioxepan-5-yl | 62.01 (62.05 | 8.77 8.87)(5) | |
| 63 | $(CH_3)_3C-$ | $CH_3OCH_2\overset{CH_3}{\underset{\|}{CH}}-$ | 62.83 (63.28 | 9.42 9.38)(6) | |
| 64 | $(CH_3)_3C-$ | $C_6H_5CH_2-$ | 7.19 (7.26 | 8.68 8.41) | |
| 65 | $(CH_3)_3C-$ | 3-(C₆H₅CH₂O)-C₆H₄-CH₂- | 73.34 (73.57 | 7.97 7.83)(7) | |

-continued

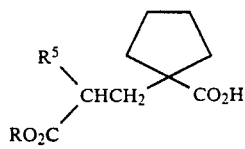

| Example No. | R | R⁵ | C | H | N |
|---|---|---|---|---|---|
| 66 | $(CH_3)_3C-$ | ![benzyl with CH2 and C6H5CH2O2C] | | | |
| 67 | $C_6H_5CH_2-$ | $CH_3C{\equiv}C-CH_2-$ | 70.75 (70.85 | 3.03 3.30)[(8)] | |
| 68 | $CH_3CH_2-$ | $CH_3C{\equiv}C-CH_2-$ | 66.69 (67.64 | 8.79 8.32) | |
| 69 | $CH_3CH_2-$ | cyclohexyl | 69.28 (69.36 | 9.05 8.90) | |

[(1)] Solvate with $CH_3CO_2H$, 0.2 $CH_2Cl_2$
[(2)] 0.25 $H_2O$
[(3)] Solvate with 0.5 $C_4H_{10}O$
[(4)] Using 2-trifluoromethylsulphonyloxymethyl-2,3,4,5-tetrahydrofuran
[(5)] 0.33 $H_2O$
[(6)] Solvate with 0.125 $CH_2Cl_2$
[(7)] 0.125 $H_2O$
[(8)] Hemihydrate

EXAMPLE 70 cis-5-Amino-cis-2-ethyl-r-1-cyclohexanecarboxylic acid methyl ester hydrochloride 5-Amino-2-ethylbenzoic acid (7.0 g, 42.37 mmole) was dissolved in hot ethanol (120 ml) and water (200 ml) and hydrogenated at 45° C. and 50 psi (3.45 bar) pressure over platinum (from $PtO_2$, 1.0 g) for two days. Further amounts of catalyst (1.0 g) were added after seven and twenty four hours. Filtration through avicel and evaporation under vacuum gave a white solid which was dissolved in water and taken up on cation exchange resin (Dow AG 50 W-X8). Elution with 0.5% aqueous pyridine, and evaporation under vacuum gave the crude amino acid as a white solid (5.81 g). Trituration with hot acetone to remove a small amount of starting material, followed by recrystallisation from a mixture of acetone and water and then from acetonitrile and water gave cis-5-amino-cis-2-ethyl-r-1-cyclohexanecarboxylic acid (3.4 g) as a high melting white solid. Found: C,63.02; H, 10.28, N, 8.13. $C_9H_{17}NO_2$ requires C,63.13; H,10.00; N,8.18%.

An ice cold suspension of the above acid (3.35 g, 19.56 mmole) in methanol (100 ml) was stirred and saturated with hydrogen chloride and the resulting solution allowed to stand at room temperature overnight. Evaporation of the solvent under vacuum followed by trituration of the residue with diethyl ether and recrystallisation from a mixture of diethyl ether and methanol gave the required methyl ester hydrochloride as fine white crystals. (3.57 g, 82%). m.p. 200°-201° C. Found: C,53.86; H,9.05; N,6.14. $C_{10}H_{19}NO_2.HCl$ requires C,54.17; H,9.09; N,6.32%.

EXAMPLE 71 cis-3-Amino-cis-5-methyl-r-1-cyclohexanecarboxylic acid methyl ester hydrochloride 3-Amino-5-methylbenzoic acid (7.2 g, 47.6 mmole) was hydrogenated and worked-up as described in Example 70, to give the cyclohexane carboxylic acid (3.30 g; 44%) as a high melting white solid. Found: C,60.81; H,9.67; N,8.80%. $C_8H_{15}NO_2$ requires: C,61.12; H,9.62; N,6.91%. Esterification of the acid (3.17 g, 20.16 mmole) with hydrogen chloride in methanol as previously described gave the methyl ester hydrochloride as a white solid (3.35 g, 80%). m.p. 172.5°-173.5° C. Found: C,52.36; H,8.63; N,6.62. $C_9H_{17}NO_2.HCl$ requires C,52.04; H,8.73; N,6.74%.

EXAMPLE 72 cis-3-Amino-cis-5-methyl-r-1-cyclohexanecarboxylic acid ethyl ester hydrochloride Esterification of cis-3-amino-cis-5-methyl-r-1-cyclohexane carboxylic acid (2.0 g) with ethanol and hydrogen chloride gave the ethyl ester hydrochloride (1.4 g, 75%). Found: C,51.23; H,8.52; N,7.13. $C_{10}H_{20}NO_2Cl$ requires C,54.17; H,9.09; N,6.32%.

EXAMPLE 73 cis-3-Amino-cis-4-ethyl-r-1-cyclohexanecarboxylic acid methyl ester hydrochloride 3-Amino-4-ethyl benzoic acid (14.0 g, 84.7 mmole) was hydrogenated and worked-up as described in Example 70, to give the cyclohexane carboxylic acid (6.36 g 43%) as a light fibrous white solid. m.p. >250° C. Found: C,61.83; H,9.80; N,8.13. $C_9H_{17}NO_2$. 0.2 $H_2O$ requires C,61.82; H,10.03; N,8.01%. Esterification of the above acid (6.0 g, 35.04 mmole) as described in Example 70 gave the methyl ester hydrochloride as a white solid (7.02 g, 90%). m.p. 161.5°-162° C. Found: C,53.79; H,9.13; N,6.33. $C_{10}H_{19}NO_2.HCl$ requires C,54.17; H,9.09; N,6.32%.

EXAMPLE 74 cis-3-Amino-cis-4-ethyl-r-1-cyclohexane carboxylic acid ethyl ester hydrochloride Esterification of cis-3-amino-cis-4-ethyl-r-1-cyclohexane carboxylic acid (2.5 g) with ethanol and hydrogen chloride gave the ethyl ester hydrochloride (2.0 g, 75%). Found: C,54.31; H,9.53; H,5.92. $C_{11}H_{22}NO_2Cl$ requires C,56.04; H,9.41; N,5.94%.

EXAMPLE 75 cis-3-Amino-cis-4-methyl-r-1-cyclohexanecarboxylic acid methyl ester hydrochloride 3-Amino-4-methylbenzoic acid (3.2 g, 21.2 mmole) was hydrogenated and worked-up as described in Example 42, but without cation exchange chromatography, to give the cyclohexane carboxylic acid (1.31 g, 39%) as a white solid, m.p. 258°-261° C. (decomp.). Found: C,61.03; H,9.89; N,8.90. $C_8H_{15}NO_2$ requires: C,61.11; H,9.62; N,8.91%. Esterification as described in Example 42, gave the methyl ester hydrochloride as a hygroscopic foam (1.31 g, 87%). Found: C,51.84; H,8.99; N,6.73. $C_9H_{17}NO_2.HCl$ requires C,52.03; H,8.73; N,6.74%.

EXAMPLE 76 cis-3-Aminocyclohexanecarboxylic acid ethyl ester hydrochloride cis-3-Aminocyclohexanecarboxyilic acid hydrochloride (5.25 g, 36.7 mmole) was esterified with ethanol and hydrogen chloride, as previously described, to give the ethyl ester hydrochloride as a white solid (6.62 g, 87%). m.p. 163°-4° C. Found: C,51.94; H,8.73; N,6.47. $C_9H_{17}NO_2HCl$ requires C,52.03; H,8.73; N,6.74%.

EXAMPLE 77 cis-3-Aminocyclohexanecarboxylic acid benzyl ester para-toluene sulphonate cis-3-Aminocyclohexanecarboxylic acid hydrochloride (8.78 g, 49 mmole) was refluxed for 24 hours with benzyl alcohol (26.4 g, 0.24 mole) and para-toluenesulphonic acid monohydrate (11.17 g, 0.59 mole) in toluene (150 ml) using a Dean-Stark trap. On cooling and addition of diethyl ether the required benzyl ester crystallised as a white solid (18.68 g, 94%), m.p. 148°-150° C. Found: C,62.21; H,6.75; N,3.34. $C_{21}H_{27}NO_5S$ requires C,62.20; H,6.71; N,3.45%.

EXAMPLE 78 cis-4-Aminocyclohexanecarboxylic acid benzyl ester para-toluene sulphonate

This ester was prepared from cis-4-aminocyclohexanecarboxylic acid hydrochloride following the procedure described in Example 77 and was obtained in 97% yield as a white solid, m.p. 172°-4° C. Found: C,62.21; H,6.61; N,3.33. $C_{21}H_{27}NO_5S$ requires C,62.20; H,6.71; N,3.45%.

EXAMPLE 79 trans-3-Amino-1-propyl-r-1-cyclopentanecarboxylic acid methyl ester (a) 3-Cyclopentenecarboxylic acid (7.5 g, 66.9 mmole) in dry tetrahydrofuran (15 ml) was added dropwise under nitrogen to a stirred solution of lithium diisopropylamide prepared from diisopropylamine (19.7 ml, 0.14 mole) and 2.5M n-butyl lithium in hexane (56.2 ml, 0.14 mole) in dry tetrahydrofuran (150 ml) at −60° C. The resulting suspension was allowed to warm to room temperature and then stirred for a further hour, by which time a clear solution was obtained. Iodopropane (7.18 ml, 73.6 mmole) was added dropwise at −60° C., and the mixture was once again allowed to warm to room temperature and then stirred overnight. The solution was cooled to 15° C., water (10 ml) was added followed by 2N hydrochloric acid to pH 3. The organic layer was separated and the aqueous phased extracted twice with methylene chloride. The combined organic extracts were washed with saturated salt solution, dried (MgSO₄) and evaporated under vacuum to give a crude product which was chromatographed on silica gel (200 g), eluting with a mixture of ethyl acetate and hexane to give 1-propyl-3-cyclopentene-carboxylic acid (7.96 g, 77%) as a hygroscopic solid.

(b) Bromine (7.28 g, 45 mmole) in carbon tetrachloride (20 ml) was added dropwise at 6°-10° C. to a stirred solution of the above product (6.39 g, 41 mmole) in carbon tetrachloride (30 ml). After half an hour the solvent was evaporated under vacuum and the residual dibromo derivative refluxed for one and a quarter hours with potassium carbonate (6.8 g, 49 mmole) in methylethylketone (500 ml). The mixture was filtered, evaporated to a small volume, and residue taken up in ether. Washing with water, drying (MgSO₄) and evaporation gave an oil which was chromatographed on silica gel (120 g). Gradient elution with increasing proportions of ethyl acetate in hexane (35:75 to 60:40 by volume) gave 6-endobromo-4-propyl-2-oxabicyclo[2,2,1]heptan-3-one as a pale orange oil (8.79 g, 91%).

(c) The bromo-lactone from step (b), (4.0 g, 17.2 mmole) in absolute ethanol (35 ml) was hydrogenated at 50 psi (3.45 bar) over magnesium oxide (6.92 g, 0.172 mole) and 10% palladium on charcoal (800 mg). The reduction was continued for forty hours; more catalyst (1.0 g) being added after seven and twenty-four hours respectively. The mixture was filtered through avicel, the solvent evaporated under vacuum and the residue chromatographed on silica gel (150 g), eluting with increasing proportions of ether in hexane to give 4-propyl-2-oxabicyclo[2,2,1]heptan-3-one as a colourless oil (1.13 g; 42%).

(d) The lactone from step (c) (1.13 g, 7.28 mmole) was refluxed in methanol (30 ml) containing concentrated sulphuric acid (0.15 ml) for one and a quarter hours. The mixture was evaporated to a small volume and the residue partitioned between ether and water. The organic phase was washed with water, dried over magnesium sulphate and evaporated under reduced pressure to give cis-3-hydroxy-1-propyl-r-1-cyclopentanecarboxylic acid methyl ester as a colourless oil (0.94 g, 70%).

(e) para-Toluenesulphonylchloride (1.43 g, 7.5 mmole) was added portion-wise to an ice cold solution of the hydroxy ester from step (d) (930 mg, 5 mmole) in pyridine (10 ml). The mixture was allowed to warm gradually to room temperature overnight, and after eighteen hours, poured onto iced water. The mixture was extracted with ether, the organic extract being washed sequentially with 1N hydrochloric acid, water, saturated sodium bicarbonate and water. Drying (MgSO$_4$) and evaporation under vacuum gave an oil which was chromatographed on silica gel (80 g) eluting with a mixture of ethyl acetate and hexane to give the required 3-para-toluenesulphonyl derivative (1.5 g, 89%). This compound (1.45 g, 4.3 mmole) was refluxed for eighteen hours with sodium azide (1.11 g, 17 mmole) in methanol (20 ml) and water (10 ml). Most of the methanol was evaporated off under vacuum and the residue was extracted with methylene chloride. The organic extract was washed with water, dried (MgSO$_4$) and evaporated under vacuum to give an oil which was chromatographed on silica gel (40 g). Gradient elution with a mixture of ethyl acetate and hexane give trans-3-azido-1-propyl-r-1-cyclopentanecarboxylic acid methyl ester as a colourless oil (0.79 g, 89%).

(f) The azide from step (e), (730 mg, 3.4 mmole) in methanol (25 ml) was hydrogenated for four hours at 50 psi pressure over 10% palladium on charcoal (80 mg). The mixture was filtered through a short Avicel column and evaporated under vacuum to give the required title amine (619 mg, 97%) as a pale yellow hygroscopic oil. Found: C,54.93; H,9.59; N,5.79%. $C_{10}H_{19}NO_2.2H_2O$ requires C,54.27; H,10.47; N,6.33%.

EXAMPLE 80 trans-3-Amino-cis-4-hydroxy-1-propyl-r-1-cyclopentanecarboxylic acid methyl ester (a) 6-endo-Bromo-4-propyl-2-oxabicyclo[2,2,1]heptan-3-one from Example 48(b) (2.0 g, 8.6 mmole) was refluxed in methanol (30 ml) containing concentrated sulphuric acid (0.15 ml) for one and a quarter hours. The mixture was evaporated to a small volume and the residue was partitioned between ether and water. The organic extract was washed with water, dried (MgSO$_4$) and evaporated under reduced pressure to give cis-3-bromo-cis-4-hydroxy-1-propyl-r-1-cyclopentanecarboxylic acid methyl ester as an oil (2.18 g, 98%).

(b) The product from step (a) (2.14 g, 8.1 mmole) was refluxed with sodium azide (2.10 g, 32.3 mmole) in methanol (25 ml) and water (15 ml). After forty-eight hours a further amount of sodium azide (1.0 g) was added and reaction continued for four days. Most of the methanol was removed by evaporation under vacuum and the residue was extracted with methylene chloride. The extract was washed with water, dried (MgSO$_4$) and evaporated under vacuum to give an oil which was chromatographed on silica gel (100 g). Gradient elution with increasing proportions of ethyl acetate in hexane gave trans-3-azido-cis-4-hydroxy-1-propyl-r-1-cyclopentanecarboxylic acid methyl ester as a colourless oil (1.24 g, 68%).

(c) The azide from step (b) was reduced as described in Example 50(f) to give the desired amino ester as an oil (1.06 g, 98%). Found: C,58.14; H,9.32; N,6.31%. $C_{10}H_{19}NO_3,0.25 H_2O$ requires C,58.37; H9.55; N6.81.

EXAMPLE 81

3-{1-[cis-4-Benzyloxycarbonyl-cyclohexyl)carbamoyl]-cyclopentyl}-2-(2-methoxyethyl)propanoic acid benzyl ester 1-Ethyl-3-(3-dimethylaminopropyl)carbodiimide hydrochloride (1.15 g, 6 mmole) was added to an ice cold stirred mixture of 3-(1-carboxycyclopentyl)-2-(2-methoxyethyl)propanoic acid benzyl ester (1.0 g, 3 mmole), cis-4-amino-cyclohexanecarboxylic acid benzyl ester p-toluenesulphonate (1.21 g, 3 mmole), 1-hydroxybenzotriazole (405 mg, 3 mmole) and N-methylmorpholine (910 mg, 9 mmole) in dry methylene chloride (30 ml). After half an hour the mixture was allowed to attain room temperature and stirred for eighteen hours. The solvent was evaporated under vacuum and the residue partitioned between ether and water. The organic extract was washed sequentially with water, 2N hydrochloric acid, water, saturated aqueous sodium bicarbonate, and water. Drying (MgSO$_4$) and evaporation under vacuum gave an oil (1.6 g) which was chromatographed on silica gel (110 g) eluting with a mixture of ether and hexane (1:1 by volume) to give the required diester as a colourless oil (1.12 g, 67%). Found: C,72.07; H,8.00; N,2.52. $C_{33}H_{43}NO_6$ requires C,72.10; H,7.89; N,2.55%.

EXAMPLES 82–159

The following compounds of formula (V) wherein $R^{13}$ and $R^{14}$ are each $C_1$-$C_6$ alkyl or benzyl were prepared by the general procedure of Example 81 starting with the appropriate glutaric acid derivative of formula (III) from Examples 15–69 coupling with the appropriate amine of formula (IV). The products were obtained as gums and oils. The stereochemistry of the cycloalkane substituents $R^2$ and $CO_2R^4$ is given with reference to the 1-carbamoyl substituent.

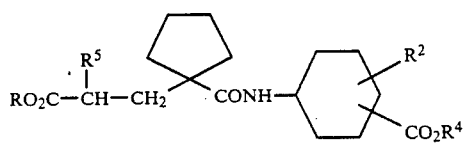

| Example No. | R | $R^5$ | $R^2$ | $-CO_2R^4$ | Analysis % (Theoretical in brackets) | | |
|---|---|---|---|---|---|---|---|
| | | | | | C | H | N |
| 82 | $C_6H_5CH_2-$ | $CH_3(CH_2)_3-$ | H | 4-$CO_2CH_2C_6H_5$ (cis) | 74.21 (74.26 | 8.16 8.12 | 2.80 2.62) |
| 83 | $C_6H_5CH_2-$ | $C_6H_5(CH_2)_2-$ | H | 4-$CO_2C_2H_5$ (cis) | 73.20 (74.26 | 7.69 8.12 | 2.60 2.63) |

-continued

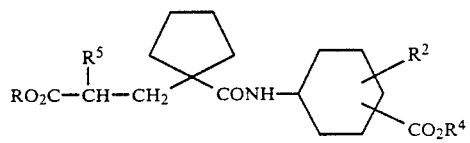

| Example No. | R | R⁵ | R² | —CO₂R⁴ | Analysis % (Theoretical in brackets) C | H | N |
|---|---|---|---|---|---|---|---|
| 84 | $C_6H_5CH_2-$ | 2-pyridyl-$(CH_2)_2-$ | H | $4-CO_2CH_2C_6H_5$ (cis) | 74.53 (74.47 | 7.74 7.43 | 4.83 4.69) |
| 85 | $C_6H_5CH_2-$ | $(CH_3)_3CO_2C(CH_2)-$ | H | $4-CO_2CH_2C_6H_5$ (cis) | 71.72 (71.70 | 7.95 7.97 | 2.38 2.26) |
| 86 | $C_6H_5CH_2-$ | $(CH_3)_3CO_2CNH-$ | H | $4-CO_2CH_2C_6H_5$ (cis) | 68.23 (68.27 | 7.71 7.69 | 4.59 4.55)[2] |
| 87 | $C_6H_5CH_2-$ | $CH_3S(CH_2)_2-$ | H | $4-CO_2C_2H_5$[4] (cis) | 66.24 (66.77 | 8.24 8.21 | 3.22 2.78) |
| 88 | $(CH_3)_3C-$ | $C_6H_5CH_2O_2CCH_2-$ | H | $4-CO_2C_2H_5$ (cis) | 68.51 (68.48 | 8.38 8.34 | 2.50 2.58) |
| 89 | $(CH_3)_3C-$ | isoindolinon-2-yl-$CH_2-$ | H | $4-CO_2CH_2C_6H_5$ (cis) | Rf 0.4 (silica; Et₂O) | | |
| 90 | $(CH_3)_3C-$ | $C_6H_5CH_2N(CH_3)CH_2-$ | H | $3-CO_2C_2H_5$[4] (cis) | Rf 0.8 (silica; Et₂O, CH₂Cl₂ 1:9) | | |
| 91 | $(CH_3)_3C-$ | cyclohexyl-$N(CH_3)CH_2-$ | H | $3-CO_2CH_2C_6H_5$ (cis) | Rf 0.85 (silica; CH₃OH, CH₂Cl₂ 1:9) | | |
| 92 | $(CH_3)_3C-$ | $CH_3OCH_2-$ | H | $4-CO_2CH_2C_6H_5$ (cis) | 69.56 (69.43 | 8.78 8.64 | 2.82 2.79) |
| 93 | $(CH_3)_3C-$ | 2-pyridyl-$CH_2-$ | H | $4-CO_2CH_2C_6H_5$ (cis) | 70.60 (70.49 | 8.20 7.91 | 4.92 4.95)[3] |
| 94 | $(CH_3)_3C-$ | $CH_3O(CH_2)_3-$ | H | $4-CO_2CH_2C_6H_5$ (cis) | 70.32 (70.29 | 9.02 8.94 | 2.56 2.64) |
| 95 | $(CH_3)_3C-$ | $C_2H_5O(CH_2)_2-$ | H | $4-CO_2CH_2C_6H_5$ (cis) | 70.22 (70.29 | 8.93 8.94 | 2.69 2.64) |
| 96 | $(CH_3)_3C-$ | $CH_3O(CH_2)_2OCH_2-$ | H | $4-CO_2CH_2C_6H_5$ (cis) | 67.82 (68.23 | 8.53 8.68 | 2.47 2.57) |
| 97 | $(CH_3)_3C-$ | pyrazinyl-$CH_2-$ | H | $4-CO_2CH_2C_6H_5$ (cis) | 68.51 (68.79 | 7.85 7.94 | 7.66 7.52 |
| 98 | $(CH_3)_3C-$ | $CH_2=CH-CH_2-$ | H | $4-CO_2CH_2C_6H_5$ (cis) | 72.13 (72.40 | 8.65 8.71 | 3.18 2.81) |
| 99 | $(CH_3)_3C-$ | $C_6H_5CH_2$-N-imidazolyl-$CH_2-$ | H | $4-CO_2CH_2C_6H_5$ (cis) | 71.70 (71.67 | 7.51 7.91 | 6.42 6.60)[2] |
| 100 | $(CH_3)_3C-$ | 4-pyridyl-$CH_2-$ | H | $4-CO_2CH_2C_6H_5$ (cis) | 71.75 (72.23 | 8.14 8.08 | 5.22 5.11) |
| 101 | $(CH_3)_3C-$ | $CH_3-C\equiv C-CH_2-$ | H | $4-CO_2CH_2C_6H_5$ (cis) | 72.84 (73.05 | 8.55 8.50 | 2.83 2.75) |

-continued

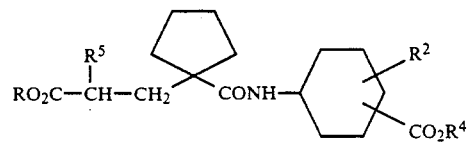

| Example No. | R | R⁵ | R² | —CO₂R⁴ | Analysis % (Theoretical in brackets) C | H | N |
|---|---|---|---|---|---|---|---|
| 102 | $(CH_3)_3C-$ | $Br(CH_2)_4-$ | H (cis) | $4-CO_2CH_2C_6H_5$ | 62.81 (62.83 | 7.76 7.82 | 2.26 2.36) |
| 103 | $(CH_3)_3C-$ | $C_6H_5-CH-$ with $OCH_3$ | H (cis) | $4-CO_2CH_2C_6H_5$ | 72.74 (72.76 | 8.30 8.20 | 2.49 2.42) |
| 104 | $(CH_3)_3C-$ | cyclohexenyl | H (cis) | $4-CO_2CH_2C_6H_5$ | 73.60 (73.71 | 8.92 8.81 | 2.60 2.61) |
| 105 | $(CH_3)_3C-$ | tetrahydrofuranyl-CH₂— | H (cis) | $4-CO_2CH_2C_6H_5$ | 70.10 (70.36 | 8.94 8.77 | 2.56 2.56)[1] |
| 106 | $C_2H_5-$ | $CH_3O(CH_2)_2OCH_2-$ | H (cis) | $4-CO_2CH_2C_6H_5$ | 66.69 (66.43 | 8.67 8.28 | 2.78 2.66)[5] |
| 107 | $C_2H_5-$ | $CH_3(CH_2)_2-$ | H (cis) | $4-CO_2CH_2C_6H_5$ | 71.20 (71.30 | 9.00 8.76 | 3.14 2.97) |
| 108 | $C_6H_5CH_2-$ | $CH_3(CH_2)_2-$ | $4-C_2H_5$ (cis) | $3-CO_2CH_3$ (cis) | 71.60 (71.72 | 8.95 8.93 | 2.73 2.88) |
| 109 | $C_6H_5CH_2-$ | $CH_3(CH_2)_2-$ | $5-CH_3$ (cis) | $3-CO_2CH_3$ (cis) | 71.29 (71.30 | 8.39 8.76 | 2.90 2.97) |
| 110 | $C_6H_5CH_2-$ | $CH_3O(CH_2)_2-$ | $6-C_2H_5$ (cis) | $3-CO_2CH_3$ (cis) | 68.97 (68.96 | 8.48 8.59 | 2.68 2.77)[6] |
| 111 | $C_6H_5CH_2-$ | $CH_3O(CH_2)_2-$ | $6-CH_3$ (cis) | $3-CO_2CH_3$ (cis) | 68.80 (68.96 | 8.50 8.48 | 2.84 2.87) |
| 112 | $C_6H_5CH_2-$ | $CH_3(CH_2)_2-$ | $6-CH_3$ (cis) | $3-CO_2CH_3$ (cis) | 71.39 (71.30 | 8.88 8.76 | 2.74 2.97) |
| 113 | $C_6H_5CH_2-$ | $CH_3(CH_2)_2-$ | $6-CH_3$ H | $3-CO_2CH_2C_6H_5$ (cis) | 73.51 (73.64 | 8.06 8.14 | 2.82 2.60)[1] |
| 114 | $C_6H_5CH_2-$ | $CH_3O(CH_2)_2-$ | H (cis) | $4-CO_2C(CH_3)_3$ | 69.52 (69.87 | 8.98 8.80 | 2.58 2.72) |
| 115 | $C_6H_5CH_2-$ | $CH_3CH_2CH_2-$ | H (cis) | $4-CO_2C(CH_3)_3$ | 72.49 (72.11 | 8.88 9.08 | 2.70 2.80) |
| 116 | $CH_3CH_2-$ | $CH_3-C{\equiv}C-CH_2-$ | H (cis) | $4-CO_2C(CH_3)_3$ | 69.19 (69.77 | 8.78 9.23 | 3.42 3.13) |
| 117 | $C_6H_5CH_2-$ | $CH_3-C{\equiv}C-CH_2-$ | H (cis) | $4-CO_2C(CH_3)_3$ | 72.84 (73.05 | 8.55 8.50 | 2.63 2.70) |
| 118 | $CH_3CH_2-$ | cyclohexenyl | H (cis) | $4-CO_2C(CH_3)_3$ | 70.02 (70.04 | 9.29 9.55 | 2.77 2.92)[1] |
| 119 | $(CH_3)_3C-$ | tetrahydrofuranyl | H (cis) | $4-CO_2CH_2C_6H_5$ | 71.06 (70.56 | 8.40 8.60 | 2.88 2.65) |
| 120 | $(CH_3)_3C-$ | $C_6H_5CH_2O_2C$-phenyl-$CH_2-$ | H (cis) | $4-CO_2C_2H_5$ | 70.22 (70.17 | 8.08 8.04 | 2.11 2.21)[7] |
| 121 | $(CH_3)_3C-$ | $C_6H_5CH_2O$-phenyl-$CH_2-$ | H (cis) | $4-CO_2CH_2C_6H_5$ | 75.40 (75.31 | 8.18 7.86 | 2.07 2.14) |

-continued

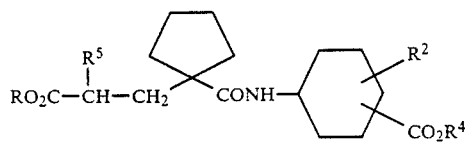

| Example No. | R | R⁵ | R² | —CO₂R⁴ | C | H | N |
|---|---|---|---|---|---|---|---|
| | | | | | (Theoretical in brackets) | | |
| 122 | $(CH_3)_3C-$ | (tetrahydrofuran-2-yl) | H | 4-CO₂C₂H₅ (cis) | 66.79 (67.06 | 9.52 9.31 | 3.08 3.01) |
| 123 | $(CH_3)_3C-$ | (1,3-dioxepan-5-yl) | H | 4-CO₂C₂H₅ (cis) | 62.98 (63.32 | 8.67 8.87 | 2.97 2.71)[1] |
| 124 | $(CH_3)_3C-$ | $CH_3OCH_2CH(CH_3)-$ | H | 4-CO₂C₂H₅ (cis) | 67.01 (66.78 | 9.84 9.70 | 2.98 3.00) |
| 125 | $(CH_3)_3C-$ | $C_6H_5CH_2-$ | H | 4-CO₂CH₂C₆H₅ (cis) | 73.57 (73.94 | 8.49 8.30 | 2.58 2.53)[1] |
| 126 | $(CH_3)_3C-$ | $C_6H_5CH_2O_2CNH-$ | H | 4-CO₂C₂H₅ (cis) | 66.52 (66.15 | 8.18 8.14 | 5.10 5.14) |
| 127 | $(CH_3)_3C-$ | $C_6H_5CH_2N(CH_2CH_3)CH_2-$ | H | 4-CO₂C₂H₅ (cis) | 69.46 (69.37 | 9.22 9.11 | 5.14 5.03)[3] |
| 128 | $(CH_3)_3C-$ | $CH_2=CHCH_2-$ | H | 4-CO₂C₂H₅ (cis) | 68.94 (68.93 | 9.55 9.49 | 3.16 3.22) |
| 129 | $(CH_3)_3C-$ | $CH_3CH_2CO-$ | H | 4-CO₂C₂H₅ (cis) | 66.47 (66.49 | 9.27 9.15 | 2.84 3.10) |
| 130 | $(CH_3)_3C-$ | $(C_6H_5CH_2)_2NCH_2-$ | H | 4-CO₂C₂H₅ (cis) | 73.38 (73.48 | 8.87 8.67 | 4.42 4.68) |
| 131 | $C_2H_5-$ | $CH_2=CHCH_2-$ | H | 4-CO₂C(CH₃)₃ (cis) | 68.92 (68.93 | 9.33 9.49 | 3.16 3.22) |
| 132 | $(CH_3)_3C-$ | $(C_6H_5CH_2)_2NCH_2-$ | H | 3-CO₂C₂H₅ (cis) | Rf. 0.5 (silica; Et₂O, CH₂Cl₂ 1:9) | | |
| 133 | $(CH_3)_3C-$ | $C_6H_5CH_2O_2CNH-$ | H | 3-CO₂C₂H₅ (cis) | 66.06 (66.15 | 8.20 8.14 | 4.92 5.14) |
| 134 | $(CH_3)_3C-$ | $ClCH_2CH_2-$ | H | 3-CO₂C₂H₅ (cis) | | | |
| 135 | $C_6H_5CH_2-$ | $CH_3O(CH_2)_2-$ | 2-OH (cis) | 4-CO₂CH₃ (cis) | 64.59 | 7.88 | 3.19 |
| 136 | $(CH_3)_3C-$ | $CH_3O(CH_2)_2OCH_2-$ | H | 3-CO₂C₂H₅ (cis) | 64.34 (64.57 | 9.37 9.38 | 3.35 2.90) |
| 137 | $(CH_3)_3C-$ | $CH_3O(CH_2)_2OCH_2-$ | H | 3-CO₂CH₂C₆H₅ (cis) | 67.55 (68.23 | 8.71 8.68 | 2.73 2.57) |
| 138 | $(CH_3)_3C-$ | (tetrahydrofuran-3-yl) | H | 3-CO₂C₂H₅ (cis) | 65.73 (67.79 | 9.12 8.34 | 2.75 2.95)[2] |
| 139 | $(CH_3)_3C-$ | $CH_3-C\equiv C-CH_2-$ | H | 3-CO₂C₂H₅ (cis) | 67.43 (67.08 | 8.99 9.23 | 3.33 3.13) |
| 140 | $C_6H_5CH_2-$ | $CH_3CH_2CH_2-$ | H | 3-CO₂C₂H₅ (cis) | 71.08 (71.31 | 8.67 8.76 | 2.88 2.97) |
| 141 | $C_6H_5CH_2-$ | $CH_3O(CH_2)_2OCH_2-$ | H | 3-CO₂CH₂C₆H₅ (cis) | 70.57 (70.52 | 7.81 7.83 | 2.25 2.42) |
| 142 | $C_6H_5CH_2-$ | $CH_3O(CH_2)_2OCH_2-$ | H | 3-CO₂C₂H₅ (cis) | 66.73 (67.28 | 8.35 8.37 | 2.59 2.71) |
| 143 | $C_6H_5CH_2-$ | $CH_3CH_2CH_2-$ | H | 3-CO₂CH₂C₆H₅ (cis) | 73.42 (73.64 | 8.13 8.14 | 2.73 2.60)[1] |
| 144 | $(CH_3)_3C-$ | (cyclohex-1-enyl) | H | 3-CO₂C₂H₅ (cis) | 68.18 (68.71 | 9.06 8.89 | 3.28 3.34) |
| 145 | $(CH_3)_3C-$ | (cyclopropyl)$-CH_2-$ | H | 3-CO₂C₂H₅ (cis) | Rf. 0.73 (silica; ethyl acetate, toluene, 1:1) | | |

-continued

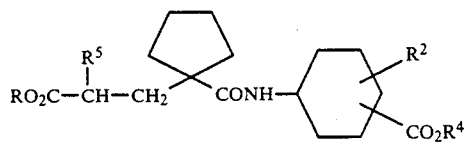

| Example No. | R | $R^5$ | $R^2$ | $-CO_2R^4$ | Analysis % (Theoretical in brackets) | | |
|---|---|---|---|---|---|---|---|
| | | | | | C | H | N |
| 146 | $(CH_3)_3C-$ | cyclopentyl | H | $3-CO_2C_2H_5$ (cis) | Rf. 0.89 (silica; ethyl acetate) | | |
| 147 | $(CH_3)_3C-$ | $C_6H_5CH_2O(CH_2)_4-$ | H | $3-CO_2C_2H_5$ (cis) | 69.89 (69.93 | 9.22 9.24 | 2.88 2.47)[2] |
| 148 | $(CH_3)_3C-$ | $CH_2=CH-CH_2-$ | H | $3-CO_2C_2H_5$ (cis) | 68.06 (68.23 | 9.25 9.51 | 3.22 3.18)[1] |
| 149 | $(CH_3)_3C-$ | $CH_3-C\equiv C-CH_2-$ | H | $3-CO_2CH_2C_6H_5$ (cis) | 71.56 (7.78 | 8.34 8.55 | 2.64 2.70)[2] |
| 150 | $C_6H_5CH_2-$ | $CH_3CH_2CH_2-$ | $5-CH_3$ (cis) | $3-CO_2C_2H_5$ (cis) | Rf. 0.92 (silica; ethyl acetate) | | |
| 151 | $C_6H_5CH_2-$ | $CH_3CH_2CH_2-$ | $6-C_2H_5$ (cis) | $3-CO_2C_2H_5$ (cis) | 7.14 (70.73 | 8.92 8.92 | 2.77 2.74)[8] |

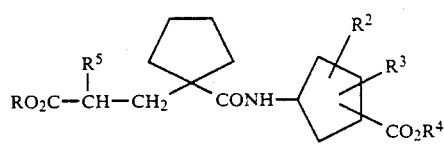

| Example No. | R | $R^5$ | $R^2$ | $R^3$ | $-CO_2R^4$ | Analysis % (Theoretical in brackets) | | |
|---|---|---|---|---|---|---|---|---|
| | | | | | | C | H | N |
| 152 | $C_6H_5CH_2-$ | $CH_3O(CH_2)_2-$ | $3-(CH_2)_2CH_3$ (cis) | H | $3-CO_2CH_3$ (trans) | 68.85 (68.81 | 8.32 8.66 | 2.82 2.77) |
| 153 | $C_6H_5CH_2-$ | $CH_3O(CH_2)_2-$ | $3-(CH_2)_2CH_3$ (cis) | 5-OH (trans) | $3-CO_2CH_3$ (trans) | 66.36 (66.13 | 8.38 8.42 | 2.63 2.66) |

(1) 0.25 hydrate
(2) 0.5 hydrate
(3) Solvate with 0.2 $CH_2Cl_2$
(4) Amine: T. P. Johnston et al, J. Med. Chem., 1971, 14 600
(5) Solvate with 0.1 $CH_2Cl_2$
(6) Solvate with 0.5 $CH_2Cl_2$
(7) 0.75 hydrate
(8) Solvate with 0.143 $CH_2Cl_2$ $C_6H_5CH_2O_2C-\overset{R^5}{\underset{|}{CH}}-CH_2\overset{(A)}{\diagup}CONH\text{-cyclohexyl-}CO_2CH_2C_6H_5$

| Example No. | $R^5$ | (A) | Analysis % (Theoretical in brackets) | | |
|---|---|---|---|---|---|
| | | | C | H | N |
| 154 | $CH_3(CH_2)_2-$ | cyclopentyl | 73.82 (74.55 | 7.50 7.76 | 2.61 2.63) |
| 155 | $CH_3O(CH_2)_2$ | cyclopentenyl | 72.02 (72.37 | 7.63 7.55 | 2.70 2.56) |

-continued $C_6H_5CH_2O_2C-\overset{R^5}{\underset{|}{CH}}-CH_2\overset{A}{\diagup}CONH\text{-cyclohexyl-}CO_2CH_2C_6H_5$

| Example No. | $R^5$ | A | Analysis % (Theoretical in brackets) | | |
|---|---|---|---|---|---|
| | | | C | H | N |
| 156 | $CH_3O(CH_2)_2-$ | cyclohexyl | 72.01 (72.44 | 7.95 8.04 | 2.35 2.48) |
| 157 | $CH_3O(CH_2)_2-$ | cyclohexenyl | 72.91 (72.70 | 8.09 7.72 | 2.55 2.49) |

-continued $C_6H_5CH_2O_2C-\overset{R^5}{\underset{|}{CH}}-CH_2-CONH-\langle A \rangle-\bigcirc-CO_2CH_2C_6H_5$

| Example No. | $R^5$ | ⟨A⟩ | Analysis % (Theoretical in brackets) | | |
|---|---|---|---|---|---|
| | | | C | H | N |
| 158 | $CH_3O(CH_2)_2-$ | $CH_3$ on cyclopentyl | 72.71 (72.44 | 8.32 8.05 | 2.74 2.48) |
| 159 | $CH_3O(CH_2)_2-$ | indanyl | 74.01 (74.34 | 7.45 7.25 | 2.30 2.34) |

EXAMPLE 160

3-{1-[(cis-4-Ethoxycarbonyl-cyclohexyl)carbamoyl]cyclopentyl}-2-ethylthiomethylpropanoic acid t-butyl ester (a) Cyclopentane carboxylic acid dilithio dianion (prepared from cyclopentane carboxylic acid (2.58 g) as described in Example 15) in tetrahydrofuran (100 ml) was treated with zinc chloride (1.85 g) at room temperature for 30 minutes, followed by t-butyl 2-bromomethylpropenoate (5.0 g) at −78° C. The reaction mixture was worked-up and the product purified as previously described to give 3-(1-carboxycyclopentyl)-2-methylenepropanoic acid t-butyl ester as an oil (5.1 g, 89%). Found: C,66.16; H,8.89. $C_{14}H_{22}O_4$ requires C,66.11; H,8.72%.

(b) Coupling of the above acid (4.96 g) with cis-4-aminocyclohexanecarboxylic acid ethyl ester (4.06 g) following the procedure of Example 81 gave 3-{1-[(cis-4-ethoxycarbonylcyclohexyl)carbamoyl]cyclopentyl}-2-methylenepropanoic acid t-butyl ester as an oil (6.2 g, 78%). Found: C,67.94; H,9.35; N,3.54. $C_{23}H_{37}NO_5$ requires C,67.78; H,9.15; N,3.44%.

(c) The above diester (1.38 g, 3.4 mmole) was treated with neat ethanethiol (0.375 ml, 5.1 mmole) and N-benzyltrimethylammonium hydroxide, (7 drops). After 5 days under nitrogen the mixture was dissolved in diethyl ether, washed with dilute hydrochloric acid, dilute sodium bicarbonate, and water, dried ($Na_2SO_4$) and the solvent evaporated to give a yellow oil (1.09 g). Chromatography on silica eluting with a mixture of diethyl ether and dichloromethane gave the title product as an oil (0.51 g, 32%). Found: C,64.23; H,9.14; N,2.98. $C_{25}H_{43}NO_5S$ requires C,63.93; H,9.23; N,2.98%.

EXAMPLE 161

3-{1-[(cis-4-Ethoxycarbonyl-cyclohexyl)carbamoyl]cyclopentyl}-2-ethylsulphonylmethylpropanoic acid t-butyl ester meta-Chloroperbenzoic acid (0.36 g, 2.09 mmole) was added to a stirred solution of 3-{1-[(cis-4-ethoxycarbonylcyclohexyl)carbamoyl]cyclopentyl}-2-ethylthiomethylpropanoic acid t-butyl ester (0.49 g, 1.04 mmole) in dichloromethane (25 ml) at 0° C. The solution was stirred at room temperature for 16 hours, further meta-chloroperbenzoic acid (0.36 g) added and the solution stirred for a further 24 hours. The reaction mixture was diluted with dichloromethane (25 ml), washed with dilute sodium bicarbonate, water and brine, dried ($Na_2SO_4$) and the solvent evaporated. The residue was chromatographed on silica eluting with a mixture of diethyl ether and dichloromethane to give the title sulphone as a white crystalline solid (0.38 g, 73%). Found: C,59.49; H,8.73; N,2.64. $C_{25}H_{43}NO_7S$ requires C,59.85; H,8.64; N,2.79%.

EXAMPLE 162

3-{1-[(cis-4-Benzyloxycarbonyl-cyclohexyl)carbamoyl]cyclopentyl}-2-(2-carboxyethyl)propanoic acid benzyl ester 3-{1-[cis-4-Benzyloxycarbonyl-cyclohexyl)carbamoyl]cyclopentyl}-2-[2-(t-butoxycarbonyl)ethyl]-propanoic acid benzyl ester (3.72 g, 6 mmole) was dissolved in trifluoroacetic acid (35 ml) and stored at 0° C. for 24 hours. The reaction mixture was poured into iced water and extracted with dichloromethane. The organic phase was washed with water, dried ($Na_2SO_4$) and evaporated under vacuum. The residue was crystallised from a mixture of diethyl ether and hexane to give a white solid (1.93 g) which was recrystallised from diethyl ether to give the title acid as a white solid (1.43 g, 42%), m.p. 103°–104° C. Found: C,70.16; H,7.47; N,2.45. $C_{33}H_{41}NO_7$ requires C,70.31; H,7.33; N,2.49%.

EXAMPLE 163

3-{1-[(cis-4-Benzyloxycarbonyl-cyclohexyl)carbamoyl]cyclopentyl}-2-(2-isopropylcarbamoylethyl)-propanoic acid benzyl ester 3-{1-[(cis-4-Benzyloxycarbonyl-cyclohexyl)carbamoyl]cyclopentyl}-2-(2-carboxyethyl)propanoic acid benzyl ester (0.41 g, 0.73 mmole) was dissolved in dry dichloromethane (20 ml) and treated sequentially at room temperature with 1-(3-dimethylaminopropyl)-3-ethyl carbodiimide hydrochloride (0.28 g, 1.46 mmole), N-methylmorpholine (0.22 g, 2.18 mmole), and 1-hydroxybenzotriazole (0.10 g, 0.74 mmole). After stirring for 10 minutes, isopropylamine (0.065 g, 94 mmole) was added and the mixture stirred for 18 hours at room temperature under nitrogen. The reaction mixture was diluted with dichloromethane and the organic phase washed in turn with water, dilute hydrochloric acid and aqueous sodium hydrogen carbonate, dried ($Na_2SO_4$) and evaporated under vacuum to give an oil (0.46 g). Column chromatography on silica gel eluting with dichloromethane and diethyl ether-dichloromethane mixtures yielded the title propanoic acid derivative as an oil (0.09 g, 20%). Rf 0.65 (silica; methanol, dichloromethane 1:9).

EXAMPLES 164–169

The following compounds were prepared following the procedure of Example 163 using the appropriate amine. The products were isolated as gums.

| Example No. | R¹⁶ | Analysis % (Theoretical in brackets) | | |
|---|---|---|---|---|
| | | C | H | N |
| 164 | CH₃O-⟨phenyl with OCH₃⟩-CH₂NH— | Rf 0.6 (silica; Et₂O) | | |
| 165 | (CH₃)₂N— | Rf 0.6 (silica; Et₂O) | | |
| 166 | CH₃NH— | 70.65 (70.81 | 7.66 7.69 | 4.83 4.86) |
| 167 | ⟨cyclopentyl⟩-NH— | 72.17 (72.35 | 8.10 7.99 | 4.61 4.44) |
| 168 | HO-⟨cyclohexyl⟩-NH— | 70.25 (70.88 | 7.89 7.93 | 4.19 4.24) |
| 169 | ⟨thiazole⟩-NH— | 66.67 (66.95 | 6.86 6.71 | 6.31 6.51) |

EXAMPLE 170

3-{1-[(cis-4-Benzyloxycarbonyl-cyclohexyl)carbamoyl]cyclopentyl}-2-(2-carbamoylethyl)propanoic acid benzyl ester 3-{1-[(cis-4-Benzyloxycarbonyl-cyclohexyl)carbamoyl]cyclopentyl}-2-{2-[(2,4-dimethoxyphenyl)methylcarbamoyl]ethyl}propanoic acid benzyl ester (Example 164) (0.37 g, 0.52 mmole) was dissolved in trifluoroacetic acid (10 ml). After stirring for 18 hours at room temperature the deep pink reaction mixture was poured into iced water which was basified with sodium hydrogen carbonate and extracted with dichloromethane. The combined extracts were dried (Na₂SO₄) and evaporated under vacuum. The residue was purified by column chromatography on silica gel eluting with dichloromethane-diethyl ether and methanol dichloromethane mixtures to yield the title ester (110 mg, 38%). Rf 0.25 (silica; ethylacetate).

EXAMPLE 171

3-{1-[(cis-4-Benzyloxycarbonyl-cyclohexyl)-carbamoyl]cyclopentyl}-2-(butanoylamino)propanoic acid benzyl ester A solution of 3-{1-[(cis-4-benzyloxycarbonyl-cyclohexyl)carbamoyl]cyclopentyl}-2-(t-butoxycarbonylamino)propanoic acid benzyl ester (0.71 g, 1.2 mmole) in diethyl ether (50 ml) at 0° C. was saturated with gaseous hydrogen chloride. After 2 hours at room temperature the solvent was evaporated under vacuum and the resulting residue dissolved in dry dichloromethane (30 ml). Triethylamine (0.16 ml, 5.9 mmole) was added at 0° C. followed by butanoyl chloride (0.18 ml, 1.8 mmole). After stirring for 16 hours at room temperature additional butanoyl chloride (0.18 ml, 1.8 mmole) was added and stirring was continued for 0.75 hours. The reaction mixture was washed in turn with dilute aqueous sodium bicarbonate, 1N sodium hydroxide solution and water, dried (Na₂SO₄) and the solvent evaporated under vacuum. The crude product was purified by column chromatography on silica gel eluting with diethyl ether-dichloromethane mixtures, followed by preparative layer chromatography (development with 10% methanol-dichloromethane) to give the title amide (0.15 g, 22%). Rf 0.7 (silica; methanol, dichloromethane 1:9).

EXAMPLE 172

3-{1-[(cis-4-Ethoxycarbonylcyclohexyl)carbamoyl]cyclopentyl}-2-(2-methylsulphonylethyl)propanoic acid benzyl ester meta-Chloro-perbenzoic acid (0.17 g, 80%) was added to a solution of 2-(2-methylthioethyl)-3-{1-[(cis-4-benzyloxycarbonylcyclohexyl)carbamoyl]cyclopentyl}propanoic acid benzyl ester (0.2 g) in dichloromethane (5 ml) at room temperature, and the reaction mixture stirred for 3 days. The mixture was evaporated to dryness under reduced pressure and the residue partitioned between ether and aqueous sodium hydrogen carbonate (5%). The organic phase was dried (Na₂SO₄) and evaporated under reduced pressure to yield the crude product as an oil (0.2 g). Chromatography over silica gel, eluting with a mixture of hexane and ethyl acetate (1:3) gave the sulphone as an oil (0.15 g). Found: C,60.20; H,7.60; N,2.48. $C_{29}H_{41}NO_6S$ requires C,60.74; H,7.83; N,2.53%.

EXAMPLE 173

2-(Carboxymethyl)-3-{1-[(cis-4-ethoxycarbonylcyclohexyl)carbamoyl]cyclopentyl}propanoic acid t-butyl ester 2-(Benzyloxycarbonylmethyl)-3-{1-[(cis-4-ethoxycarbonylcyclohexyl)carbamoyl]cyclopentyl} propanoic acid t-butyl ester (3.50 g, 6.45 mmole) was dissolved in tetrahydrofuran (100 ml) and stirred with 5% palladium on carbon catalyst (200 mg) at room temperature under hydrogen at 50 p.s.i. (3.5 bar). After 36 hours the catalyst was removed by filtration and the solvent evaporated to give the product as a colourless oil (2.8 g, 96%). Found: C,63.28; H,8.70; N,3.20. $C_{24}H_{39}NO_7$ requires C,63.55; H,8.67; N,3.09%.

EXAMPLE 174

3-{1-[(cis-4-Ethoxycarbonyl-cyclohexyl)carbamoyl]cyclopentyl}-2-(morpholinocarbonylmethyl)propanoic acid t-butyl ester 2-(Carboxymethyl)-3-{1-[(cis-4-ethoxycarbonylcyclohexyl)carbamoyl]cyclopentyl}propanoic acid t-butyl ester (1.0 g, 2.21 mmole) was added to a solution of morpholine (230 mg, 2.65 mmole), 1-(3-dimethylaminopropyl)-3-ethylcarbodiimide hydrochloride salt (845 mg, 4.41 mmole), 1-hydroxybenzotriazole hydrate (675 mg, 4.41 mmole) and triethylamine (893 mg, 8.84 mmole) in dry dichloromethane (50 ml) at room temperature. After 4 days the solvent was evaporated and the residue taken up in ethyl acetate (50 ml) and washed with 1N hydrochloric acid (50 ml), water (50 ml) and saturated sodium hydrogen carbonate solution (50 ml). The organic layer was separated, dried over magnesium sulphate and evaporated to give an orange oil. Chromatography on silica gel eluting with diethyl ether followed by ethyl acetate gave the title product as a yellow foam (790 mg, 68%). Found: C,64.63; H,9.09; N,5.23. $C_{28}H_{46}N_2O_7$ requires C,64.34; H,8.87; N,5.36%.

EXAMPLE 175

3-{1-[(cis-4-Ethoxycarbonyl-cyclohexyl)carbamoyl]cyclopentyl}-2-[(2-methoxyethyl)carbamoylmethyl]-propanoic acid t-butyl ester The procedure of Example 174 was followed using 2-methoxyethylamine instead of morpholine to give the title product as a pale yellow oil (740 mg, 66%). Found: C,63.77; H,9.32; N,5.28. $C_{27}H_{46}N_2O_7$ requires C,63.50; H,9.08; N,5.49%.

EXAMPLE 176

2-(2-Acetonyl)-3-{1-[(cis-4-benzyloxycarbonyl-cyclohexyl)carbamoyl]cyclopentyl}propanoic acid t-butyl ester 3-{1-[(cis-4-benzyloxycarbonyl-cyclohexyl)carbamoyl]cyclopentyl}-2-(2-propenyl)propanoic acid t-butyl ester (400 mg, 0.80 mmole) was dissolved in a mixture of water (0.7 ml) and dimethylformamide (5 ml) and was stirred with palladium dichloride (15 mg) and cupric chloride (25 mg) at 60° C. for 18 hours whilst bubbling air through the solution. The solution was cooled, diethyl ether (20 ml) and 1N hydrochloric acid (20 ml) were added and the layers separated. The aqueous layer was extracted with more diethyl ether (20 ml) and the organic layers were combined, dried over magnesium sulphate, evaporated and the residue chromatographed on silica gel eluting with a mixture of diethyl ether and pentane (2:1 by volume). The appropriate fractions were combined and evaporated to give the title product as a pale yellow oil (210 mg, 51%). Rf 0.2 (silica; diethyl ether, hexane 2:1).

EXAMPLE 177

2-(2-Acetonyl)-3-{1-[(cis-4-ethoxycarbonyl-cyclohexyl)carbamoyl]cyclopentyl}propanoic acid t-butyl ester 3-{1-[cis-4-Ethoxycarbonyl-cyclohexyl)carbamoyl]-cyclopentyl}-2-(2-propenyl)propanoic acid t-butyl ester was oxidised following the procedure described in Example 176 to give the title product. Found: C,66.00; H,9.16; N,3.15. $C_{25}H_{41}NO_6$ requires C,66.49; H,9.15; N,3.10%.

EXAMPLE 178

2-(2-N-Benzylaminopropyl)-3-{1-[(cis-4-ethoxycarbonylcyclohexyl)carbamoyl]cyclopentyl}propanoic acid t-butyl ester. Diastereomers A and B 2-(2-Acetonyl)-3-{1-[(cis-4-ethoxycarbonylcyclohexyl)carbamoyl]cyclopentyl}propanoic acid t-butyl ester (1.00 g, 2.2 mmole) was dissolved in methanol (20 ml) and treated sequentially with benzylamine (1.5 ml, 13.8 mmole), 5N methanolic hydrogen chloride (0.8 ml) and sodium cyanoborohydride (0.14 g, 2.2 mmole) and 3A molecular sieves (10) were added. The black solution was stirred for 16 hours at room temperature. Further sodium cyanoborohydride (0.23 g, 3.7 mmole) was added and the pH of the solution adjusted to 7 with 5N methanolic hydrogen chloride and benzylamine. After 16 hours the solvent was removed under vacuum and the residue partitioned between ethyl acetate and 1M aqueous sodium carbonate. The aqueous phase was extracted with ethyl acetate (4×50 ml) with the use of sodium chloride to disperse emulsions. The organic phases were dried (MgSO$_4$) and evaporated to give an orange oil (4 g). Purification by column chromatography on silica, eluting with ethyl acetate-hexane mixtures yielded the two title diastereomers. Diastereomer A (490 mg, 41%) Rf. 0.41 (silica; methanol, ethyl acetate, 5:95). Found: C,70.52; H,9.52; N,5.62. $C_{32}H_{50}N_2O_5$ requires C,70.81; H,9.29; N,5.16%. Diastereomer B (650 mg, 54%) Rf. 0.27 (silica; methanol, ethyl acetate, 5:95). Found: C,70.75; H,9.22; N,5.49. $C_{32}H_{50}N_2O_5$ requires C,70.81; H,9.92; N,5.16%.

EXAMPLE 179

2-(1-N-Benzylaminopropyl)-3-{1-[(cis-4-ethoxycarbonylcyclohexyl)carbamoyl]cyclopentyl}propanoic acid t-butyl ester The title compound was prepared from 2-propionyl-3-{1-[(cis-4-ethoxycarbonyl-cyclohexyl)carbamoyl]cyclopentyl}propanoic acid t-butyl ester by the procedure of Example 178 to give an oil. Found: C,70.96; H,9.47; N,5.22. $C_{32}H_{50}N_2O_5$ requires C,70.81; H,9.29; N,5.16%.

EXAMPLE 180

2-Ethylaminomethyl-3-{1-[(cis-4-ethoxycarbonylcyclohexyl)carbamoyl]cyclopentyl}propanoic acid t-butyl ester 2-(N-Benzyl-N-ethylaminomethyl)-3-{1-[(cis-4-ethoxycarbonylcyclohexyl)carbamoyl]cyclopentyl}-propanoic acid t-butyl ester (3.38 g, 6.2 mmole) was dissolved in, ethanol (70 ml) and hydrogenated at 30 p.s.i. (2 bar) over 20% palladium hydroxide on carbon at room temperature for 16 hours. The catalyst was removed by filtration through an Arbacell pad and the filtrate evaporated under vacuum. The residue was chromatographed on silica eluting with methanol-dichloromethane mixtures to give the title compound as an oil (2.35 g, 83%). Found: C,65.51; H,9.57; N,6.14. $C_{25}H_{44}N_2O_5.0.1$ $CH_2Cl_2$ requires C,65.37; H,9.66; N,6.08%.

EXAMPLES 181-185

The following Examples were prepared by the general procedure of Example 180 starting with the appropriate N-benzylamine for Examples 181-183 and the appropriate N,N-dibenzylamine for Examples 184 and 185.

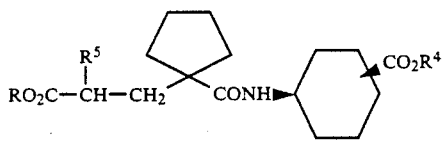

| Example No. | R | $R^5$ | $-CO_2R^4$ | Analysis % (Theoretical in brackets) | | |
|---|---|---|---|---|---|---|
| | | | | C | H | N |
| 181 | $(CH_3)_3C-$ | $CH_3$<br>\|<br>$NH_2CHCH_2-$<br>Diastereomer A | $4\text{-}CO_2C_2H_5$<br>(cis) | Rf. 0.23<br>(silica; $CH_2Cl_2$, $CH_3OH$,<br>$NH_4OH$, 90:10:1) | | |
| 182 | $(CH_3)_3C-$ | $CH_3$<br>\|<br>$NH_2-CHCH_2-$<br>Diastereomer B | $4\text{-}CO_2C_2H_5$<br>(cis) | Rf. 0.20<br>(silica; $CH_2Cl_2$, $CH_3OH$,<br>$NH_4OH$, 90:10:1) | | |
| 183 | $(CH_3)_3C-$ | $CH_2CH_3$<br>\|<br>$NH_2-CH-$ | $4\text{-}CO_2C_2H_5$<br>(cis) | Rf. 0.41 + 0.39<br>(silica; $CH_2Cl_2$, $CH_3OH$,<br>$NH_4OH$, 90:10:1) | | |
| 184 | $(CH_3)_3C-$ | $NH_2CH_2-$ | $4\text{-}CO_2C_2H_5$<br>(cis) | 64.80<br>(65.08 | 9.28<br>9.50 | 6.76<br>6.60) |
| 185 | $(CH_3)_3C-$ | $NH_2CH_2-$ | $3\text{-}CO_2C_2H_5$<br>(cis) | 64.76<br>(65.06 | 9.63<br>9.50 | 6.55<br>6.60) |

EXAMPLE 186

2-Amino-3-{1-[(cis-4-ethoxycarbonyl-cyclohexyl)carbamoyl]cyclopentyl}propanoic acid t-butyl ester 2-Benzyloxycarbonylamino-3-{1-[(cis-4-ethoxycarbonylcyclohexyl)carbamoyl]cyclopentyl}-propanoic acid t-butyl ester (8.11 g, 15 mmole) in 10% aqueous ethanol (320 ml) was hydrogenated at 30 p.s.i. (2 bar) for 4 hours over 10% palladium on carbon. The catalyst was removed by filtration and the filtrate evaporated under vacuum. The residue was azeotroped with dichloromethane (3×50 ml) and dried to give the crude title compound as a gum (6.86 g). Rf. 0.6 (silica; methanol, dichloromethane 5:95).

EXAMPLE 187

2-Amino-3-{1-[(cis-3-ethoxycarbonyl-cyclohexyl)carbamoyl]cyclopentyl}propanoic acid t-butyl ester Hydrogenation of 2-benzyloxycarbonylamino-3-{1-[(cis-3-ethoxycarbonyl-cyclohexyl)carbamoyl]cyclopentyl}propanoic acid t-butyl ester as described above gave the title amine as a gum. Found: C,64.75; H,9.35; N,6.36. $C_{22}H_{38}N_2O_5$ requires C,64.36; H,9.33; N,6.82%.

EXAMPLE 188

2-Benzenesulphonamido-3-{1-[(cis-4-ethoxycarbonyl-cyclohexyl)carbamoyl]cyclopentyl}propanoic acid t-butyl ester 2-Amino-3-{1-[(cis-4-ethoxycarbonyl-cyclohexyl)-carbamoyl]cyclopentyl}propanoic acid t-butyl ester (0.605 g, 1.48 mmole) was dissolved in dry dichloromethane (25 ml) and treated at 0° C. with triethylamine (0.45 g, 4.4 mmole) and benzene sulphonyl chloride (0.24 ml, 1.84 mmole). After stirring for 16 hours at room temperature under nitrogen the dichloromethane was removed under vacuum, the residue taken up in diethyl ether (25 ml), washed with dilute hydrochloric acid, dilute sodium hydrogen carbonate and water, dried ($Na_2SO_4$) and the solvent evaporated under vacuum to give the crude product. Purification by column chromatography on silica, eluting with diethyl etherdichloromethane mixtures, gave pure title compound as a white foam (0.60 g, 74%). Found: C,61.38; H,7.85; N,5.06. $C_{28}H_{42}N_2O_7S$ requires C,61.06; H,7.69; N,5.09%.

EXAMPLES 189-213

The following compounds were prepared following the general procedure of Example 188 starting with the appropriate amine and reacting with the appropriate sulphonyl chloride to yield the sulphonamide products or with an acid chloride, isocyanate, chloroformate or N-(aryloxycarbonyloxy)-succinimide to yield the amide, urea, alkoxycarbonylamino or aralkyloxycarbonylamino products respectively. The products are cis-3- and cis-4-cyclohexane carboxylic acid esters.

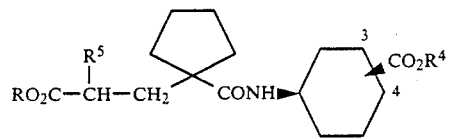

| Example No. | R | R⁵ | —$CO_2R^4$ | Form Isolated | Analysis % (Theoretical in brackets) C | H | N |
|---|---|---|---|---|---|---|---|
| 189 | $(CH_3)_3C-$ | $C_6H_5CH_2CONH-$ | 4-$CO_2C_2H_5$ | Solid m.p. 122–126° C. | 68.15 (68.15 | 8.36 8.39 | 5.17 5.30) |
| 190 | $(CH_3)_3C-$ | $C_6H_5CH_2NHCONH-$ | 4-$CO_2C_2H_5$ | oil | 65.87 (66.27 | 8.37 8.34 | 7.58 7.73) |
| 191 | $(CH_3)_3C-$ | $CH_3(CH_2)_2SO_2NH-$ | 4-$CO_2C_2H_5$ | oil | 57.65 (58.11 | 8.60 8.58 | 5.30 5.42) |
| 192 | $(CH_3)_3C-$ | $C_6H_5CH_2SO_2NH-$ | 4-$CO_2C_2H_5$ | white solid m.p. 133–135° C. | 61.59 (61.67 | 7.94 7.85 | 4.69 4.96) |
| 193 | $(CH_3)_3C-$ | $C_6H_5CH_2OCONCH_2-$ with $CH_2CH_3$ | 4-$CO_2C_2H_5$ | oil | 67.51 (67.55 | 8.55 8.59 | 5.02 4.78) |
| 194 | $(CH_3)_3C-$ | furyl-$CONCH_2-$ with $CH_2CH_3$ | 4-$CO_2C_2H_5$ | oil | 65.74 (65.91 | 8.52 8.48 | 5.21 5.13) |
| 195 | $(CH_3)_3C-$ | $CH_3SO_2NCH_2-$ with $CH_2CH_3$ | 4-$CO_2C_2H_5$ | oil (0.5 $H_2O$) | 57.67 (57.45 | 8.48 8.54 | 5.17 5.12) |
| 196 | $(CH_3)_3C-$ | $C_6H_5CH_2OCONH-CHCH_2-$ with $CH_3$ Diastereomer A | 4-$CO_2C_2H_5$ | solid m.p. 89–90° C. | 67.87 (67.55 | 9.09 8.59 | 4.67 4.58) |
| 197 | $(CH_3)_3C-$ | $C_6H_5CH_2OCONH-CHCH_2-$ with $CH_3$ Diastereomer B | 4-$CO_2C_2H_5$ | oil (0.25 $CH_2Cl_2$) | 65.71 (65.68 | 8.51 8.37 | 4.60 4.61) |
| 198 | $(CH_3)_3C-$ | $CH_3OCONH-CHCH_2-$ with $CH_3$ Diastereomer A | 4-$CO_2C_2H_5$ | solid m.p. 122–124° C. | 62.96 (63.50 | 8.77 9.08 | 5.06 5.49) |
| 199 | $(CH_3)_3C-$ | $CH_3OCONH-CHCH_2-$ with $CH_3$ Diastereomer B | 4-$CO_2C_2H_5$ | oil | 63.04 (63.50 | 8.66 9.08 | 4.83 5.49) |
| 200 | $(CH_3)_3C-$ | $C_6H_5CH_2OCONH-CH-$ with $CH_2CH_3$ | 4-$CO_2C_2H_5$ | oil (0.08 $CH_2Cl_2$) | 66.90 (66.91 | 8.34 8.52 | 4.61 4.72) |
| 201 | $(CH_3)_3C-$ | $C_6H_5CONHCH_2-$ | 4-$CO_2C_2H_5$ | foam | 67.87 (68.15 | 8.40 8.39 | 5.29 5.30) |
| 202 | $(CH_3)_3C-$ | $CH_3CONHCH_2-$ | 4-$CO_2C_2H_5$ | oil (0.3 $H_2O$) | 63.56 (63.53 | 9.03 9.10 | 6.15 5.93) |
| 203 | $(CH_3)_3C-$ | $CH_3(CH_2)_2SO_2NHCH_2-$ | 4-$CO_2C_2H_5$ | foam | 58.54 (58.84 | 8.48 8.74 | 5.50 5.28) |
| 204 | $(CH_3)_3C-$ | $C_6H_5SO_2NHCH_2-$ | 4-$CO_2C_2H_5$ | foam | 60.55 (61.68 | 7.89 7.85 | 4.87 4.96) |
| 205 | $(CH_3)_3C-$ | $CF_3SO_2NH-$ | 4-$CO_2C_2H_5$ | solid m.p. 111–113° C. | 50.88 (50.91 | 7.20 6.87 | 4.97 5.16) |
| 206 | $(CH_3)_3C-$ | $CF_3SO_2NHCH_2-$ | 3-$CO_2C_2H_5$ | foam | 52.33 (51.79 | 7.28 7.06 | 5.00 5.03) |
| 207 | $(CH_3)_3C-$ | $CH_3(CH_2)_2SO_2NH-$ | 3-$CO_2C_2H_5$ | oil | 58.30 (58.11 | 8.81 8.58 | 5.57 5.42) |
| 208 | $(CH_3)_3C-$ | $C_6H_5SO_2NHCH_2-$ | 3-$CO_2C_2H_5$ | foam (0.5 $H_2O$) | 60.62 (60.71 | 7.98 7.91 | 4.96 4.88) |

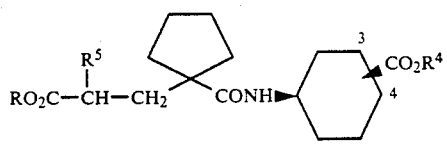

| Example No. | R | R⁵ | —CO₂R⁴ | Form Isolated | Analysis % (Theoretical in brackets) C | H | N |
|---|---|---|---|---|---|---|---|
| 209 | $(CH_3)_3C-$ | [4,5-dimethylthiazol-2-yl-SO₂NHCH₂—] | 3-CO₂C₂H₅ | oil (0.25 H₂O) | 55.54 (55.65 | 7.45 7.59 | 6.65 6.95) |
| 210 | $(CH_3)_3C-$ | [3,5-dimethylisoxazol-4-yl-SO₂NHCH₂—] | 3-CO₂C₂H₅ | oil (0.25 H₂O) | 57.11 (57.17 | 7.72 7.80 | 7.05 7.14) |
| 211 | $(CH_3)_3C-$ | $C_6H_5CONHCH_2-$ | 3-CO₂C₂H₅ | oil | 67.52 (67.57 | 8.35 8.41 | 5.27 5.25) |
| 212 | $(CH_3)_3C-$ | [thiophen-2-yl-SO₂NHCH₂—] | 3-CO₂C₂H₅ | foam | 56.39 (56.82 | 7.51 7.42 | 4.75 4.91) |
| 213 | $(CH_3)_3C-$ | [4-methoxyphenyl-SO₂NHCH₂—] | 3-CO₂C₂H₅ | foam | 60.77 (60.58 | 7.72 7.80 | 4.78 4.71) |

EXAMPLE 214

3-{1-[(cis-4-Benzyloxycarbonyl-cyclohexyl)carbamoyl]cyclopentyl}-2-(4-hydroxybutyl)propanoic acid t-butyl ester 2-(4-Benzyloxybutyl)-3-(1-carboxycyclopentyl)-propanoic acid t-butyl ester (1 g, 2.48 mmole) was dissolved in ethanol (35 ml) and stirred at room temperature with 5% palladium on carbon catalyst (250 mg) under hydrogen at 50 p.s.i. (3.45 bar). After 3 hours the catalyst was removed by filtration and the solvent evaporated. The residue was dissolved in dichloromethane (40 ml) and cis-4-amino-cyclohexanecarboxylic acid benzyl ester p-toluene sulphonate salt (1.5 g, 3.70 mmole), 1-(3-dimethylaminopropyl)3-ethylcarbodiimide hydrochloride salt (1.22 g, 6.37 mmole), 1-hydroxybenzotriazole hydrate (0.97 g, 6.34 mmole) and triethylamine (1.28 g, 12.65 mmole) added. After 3 days at room temperature, the solvent was evaporated and the residue dissolved in ethyl acetate (50 ml). The solution was washed with water (50 ml), 1N hydrochloric acid (50 ml), water (50 ml) and saturated sodium hydrogen carbonate solution (50 ml), dried over magnesium sulphate and the solvent evaporated. The residue was chromatographed on silica gel eluting with a mixture of ethyl acetate and pentane (1:1 by volume) and the appropriate fractions combined and evaporated to give the title product as a pale orange oil (912 mg, 61%). Found: C,70.29; H,8.94; N,2.64. C₃₁H₄₇NO₆ requires C,70.05; H,9.08; N,2.59%.

EXAMPLE 215

3-{1-[(cis-4-Benzyloxycarbonyl-cyclohexyl)carbamoyl]cyclopentyl}-2-(4-pentanoyloxybutyl)-propanoic acid t-butyl ester Valeryl chloride (0.2 ml, 1.98 mmole) was added dropwise to a stirred, ice cold solution of 3-{1-[(cis-4-benzyloxycarbonylcyclohexyl)carbamoyl]cyclopentyl}-2-(4-hydroxybutyl)propanoic acid t-butyl ester (0.7 g, 1.32 mmole) in dry pyridine (5 ml). The mixture was allowed to stand overnight at room temperature and ice was added, the pH was adjusted to 3 by the addition of 2N hydrochloric acid and the mixture was extracted with diethyl ether. The organic extract was dried (Na₂SO₄) and evaporated to give a gum which was chromatographed on silica eluting with hexane containing increasing proportions of diethyl ether to give the title product as a gum (... g ... %). Found: C,70.06; H,8.91; N,2.58. C₃₆H₅₅NO₇ requires C,70.44; H,9.03; N,2.28%.

EXAMPLE 216

2-(4-Azidobutyl)-3-{1-[(cis-4-benzyloxycarbonyl-cyclohexyl)carbamoyl]cyclopentyl}propanoic acid t-butyl ester 2-(4-Bromobutyl)-3-1-[(cis-4-benzyloxycarbonyl-cyclohexyl)carbamoyl]cyclopentyl propanoic acid t-butyl ester (3.1 g, 5.24 mmole) was added to a solution of tetramethylguanadinium azide (1.4 g, 8.86 mmole) and potassium iodide (60 mg) in chloroform (60 ml). The solution was heated under reflux for 3 days, and was then washed with water (2×50 ml), dried over magnesium sulphate and the solvent evaporated to give the product as a yellow oil (2.9 g, 100%). Found: C,66.86; H,8.40; N,9.85. $C_{31}H_{46}N_4O_5$ requires C,67.12; H,8.36; N,10.10%.

EXAMPLE 217

3-{1-[(cis-4-Carboxy-cyclohexyl)carbamoyl]cyclopentyl}-2-(2-methoxyethyl)propanoic acid 3-{1-[(cis-4-Benzyloxycarbonyl-cyclohexyl)carbamoyl]cyclopentyl}-2-(2-methoxyethyl)propanoic acid benzyl ester (1.08 g) in absolute ethanol (30 ml) and water (20 ml) was hydrogenated at room temperature over 5% palladium on charcoal catalyst (200 mg) at 30 p.s.i. pressure for two hours. The reaction mixture was filtered through a short column of Avicel and the solvent evaporated under reduced pressure. The residue was taken up in 1N sodium hydroxide (4 ml) and washed with ether. The aqueous layer was acidified with 2N hydrochloric acid and extracted with methylene chloride. The organic extracts were washed with water, dried (MgSO4) and evaporated under reduced pressure to give the required diacid as a white foam (620 mg, 83%). Found: C,60.07; H,7.64; N,4.07. $C_{19}H_{31}NO_6$,0.05 $CH_2Cl_2$.0.5$H_2O$ requires C,59.89; H,8.46; N,3.67%.

EXAMPLES 218–234

The following compounds were prepared by the procedure of Example 217 starting with the appropriate dibenzyl ester.

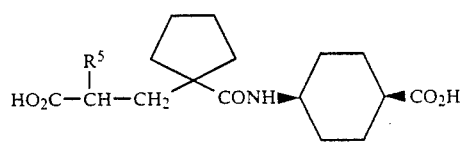

| Example No. | $R^5$ | Isolated Form | Analysis % (Theoretical in brackets) | | |
|---|---|---|---|---|---|
| | | | C | H | N |
| 218 | $CH_3(CH_2)_2$— | Foam | 64.26 (64.56 | 8.92 8.84 | 3.84 3.96) |
| 219 | $C_6H_5(CH_2)_2$ | Foam (0.1 $CH_3CO_2C_2H_5$, 0.7 $CH_2Cl_2$) | 68.23 (68.33 | 8.02 7.95 | 3.16 3.26) |
| 220 | ⟨pyridyl⟩—$(CH_2)_2$— | Foam (1.16 $H_2O$) | 63.64 (63.18 | 7.83 7.85 | 5.80 6.40) |
| 221 | $(CH_3)_3CO_2C(CH_2)_2$— | Foam (0.75 $H_2O$) | 60.82 (60.97 | 8.66 8.57 | 3.16 3.09) |
| 222 | $(CH_3)_2CHNHCO(CH_2)_2$— | Foam (0.75 $H_2O$) | 60.38 (60.32 | 8.55 8.63 | 5.84 6.40) |
| 223 | $(CH_3)_2NCO(CH_2)_2$— | Foam (1.25 $H_2O$) | 58.27 (58.25 | 8.65 8.50 | 5.90 6.47) |
| 224 | $CH_3NHCO(CH_2)_2$— | Foam (0.75 $H_2O$) | 58.85 (58.59 | 8.17 8.23 | 6.29 6.83) |
| 225 | $H_2NCO(CH_2)_2$— | Foam (1.5 $H_2O$) | 56.26 (55.73 | 8.08 8.12 | 6.19 6.84) |
| 226 | $C_6H_5CONH$— | Solid m.p. 208-9° C. | 64.25 (64.17 | 7.49 7.02 | 6.00 6.51) |
| 227 | $CF_3CONH$— | Solid m.p. 136° C. (dec.) (0.75 $H_2O$) | 49.68 (49.60 | 6.41 6.13 | 6.13 6.43) |
| 228 | $CH_3(CH_2)_2CONH$— | Solid (0.25 $H_2O$) | 59.77 (59.90 | 8.17 8.17 | 6.77 6.99) |
| 229 | cyclopentyl—$NHCOCH_2CH_2$— | Foam (0.5 $H_2O$) | 62.98 (62.72 | 8.63 8.55 | 5.77 6.10) |
| 230 | HO—⟨cyclohexyl⟩—$NHCOCH_2CH_2$— | Foam (0.25 $H_2O$) | 61.65 (61.90 | 8.24 8.42 | 5.33 5.77) |
| 231 | $HO_2C(CH_2)_2$— | Foam (0.25 $H_2O$) | 58.91 (58.83 | 8.06 7.67 | 3.32 3.61) |

| Example No. | R⁵ | (A) | Isolated Form | Analysis % (Theoretical in brackets) C | H | N |
|---|---|---|---|---|---|---|
| 232 | CH₃O(CH₂)₂— | cyclohexyl | gum | 61.75 (62.64 | 8.53 8.67 | 3.55 3.65) |
| 233 | CH₃O(CH₂)₂— | 1-methylcyclopentyl | foam | 62.60 (62.64 | 8.94 8.67 | 3.10 3.65) |
| 234 | CH₃O(CH₂)₂— | 2,2-dimethylindanyl | foam (collapses at 70° C.) | 65.94 (66.16 | 8.04 7.49 | 3.30 3.36) |

EXAMPLES 235–240

The following compounds were prepared by the procedure of Example 217 starting with the appropriate mono or dibenzyl ester

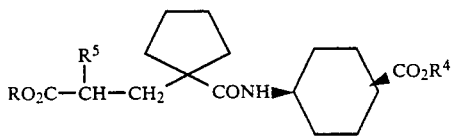

| Example No. | R | R⁵ | —CO₂R⁴ | Analysis % (Theoretical in brackets) C | H | N |
|---|---|---|---|---|---|---|
| 235 | H | CH₃(CH₂)₂— | 3-CO₂H | 64.45 (64.56 | 8.83 8.84 | 3.93 3.96) |
| 236 | C₂H₅ | CH₃O(CH₂)₂OCH₂— | 4-CO₂H | 61.80 (61.81 | 8.64 8.72 | 3.28 3.28) |
| 237 | C₂H₅ | CH₃(CH₂)₂— | 4-CO₂H | 65.22 (65.09 | 9.35 9.28 | 3.73 3.61)⁽¹⁾ |
| 238 | H | CH₃(CH₂)₂— | 3-CO₂C₂H₅ | 65.88 (66.11 | 9.36 9.25 | 3.46 3.69) |

⁽¹⁾0.3 H₂O

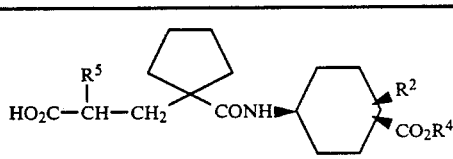

| Example No. | R⁵ | R² | CO₂R⁴ | Analysis % (Theoretical in brackets) C H N |
|---|---|---|---|---|
| 239 | CH₃CH₂CH₂— | 5-CH₃ (cis) | 3-CO₂C₂H₅ (cis) | Rf 0.8 (silica; ethyl acetate) |

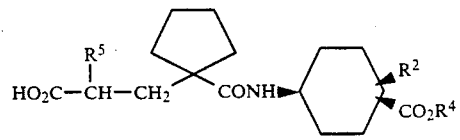

| Example No. | R⁵ | R² | CO₂R⁴ | Analysis % (Theoretical in brackets) C H N |
|---|---|---|---|---|
| 240 | CH₃CH₂CH₂— | 6-C₂H₅ (cis) | 3-CO₂C₂H₅ (cis) | Rf 0.67 (silica; ethyl acetate) |

EXAMPLE 241

3-{1-[(cis-4-Ethoxycarbonylcyclohexyl)carbamoyl]cyclopentyl}2-[3-(N-methylcarbamoyl)phenylmethyl]-propanoic acid tert-butyl ester 3-{1-[(cis-4-Ethoxycarbonylcyclohexyl)carbamoyl]-cyclopentyl}-2-[3-(benzyloxycarbonyl)phenylmethyl]-propanoic acid tert-butyl ester (370 mg, 0.60 mmole) was dissolved in tetrahydrofuran (30 ml) and was stirred with 5% palladium on carbon catalyst (50 mg) under an atmosphere of hydrogen at 50 p.s.i. (3.45 bar) for 5 hours. Further catalyst (50 mg) was added and the hydrogenation was continued for 48 hours. The catalyst was removed by filtration and the solvent evaporated to give a yellow oil. Chromatography on silica gel eluting with a mixture of methanol and ethyl acetate (1:4 to 1:1 by volume) gave a colourless oil. The oil (240 mg) was added to a solution of 1-ethyl-3-(3-dimethylaminopropyl)carbodiimide hydrochloride (170 mg, 0.91 mmole), 1-hydroxybenzotriazole (140 mg, 0.91 mmole), triethylamine (182 mg, 1.80 mmole) and methylamine hydrochloride (31 mg, 0.45 mmole) in dry methylene chloride (20 ml), and the mixture was stirred at room temperature for 6 days. The solvent was evaporated under reduced pressure and the residue partitioned between ethyl acetate and water. The aqueous layer was acidified with 2N hydrochloric acid, separated and extracted three times with ethyl acetate. The organic fractions were combined and washed sequentially with saturated aqueous sodium bicarbonate solution, water and brine. Drying (MgSO4) and evaporation under reduced pressure gave a yellow oil which was chromatographed on silica gel eluting with a mixture of ethyl acetate and pentane (1:1 by volume). Azeotroping with methylene chloride gave the desired amide as a colourless oil (200 mg, 80%). Found: C,67.58; H,8.80; N,5.22. $C_{31}H_{46}N_2O_6.\frac{1}{8}$ $CH_2Cl_2$ requires: C,67.57; H,8.42; N,5.06%.

EXAMPLE 242

3-{1-[(cis-4-Benzyloxycarbonyl-cyclohexyl)carbamoyl]cyclopentyl}-2-(methoxymethyl)propanoic acid 3-{1-[(cis-4-benzyloxycarbonyl-cyclohexyl)carbamoyl]cyclopentyl}-2-(methoxymethyl)propanoic acid t-butyl ester (483 mg, 0.96 mmole) was dissolved in dry trifluoroacetic acid (5 ml) at 0° C. After 18 hours, the solvent was evaporated and the resulting oil azeotroped with dichloromethane (4×20 ml). The oil was taken up in dichloromethane (50 ml) and washed with water (7×50 ml) until the washings were neutral. The organic solution was dried over mangesium sulphate and the solvent evaporated to give a colourless oil (415 mg, 97%). Found: C,65.07; H,7.66; N,3.05. $C_{25}H_{35}NO_6,0.75$ $H_2O$ requires C,65.41; H,8.01; N,3.05%.

EXAMPLES 243-314

The following compounds were prepared by the procedure of Example 242 starting with the appropriate ester of formula (V) wherein $R^{13}$ is t-butyl. The compounds are cis-3- and cis-4-cyclohexane-carboxylic acid esters.

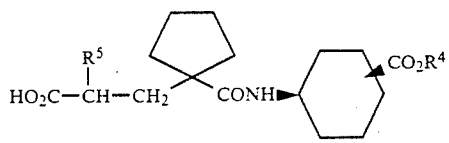

| Example No. | $R^5$ | $-CO_2R^4$ | Isolated Form | Analysis % (Theoretical in brackets) C | H | N |
|---|---|---|---|---|---|---|
| 243 | $CH_3CH_2O(CH_2)_2-$ | $4-CO_2CH_2C_6H_5$ | oil | 68.72 (68.47 | 8.23 8.30 | 2.86 2.96) |
| 244 | $CH_3O(CH_2)_3-$ | $4-CO_2-CH_2C_6H_5$ | oil (0.75 $H_2O$) | 66.61 (66.57 | 8.22 8.38 | 2.88 2.88) |
| 245 | $CH_3O(CH_2)_2OCH_2-$ | $4-CO_2CH_2C_6H_5$ | oil (0.25 $H_2O$) | 65.69 (65.63 | 8.10 8.06 | 2.79 2.83) |
| 246 | ![pyridyl-CH2-] | $4-CO_2CH_2C_6H_5$ | gum | Rf 0.7 (silica; $CH_2Cl_2$, $CH_3OH$, $CH_3CO_2H$ 90:10:1) | | |
| 247 | ![pyrimidyl-CH2-] | $4-CO_2CH_2C_6H_5$ | gum | Rf 0.7 (silica; $CH_2Cl_2$, $CH_3OH$, $CH_3CO_2H$ 90:10:1) | | |
| 248 | $CH_2=CH-CH_2-$ | $4-CO_2-CH_2C_6H_5$ | oil | Rf 0.7 (silica; $CH_3CO_2C_2H_5$) | | |
| 249 | $CH_3COCH_2-$ | $4-CO_2CH_2C_6H_5$ | gum | Rf 0.2 (silica; $CH_2Cl_2$, $CH_3OH$ 95:5) | | |
| 250 | ![C6H5CH2-N-imidazolyl-CH2-] | $4-CO_2CH_2C_6H_5$ | gum | Rf 0.4 (silica; $CH_2Cl_2$, $CH_3OH$, $CH_3CO_2H$ 90:10:1) | | |

-continued

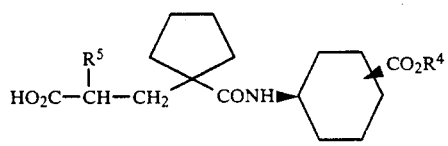

| Example No. | R⁵ | —CO₂R⁴ | Isolated Form | C | H | N |
|---|---|---|---|---|---|---|
| 251 | 4-pyridyl-CH₂— | 4-CO₂CH₂C₆H₅ | gum | Rf 0.6 (silica; CH₂Cl₂, CH₃OH, CH₃CO₂H 90:10:1) | | |
| 252 | CH₃—C≡C—CH₂— | 4-CO₂CH₂C₆H₅ | Solid m.p. 126–128° C. | 71.38 (71.49 | 7.83 7.78 | 3.05 3.09) |
| 253 | cyclohexyl | 4-CO₂CH₂C₆H₅ | gum | 72.03 (72.32 | 8.29 8.16 | 2.81 2.91) |
| 254 | C₆H₅—CH(OCH₃)— | 4-CO₂CH₂C₆H₅ | oil | 71.29 (71.38 | 7.69 7.54 | 2.64 2.69) |
| 255 | tetrahydrofuran-2-yl-CH₂— | 4-CO₂CH₂C₆H₅ | oil (0.2 H₂O) | 68.78 (68.74 | 7.96 8.12 | 2.86 2.86) |
| 256 | C₆H₅CH₂N(CH₃)CH₂— | 3-CO₂C₂H₅ | foam (trifluoroacetate salt) | 60.04 (59.37 | 7.31 7.04 | 4.94 4.78) |
| 257 | cyclohexyl-N(CH₃)—CH₂— | 3-CO₂CH₂C₆H₅ | oil (hydrochloride salt) | Rf 0.25 (silica; CH₃OH, CH₂Cl₂ 1:9) | | |
| 258 | CH₃O(CH₂)₂NHCOCH₂— | 4-CO₂C₂H₅ | foam | Rf 0.15 (silica; CH₂Cl₂, CH₃OH, CH₃CO₂H 95:5:0.5) | | |
| 259 | morpholino-COCH₂— | 4-CO₂C₂H₅ | foam | Rf 0.10 (silica; CH₃CO₂C₂H₅) | | |
| 260 | isoindolin-1-on-2-yl-CH₂— | 4-CO₂C₂H₅ | foam | Rf 0.5 (silica; CH₃OH, CH₂Cl₂ 1:9) | | |
| 261 | CF₃CO₂(CH₂)₄—[1] | 4-CO₂CH₂C₆H₅ | foam | 60.96 (61.15 | 6.79 6.72 | 2.36 2.46) |
| 262 | C₆H₅CH₂OCONH— | 4-CO₂C₂H₅ | foam | Rf 0.25 (silica; CH₃OH, CH₂Cl₂, 10:90) | | |
| 263 | C₆H₅SO₂NH— | 4-CO₂C₂H₅ | solid m.p. 175–177° C. | 58.16 (58.28 | 6.98 6.93 | 5.60 5.67) |
| 264 | C₆H₅CH₂CONH— | 4-CO₂C₂H₅ | foam | Rf. 0.45 (silica; CH₃OH, CH₂Cl₂, 10:90) | | |
| 265 | C₆H₅CH₂NHCONH— | 4-CO₂C₂H₅ | foam | Rf 0.3 (silica; CH₃OH, CH₂Cl₂ 10:90) | | |
| 266 | CH₃(CH₂)₂SO₂NH— | 4-CO₂C₂H₅ | solid m.p. 159–162° C. | 55.02 (54.76 | 8.13 7.88 | 5.89 6.08) |
| 267 | C₆H₅CH₂SO₂NH— | 4-CO₂C₂H₅ | white solid m.p. 161–164° C. | 59.12 (59.03 | 7.13 7.13 | 5.69 5.51) |

-continued

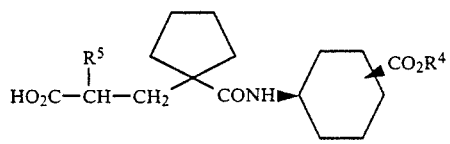

| Example No. | R⁵ | —CO₂R⁴ | Isolated Form | C | H | N |
|---|---|---|---|---|---|---|
| | | | | \multicolumn{3}{c}{Analysis % (Theoretical in brackets)} | | |
| 268 | $C_6H_5CH_2OCON(CH_2CH_3)CH_2-$ | 4-CO₂C₂H₅ | oil (0.1 CH₂Cl₂) | 64.30 (64.82 | 8.02 7.89 | 5.10 5.20) |
| 269 | 2-furyl-CON(CH₂CH₃)CH₂— | 4-CO₂C₂H₅ | foam | Rf 0.4 (silica; CH₃OH, CH₂Cl₂ 10:90) | | |
| 270 | CH₃SO₂N(CH₂CH₃)CH₂— | 4-CO₂C₂H₅ | oil | Rf 0.45 (silica; CH₃OH, CH₂Cl₂ 10:90) | | |
| 271 | $C_6H_5CH_2OCONH-CH(CH_3)CH_2-$ Diastereomer A | 4-CO₂C₂H₅ | oil (1.0 H₂O) | 63.44 (63.48 | 7.79 8.08 | 4.47 5.11) |
| 272 | $C_6H_5CH_2OCONH-CH(CH_3)CH_2-$ Diastereomer B | 4-CO₂C₂H₅ | gum (0.75 H₂O) | 64.29 (64.00 | 7.79 8.06 | 4.62 5.15) |
| 273 | $CH_3OCONH-CH(CH_3)CH_2-$ Diastereomer A | 4-CO₂C₂H₅ | foam | 60.94 (60.77 | 8.49 8.43 | 5.97 6.17) |
| 274 | $CH_3OCONH-CH(CH_3)CH_2-$ Diastereomer B | 4-CO₂C₂H₅ | foam | Rf 0.3 (silica; CH₃OH:CH₂Cl₂ 5:95) | | |
| 275 | $C_6H_5CH_2OCONH-CH(CH_2CH_3)-$ | 4-CO₂C₂H₅ | foam | 65.25 (65.63 | 7.40 7.98 | 4.77 5.28) |
| 276 | C₆H₅CONHCH₂— | 4-CO₂C₂H₅ | solid m.p. 167–168° C. | 66.08 (66.08 | 7.77 7.68 | 5.73 5.93) |
| 277 | CH₃CONHCH₂— | 4-CO₂C₂H₅ | foam | 61.71 (61.44 | 8.57 8.35 | 6.73 6.83) |
| 278 | CH₃(CH₂)₂SO₂NHCH₂— | 4-CO₂C₂H₅ | foam (0.5 H₂O) | 54.66 (54.64 | 8.03 8.13 | 5.73 5.79) |
| 279 | C₆H₅SO₂NHCH₂— | 4-CO₂C₂H₅ | foam (1.0 H₂O) | 57.16 (57.02 | 6.98 7.27 | 5.34 5.31) |
| 280 | CH₃CH₂SO₂CH₂— | 4-CO₂C₂H₅ | gum | 56.61 (56.60 | 8.13 7.92 | 2.87 3.14) |
| 281 | NH₂CH₂— | 3-CO₂C₂H₅ | oil | Rf 0.4 (silica; CH₂Cl₂, CH₃OH, CH₃CO₂H, 80:20:1) | | |
| 282 | CF₃SO₂NH— | 4-CO₂C₂H₅ | solid m.p. 117° C. | 46.77 (46.90 | 6.36 6.01 | 5.56 5.76) |
| 283 | CF₃SO₂NHCH₂— | 3-CO₂C₂H₅ | solid m.p. 176–177° C. | 47.62 (47.99 | 5.96 6.24 | 5.59 5.60) |
| 284 | CH₃(CH₂)₂SO₂NH— | 3-CO₂C₂H₅ | foam | 54.22 (54.76 | 7.94 7.88 | 5.93 6.08) |
| 285 | C₆H₅SO₂NHCH₂— | 3-CO₂C₂H₅ | foam (0.25 H₂O) | 58.73 (58.51 | 6.89 7.17 | 5.50 5.46) |
| 286 | 2-methyl-4-methylthiazol-5-yl-SO₂NHCH₂— | 3-CO₂C₂H₅ | foam | 53.08 (53.02 | 6.96 6.86 | 7.60 7.73) |

-continued

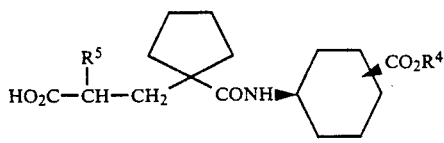

| Example No. | R⁵ | —CO₂R⁴ | Isolated Form | Analysis % (Theoretical in brackets) C | H | N |
|---|---|---|---|---|---|---|
| 287 | 3,5-dimethylisoxazol-4-yl-SO₂NHCH₂— | 3-CO₂C₂H₅ | foam | 54.43 (54.63 | 7.06 7.07 | 8.44 7.96) |
| 288 | C₆H₅CONHCH₂— | 3-CO₂C₂H₅ | foam (0.375 H₂O) | 65.02 (65.14 | 7.67 7.67 | 5.43 5.84) |
| 289 | thien-2-yl-SO₂NH—CH₂— | 3-CO₂C₂H₅ | foam (0.375 H₂O) | 52.91 (52.97 | 6.39 6.72 | 5.28 5.39) |
| 290 | CH₃O—C₆H₄—SO₂NHCH₂— | 3-CO₂C₂H₅ | foam | 58.24 (57.97 | 7.08 7.11 | 5.22 5.20) |
| 291 | ClCH₂CH₂— | 3-CO₂C₂H₅ | | | | |
| 292 | CH₃O(CH₂)₂OCH₂— | 3-CO₂C₂H₅ | | 62.19 (61.80 | 9.00 8.72 | 3.32 3.28) |
| 293 | CH₃O(CH₂)₂OCH₂— | 3-CO₂CH₂C₆H₅ | | 67.55 (68.23 | 8.71 8.68 | 2.73 2.57) |
| 294 | tetrahydrofuran-3-yl | 3-CO₂C₂H₅ | | 64.07 (64.52 | 8.77 8.62 | 3.79 3.42) |
| 295 | CH₃—C≡C—CH₂— | 3-CO₂C₂H₅ | foam (0.5 H₂O) | 65.80 (65.97 | 8.35 8.56 | 3.80 3.50) |
| 296 | CH₃—C≡C—CH₂— | 3-CO₂CH₂C₆H₅ | glass (0.6 H₂O) | 69.86 (69.83 | 7.55 7.86 | 3.25 3.02) |
| 297 | cyclohexyl | 3-CO₂C₂H₅ | foam | 68.00 (68.71 | 8.89 8.89 | 3.43 3.34) |
| 298 | cyclopentyl | 3-CO₂C₂H₅ | oil | 67.25 (67.78 | 9.01 9.15 | 3.27 3.43) |
| 299 | C₆H₅CH₂O(CH₂)₄— | 3-CO₂C₂H₅ | oil | Rf. 0.18 (silica; CH₂Cl₂, ether 1:1) | | |
| 300 | CH₂=CH—CH₂— | 3-CO₂C₂H₅ | oil | 66.08 (66.46 | 8.76 8.76 | 3.56 3.69) |
| 301 | tetrahydrofuran-3-yl | 4-CO₂CH₂C₆H₅ | gum | 68.05 (68.76 | 7.56 7.91 | 3.08 2.97) |
| 302 | 3-(CH₃NHCO)C₆H₄—CH₂— | 4-CO₂C₂H₅ | 0.125 CH₂Cl₂ | 65.76 (65.52 | 8.07 7.75 | 5.62 5.64) |

-continued

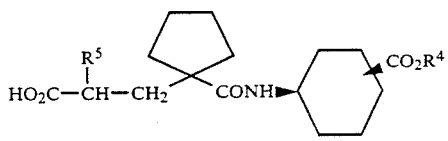

| Example No. | R⁵ | —CO₂R⁴ | Isolated Form | Analysis % (Theoretical in brackets) C | H | N |
|---|---|---|---|---|---|---|
| 303 | (tetrahydrofuranyl) | 4-CO₂C₂H₅ | gum | | | |
| 304 | (1,3-dioxepanyl) | 4-CO₂C₂H₅ | gum | Rf 0.6 (silica; (CH₂Cl₂, CH₃OH, CH₃CO₂H, 80:20:1) | | |
| 305 | CH₃OCH₂CH— \| CH₃ | 4-CO₂C₂H₅ | gum | Rf 0.65 (silica; (CH₂Cl₂, CH₃OH, CH₃CO₂H, 90:10:1) | | |
| 306 | CH₃(CH₂)₃CO₂(CH₂)₄— | 4-CO₂CH₂C₆H₅ | (0.25 H₂O) | 68.35 (68.35 | 8.81 8.51 | 2.70 2.49) |
| 307 | C₆H₅CH₂— | 4-CO₂CH₂C₆H₅ | | Rf 0.5 (silica; diethyl ether) | | |
| 308 | (cyclopropyl)—CH₂— | 3-CO₂C₂H₅ | | 66.70 (67.14 | 9.08 8.96 | 3.41 3.56) |

⁽¹⁾Using ester of Example 214

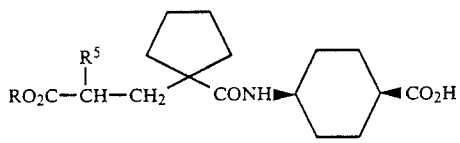

| Example No. | R⁵ | R | Isolated Form | Analysis % (Theoretical in Brackets) C | H | N |
|---|---|---|---|---|---|---|
| 309 | CH₃O(CH₂)₂— | C₆H₅CH₂— | gum (0.5 H₂O) | 66.53 (66.60 | 8.03 8.38 | 2.98 2.99) |
| 310 | CH₃CH₂CH₂— | C₆H₅CH₂— | (0.5 H₂O) | 69.13 (69.00 | 8.37 8.46 | 2.86 3.10) |
| 311 | CH₃C≡CCH₂— | C₂H₅— | | 66.87 (67.49 | 8.75 8.49 | 3.56 3.58) |
| 312 | CH₃C≡CCH₂— | C₆H₅CH₂— | solid m.p. 107–10° C. (0.5 H₂O) | 70.28 (70.10 | 7.74 7.85 | 3.03 3.03) |
| 313 | CH₂=CHCH₂— | C₂H₅— | solid m.p. 111–113° C. | 66.20 (66.46 | 8.78 8.76 | 3.49 3.69) |
| 314 | (cyclohexenyl)— | C₂H₅— | foam (0.75 H₂O) | 66.62 (66.56 | 8.87 8.96 | 3.32) 3.23) |

EXAMPLE 315

3-{1-[(cis-4-Carboxy-cyclohexyl)carbamoyl]cyclopentyl}-2-(methoxymethyl)propanoic acid 3-{1-[(cis-4-Benzyloxycarbonyl-cyclohexyl)carbamoyl]cyclopentyl}-2-(methoxymethyl)propanoic acid (390 mg, 0.88 mmole) was dissolved in tetrahydrofuran (25 ml) and water (10 ml) and was stirred with 5% palladium on carbon catalyst (100 mg) under an atmosphere of hydrogen at 50 p.s.i. (3.45 bar) for 3.5 hours. The catalyst was removed by filtration and the solvent evaporated to give a yellow gum. The residue was taken up in ethyl acetate (50 ml), and extracted into saturated sodium hydrogen carbonate solution (3×20 ml). The aqueous layer was separated, acidified with 2N hydrochloric acid and extracted with ethyl acetate (2×50 ml). The organic layer was separated, dried over magnesium sulphate, the solvent evaporated and the residue azeotroped with dichloromethane to give the title products as a colourless foam (264 mg, 85%). Found: C,59.02; H,7.89; N,3.73. $C_{18}H_{29}NO_6.0.15$ $CH_2Cl_2$ requires C,59.21; H,8.02; N,3.80%.

EXAMPLES 316–321

The following Examples were prepared by the procedure of Example 315 starting with the appropriate ester. The products are cis-3- and cis-4- cyclohexane carboxylic acids.

EXAMPLE 322

3-{1-[(cis-4-Ethoxycarbonyl-cyclohexyl)carbamoyl]cyclopentyl}-2-(cyclohexyl)propanoic acid 3-{1-[(cis-4-Ethoxycarbonyl-cyclohexyl)carbamoyl]cyclopentyl}-2-(cyclohex-2-enyl)propanoic acid (185 mg, 0.441 mmol) was dissolved in absolute ethanol (50 ml) and hydrogenated at 50 p.s.i. (3.45 bar) over 5% palladium on charcoal (10 mg) as catalyst. The solution was filtered and the solvent evaporated to give the title compound as a colourless gum (180 mg, 97%). Found: C,65.56; H,9.05; N,3.31. $C_{24}H_{39}NO_5.H_2O$ requires C,65.57; H,9.39; N,3.18%.

EXAMPLE 323

3-{1-[(cis-4-Carboxy-cyclohexyl)carbamoyl]cyclopentyl}-2-(2-ethoxyethyl)propanoic acid 3-{1-[(cis-4-Benzyloxycarbonyl-cyclohexyl)carbamoyl]cyclopentyl}-2-(2-ethoxyethyl)propanoic acid (225 mg, 0.476 mmole) was dissolved in 1,4-dioxan (20 ml), ethanol (4 ml) and water (6 ml) and was treated with 1N sodium hydroxide solution (2.4 ml, 2.4 mmole). After 20 hours at room temperature, the solution was evaporated to half volume, diluted with water (20 ml) and washed with diethyl ether. The aqueous layer was separated, acidified with 2N hydrochloric acid and extracted with ethyl acetate (3×20 ml). The ethyl acetate layer was separated, dried over magnesium sulphate and the solvent evaporated to give the title product as a colourless foam (161 mg, 88%). Found: C,61.89; H,8.29; N,3.62. $C_{20}H_{33}NO_6.0.2$ $H_2O$ requires C,62.06; H,8.69; N,3.62%.

EXAMPLES 324–381

The following Examples were prepared by the procedure of Example 323 starting with the appropriate ester:

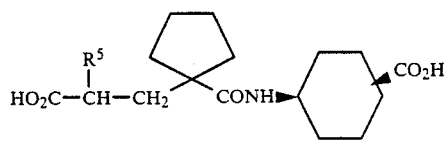

| Example No. | $R^5$ | —$CO_2H$ | Isolated Form | C | H | N |
|---|---|---|---|---|---|---|
| 316 | (tetrahydrofuran-2-yl)-CH₂— | 4-$CO_2H$ | foam (0.25 $H_2O$) | 62.99 (63.05 | 8.53 8.44 | 3.44 3.50) |
| 317 | (N-methyl-cyclohexylamino)-CH₂— | 3-$CO_2H$ | foam (hydrochloride) | 61.37 (60.94 | 8.92 8.74 | 5.94 5.91) |
| 318 | (phthalimido)-CH₂— | 4-$CO_2H$ | foam (1.25 $H_2O$) | 62.68 (62.68 | 7.21 7.26 | 5.34 5.84) |
| 319 | $CH_3O(CH_2)_2OCH_2—$ | 3-$CO_2H$ | foam (0.5 $H_2O$) | 59.05 (58.80 | 8.33 8.39 | 3.51 3.43) |
| 320 | $CH_3(CH_2)_3CO_2(CH_2)_4—$ | 4-$CO_2H$ | foam | 64.59 (64.20 | 8.50 8.84 | 3.05 3.00) |
| 321 | $C_6H_5CH_2—$ | 4-$CO_2H$ | Solid m.p. 164–165° C. (0.75 $H_2O$) | 66.61 (66.56 | 7.56 7.90 | 3.57 3.38) |

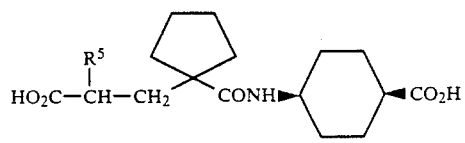

| Example No. | R⁵ | Isolated Form | C | H | N |
|---|---|---|---|---|---|
| | | | \multicolumn{3}{c}{Analysis % (Theoretical in brackets)} | | |
| 324 | CH₃O(CH₂)₃— | foam (0.3 H₂O) | 61.78 (61.77 | 8.50 8.71 | 3.51 3.60) |
| 325 | CH₃O(CH₂)₂OCH₂— | white solid m.p. 177-9° C. | 60.23 (60.13 | 8.46 8.33 | 3.31 3.51) |
| 326 | 2-pyridyl-CH₂— | foam (0.75 H₂O) | 63.43 (63.52 | 7.32 7.63 | 6.47 6.74) |
| 327 | pyrimidinyl-CH₂— | foam (0.7 H₂O) | 60.90 (60.70 | 7.51 7.36 | 10.30 10.11) |
| 328 | CH₂=CH—CH₂— | foam (0.25 H₂O) | 64.14 (64.11 | 8.52 8.35 | 4.13 3.94) |
| 329 | CH₃COCH₂— | foam (0.12 CH₂Cl₂) | 60.77 (60.81 | 7.99 7.81 | 3.31 3.71) |
| 330 | C₆H₅CH₂—N(pyrrolyl)—CH₂— | foam (3 H₂O) | 60.71 (60.54 | 6.65 7.72 | 7.88 7.85) |
| 331 | 4-pyridyl-CH₂— | foam (0.5 H₂O) (0.3 CH₂Cl₂) | 60.67 (60.99 | 7.05 7.26 | 6.33 6.37) |
| 332 | CH₃C≡C—CH₂— | solid, m.p. 196-8° C. | 65.98 (66.09 | 8.13 8.04 | 3.98 3.85) |
| 333 | cyclohexyl | solid (0.2 H₂O) | 66.85 (66.88 | 8.51 8.52 | 3.43 3.55) |
| 334 | C₆H₅—CH(OCH₃)— | solid, m.p. 167-8° C. | 66.75 (66.80 | 7.77 7.71 | 3.10 3.25) |
| 335 | C₆H₅CH₂—N(CH₃)—CH₂— | foam (0.5 H₂O) | 66.65 (66.20 | 7.97 8.22 | 7.09 6.18) |
| 336 | CH₃O(CH₂)₂NHCOCH₂— | foam (0.5 H₂O, 0.1 CH₂Cl₂) | 57.38 (57.08 | 8.15 7.99 | 5.94 6.31) |
| 337 | morpholino-NCOCH₂— | foam (0.3 CH₂Cl₂) | 58.05 (57.73 | 8.04 7.51 | 5.60 6.04) |
| 338 | CH₃SO₂(CH₂)₂— | foam (1.5 H₂O) | 51.37 (51.34 | 7.55 7.21 | 2.72 3.15) |
| 339 | HO(CH₂)₄—⁽¹⁾ | foam (0.5 H₂O) | 61.05 (61.20 | 8.57 8.73 | 3.46 3.57) |
| 340 | C₆H₅CH₂OCONH— | white solid m.p. 158-162° C. (0.1 CH₂Cl₂ 0.25 H₂O) | 61.16 (61.13 | 7.07 6.96 | 5.87 5.92) |
| 341 | C₆H₅SO₂NH— | white solid m.p. 211-213° C. | 56.86 (56.63 | 6.50 6.48 | 5.99 6.01) |
| 342 | C₆H₅CH₂CONH— | white solid m.p. 177-180° C. | 65.22 (64.84 | 7.38 7.26 | 6.21 6.30) |
| 343 | C₆H₅CH₂NHCONH— | white solid | 59.98 | 7.48 | 8.55 |

-continued

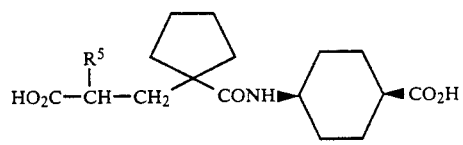

| Example No. | R⁵ | Isolated Form | Analysis % (Theoretical in brackets) C | H | N |
|---|---|---|---|---|---|
| | | m.p. 176–180° C. (1.25 H₂O) | (59.80 | 7.42 | 8.72) |
| 344 | CH₃(CH₂)₂SO₂NH— | white solid | 52.49 (52.76 | 7.57 7.46 | 6.29 6.48) |
| 345 | C₆H₅CH₂SO₂NH— | white solid m.p. 187–191° C. | 57.27 (57.48 | 6.94 6.71 | 5.66 5.83) |
| 346 | C₆H₅CH₂OCONCH₂— (with CH₂CH₃ branch) | foam | 64.48 (64.52 | 7.65 7.62 | 5.49 5.58) |
| 347 | 2-furyl-CONCH₂— (with CH₂CH₃ branch) | foam (0.125 CH₂Cl₂) | 61.48 (61.24 | 7.31 7.30 | 5.98 5.92) |
| 348 | CH₃SO₂NCH₂— (with CH₂CH₃ branch) | foam (0.2 CH₃CO₂C₂H₅) | 53.40 (53.79 | 7.69 7.67 | 5.86 6.27) |
| 349 | C₆H₅CH₂OCONH—CHCH₂— (CH₃) Diastereomer A | foam (0.1 CH₂Cl₂ 0.5 H₂O) | 62.69 (62.58 | 7.58 7.60 | 5.11 5.39) |
| 350 | C₆H₅CH₂OCONH—CHCH₂— (CH₃) Diastereomer B | foam (0.6 H₂O) | 62.88 (63.16 | 7.45 7.70 | 5.26 5.46) |
| 351 | CH₃OCONH—CHCH₂— (CH₃) Diastereomer A | foam (0.25 CH₂Cl₂) | 57.06 (57.00 | 8.23 7.77 | 5.81 6.26) |
| 352 | CH₃OCONH—CHCH₂— (CH₃) Diastereomer B | foam (0.25 CH₂Cl₂) | 57.09 (57.00 | 7.89 7.77 | 6.15 6.26) |
| 353 | C₆H₅CH₂OCONH—CH— (CH₂CH₃) | foam (0.1 CH₃CO₂C₂H₅, 1.0 H₂O) | 62.48 (62.16 | 7.56 7.77 | 5.06 5.29) |
| 354 | C₆H₅CONHCH₂— | solid m.p. 89–93° C. (0.16 CH₂Cl₂ 0.08 CH₃CO₂C₂H₅ 0.4 H₂O) | 62.05 (62.18 | 7.38 7.20 | 6.85 5.92) |
| 355 | CH₃CONHCH₂— | solid m.p. 51–53° C. (0.1 CH₂Cl₂ 0.5 CH₃CO₂H) | 57.17 (57.34 | 8.24 7.71 | 6.98 6.61) |
| 356 | CH₃(CH₂)₂SO₂NHCH₂— | foam (0.1 CH₃CO₂C₂H₅ 0.5 H₂O) | 52.73 (52.76 | 8.01 7.77 | 6.13 6.03) |
| 357 | C₆H₅SO₂NHCH₂— | foam (1.0 H₂O) | 55.70 (55.41 | 6.77 6.87 | 5.51 5.62) |
| 358 | CH₃CH₂SO₂CH₂— | foam (0.2 CH₃CO₂C₂H₅) | 54.44 (54.65 | 7.68 7.55 | 3.14 3.22) |
| 359 | CF₃SO₂NH— | foam (0.375 CH₃CO₂C₂H₅) | 45.78 (45.69 | 6.15 5.96 | 5.58 5.76) |
| 360 | tetrahydrofuran-3-yl | foam | 62.59 (62.97 | 8.01 8.19 | 3.71 3.62) |
| 361 | 3-(CH₃NHCO)-C₆H₄-CH₂— | foam | 63.17 (63.21 | 7.31 7.25 | 5.47 5.84) |

-continued

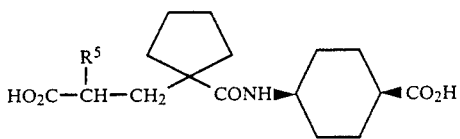

| Example No. | R⁵ | Isolated Form | Analysis % (Theoretical in brackets) C | H | N |
|---|---|---|---|---|---|
| 362 | (tetrahydrofuran-2-yl) | foam (0.25 CH₃CO₂H) | 61.90 (62.10 | 8.16 8.14 | 3.38 3.53) |
| 363 | (1,3-dioxepan-5-yl) | foam (H₂O, 0.15 CH₃CO₂C₂H₅) | 58.38 (58.88 | 8.00 8.35 | 3.07 3.18) |
| 364 | CH₃OCH₂CH(CH₃)— | foam (0.25 H₂O) | 62.01 (61.91 | 9.11 8.71 | 3.39 3.61) |

(1)using ester of Example 261

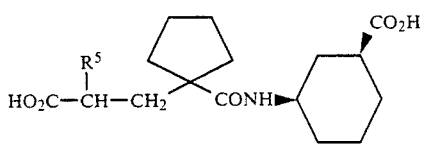

| Example No. | R⁵ | Isolated Form | Analysis % (Theoretical in brackets) C | H | N |
|---|---|---|---|---|---|
| 365 | NH₂CH₂— | solid m.p. 197–200° C. (0.5 H₂O) | 58.65 (58.43 | 8.53 8.37 | 7.87 8.02) |
| 366 | CF₃SO₂NHCH₂— | solid m.p. 107–109° C. | 45.73 (45.75 | 5.62 5.76 | 5.69 5.93) |
| 367 | CH₃(CH₂)₂SO₂NH— | solid m.p. 163–165° C. | 52.90 (52.76 | 7.72 7.46 | 6.26 6.48) |
| 368 | C₆H₅SO₂NHCH₂— | foam (1.0 H₂O; 0.5 CH₃CO₂C₂H₅) | 55.74 (55.33 | 6.71 7.06 | 5.61 5.16) |
| 369 | C₆H₅CONHCH₂— | foam (0.5 H₂O) | 63.58 (63.56 | 7.49 7.33 | 5.71 6.18) |
| 370 | cyclopropyl-CH₂— | solid | 64.38 (65.72 | 8.88 8.55 | 3.58 3.83) |
| 371 | (2,4-dimethylthiazol-5-yl)-SO₂NHCH₂— | foam (0.25 CH₂Cl₂) | 49.56 (49.77 | 6.39 6.29 | 7.45 7.83) |
| 372 | (3,5-dimethylisoxazol-4-yl)-SO₂NHCH₂— | foam (0.25 CH₂Cl₂) | 51.09 (51.31 | 6.40 6.48 | 7.88 8.08) |
| 373 | CH₃CH=CHCH₂— | gum | 65.86 (65.73 | 8.52 8.55 | 3.84 3.83) |
| 374 | (tetrahydrofuran-3-yl) | foam (0.5 H₂O) | 61.24 (61.52 | 8.22 8.26 | 3.40 3.58) |

-continued

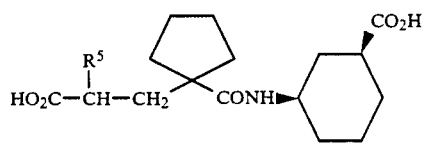

| Example No. | $R^5$ | Isolated Form | Analysis % (Theoretical in brackets) C | H | N |
| --- | --- | --- | --- | --- | --- |
| 375 | $CH_3C{\equiv}CCH_2-$ | foam (0.5 $H_2O$, 0.1 $CH_2Cl_2$, 0.1 $CH_3CO_2C_2H_5$) | 63.13 (63.17 | 8.37 8.02 | 4.02 3.67) |
| 376 | cyclohexenyl- | foam (0.2 $CH_2Cl_2$) | 65.56 (65.75 | 8.42 8.30 | 3.52 3.45) |
| 377 | cyclohexyl- | foam (0.5 $H_2O$) | 66.24 (66.30 | 8.92 9.10 | 3.14 3.51) |
| 378 | cyclopentyl- | foam (0.06 $CH_2Cl_2$) | 64.89 (65.78 | 8.51 8.68 | 3.53 3.64) |
| 379 | $CH_2{=}CHCH_2-$ | foam | 63.95 (64.11 | 8.17 8.35 | 3.99 3.94) |
| 380 | 2-thienyl-$SO_2NHCH_2-$ | foam (0.5 $H_2O$) | 50.76 (50.89 | 6.28 6.31 | 5.46 5.65) |
| 381 | $CH_3O$-phenyl-$SO_2NHCH_2-$ | foam | 56.69 (56.46 | 6.95 6.71 | 5.10 5.49) |

EXAMPLE 382

3-{1-[(cis-3-Ethoxycarbonyl-cyclohexyl)carbamoyl]cyclopentyl}-2-(4-hydroxybutyl)propanoic acid, calcium salt 3-{1-[(cis-3-Ethoxycarbonyl-cyclohexyl)carbamoyl]-cyclopentyl}-2-(4-benzyloxybutyl)propanoic acid (742 mg, 1.48 mmole) was dissolved in absolute ethanol (10 ml) containing 10% palladium on carbon (74 mg) as catalyst, and the mixture hydrogenated at 50 p.s.i. (3.45 bar) for 20 hours at room temperature. Further catalyst (70 mg) was added and the mixture hydrogenated for a further 4.5 hours under the same conditions. The solution was filtered, the solvent evaporated under vacuum and the residue azeotroped six times with dichloromethane. The crude product was taken up in ethyl acetate (50 ml) and extracted into saturated sodium bicarbonate solution (2×50 ml). The aqueous extract was acidified to pH 1 with 2N hydrochloric acid and extracted with ethyl acetate (3×50 ml). The combined organic extracts were dried (MgSO4) and the solvent evaporated to yield the title acid as a colourless foam (556 mg, 92%). This product was dissolved in ethanol (15 ml) and a suspension of calcium hydroxide (71 mg) in water (3 ml) was added. The mixture was stirred at 30° C. for 45 minutes then filtered and evaporated. The residue was dissolved in dichloromethane, dried over MgSO4, filtered and the solvent evaporated. The residue was triturated with diethyl ether and dried under vacuum at 70° C. for 2 days to give the calcium salt as a white solid, m.p. 116°–120° C. Found: C,61.30; H,8.32; N,3.61. $C_{44}H_{72}N_2O_{12}Ca$ requires C,61.37; H,8.43; N,3.25%.

EXAMPLE 383

3-{[1-(cis-5-Carboxy-cis-2-methyl-cyclohexyl)carbamoyl]cyclopentyl}-2-(2-methoxyethyl)propanoic acid 3-{1-[(cis-5-Methoxycarbonyl-cis-2-methyl-cyclohexyl)carbamoyl]cyclopentyl}-2-(2-methoxyethyl)propanoic acid benzyl ester (630 mg, 1.29 mmole) in ethanol (20 ml) and water (15 ml) was hydrogenated at room temperature for three hours over 5% palladium on charcoal catalyst (200 mg) at 50 p.s.i. (3.45 bar) pressure. The suspension was filtered through a short Avicel column and the solvent evaporated under reduced pressure. The mono-ester (490 mg), which was obtained as a gum was dissolved in 1N sodium hydroxide (5 ml) and the solution washed with ether. The ether washings were extracted with water and the combined aqueous solutions evaporated to 5 ml at 40° C., under reduced pressure and then allowed to stand at room temperature overnight.

The resulting clear solution was acidified with 2N hydrochloric acid and extracted with methylene chloride. The organic extract was washed with water, dried (MgSO4), and evaporated to give the required diacid as a foam (411 mg, 83%). Found: C,61.95; H,8.58; N,3.69. $C_{20}H_{33}NO_6, 0.25$ $H_2O$ requires C,61.91; H,8.70; N,3.61%.

EXAMPLES 384-393

The following Examples were prepared by the procedure of Example 383 starting with the appropriate ester of formula (V) wherein $R^{13}$ is benzyl and $R^{14}$ is methyl or ethyl.

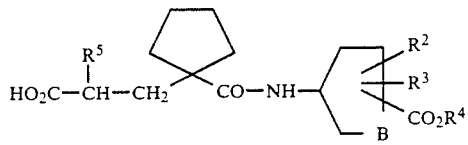

| Example No. | $R^5$ | B (with $R^2$, $R^3$, $CO_2R^4$) | Analysis % (Theoretical in brackets) C | H | N |
|---|---|---|---|---|---|
| 384 | $CH_3(CH_2)_2-$ | cyclohexyl: $CO_2H$, $C_2H_5$ | 66.06 (66.11 | 9.18 9.25 | 3.62 3.67) |
| 385 | $CH_3(CH_2)_2-$ | cyclohexyl: $CO_2H$, $CH_3$ | 65.36 (65.37 | 9.09 9.05 | 3.78 3.81) |
| 386 | $CH_3(CH_2)_2-$ | cyclohexyl: $CO_2H$, $CH_3$ | 65.10 (65.37 | 9.14 9.05 | 3.55 3.81) |
| 387 | $CH_3O-(CH_2)_2-$ | cyclohexyl: $CO_2H$, $C_2H_5$ | 62.02 (62.04 | 8.80 8.73 | 3.38 3.45)[1] |
| 388 | $CH_3O-(CH_2)_2-$ | cyclopentyl: $CO_2H$, $(CH_2)_2CH_3$ | 63.21 (63.45 | 9.00 8.87 | 3.35 3.52) |
| 389 | $CH_3O-(CH_2)_2-$ | cyclopentyl: $CO_2H$, $(CH_2)_2CH_3$, HO | 60.03 (59.68 | 8.78 8.59 | 3.16 3.32) |
| 390 | $CH_3S(CH_2)_2$ | cyclohexyl: $CO_2H$ | 57.89 (57.85 | 8.30 8.18 | 3.16 3.55) |

[1] 0.5 hydrate.

-continued

[Structure: HO₂C—CH(R⁵)—CH₂—[cyclopentyl]—CO—NH—[substituted ring with R², R³, CO₂R⁴, B]]

| Example No. | R⁵ | [ring with R², R³, CO₂R⁴, B] | Analysis % (Theoretical in brackets) | | |
|---|---|---|---|---|---|
| | | | C | H | N |
| 391 | $CH_3O(CH_2)_2-$ | 4-CO₂H-cyclohexyl (HO-substituted) | 57.23 (57.23 | 8.09 8.10 | 3.35 3.50)[1] |
| 392 | $CH_3(CH_2)_2-$ | 4-CO₂H-cyclohexyl (C₂H₅-substituted) | 64.86 (66.11 | 9.21 9.25 | 3.37 3.67) |
| 393 | $HO(CH_2)_4-$ | 4-CO₂H-cyclohexyl | 60.41 (60.37 | 8.39 8.76 | 3.30 3.52)[2] |

[1] hemihydrate
[2] 0.8 H₂O

EXAMPLE 394

2-(4-Aminobutyl)-3-{1-[cis-4-carboxy-cyclohexyl)carbamoyl]cyclopentyl}propanoic acid t-butyl ester 2-(4-Azidobutyl)-3-{1-[(cis-4-benzyloxycarbonylcyclohexyl)carbamoyl]cyclopentyl}propanoic acid t-butyl ester (2.73 g, 5.11 mmole) in tetrahydrofuran (150 ml) and water (75 ml) was stirred with 5% palladium on carbon catalyst (250 mg) at room temperature under hydrogen at 50 p.s.i. (3.45 bar) for 2.5 hours. After this time the catalyst was removed by filtration, the solvent evaporated and the residue triturated with diethyl ether (3×50 ml) to give the title product as a colourless solid (1.45 g, 65%) m.p. 186°-90° C. (with decomposition). Found: C,64.80; H,9.69; N,5.92. $C_{24}H_{42}N_2O_5$,0.33 $H_2O$ requires C,64.83; H,9.67; N,6.30%.

EXAMPLE 395

2-(4-Acetamidobutyl)-3-{1-[(cis-4-carboxycyclohexyl)carbamoyl]cyclopentyl}propanoic acid t-butyl ester 2-(4-Aminobutyl)-3-{1-[(cis-4-carboxy-cyclohexyl)carbamoyl]cyclopentyl}propanoic acid t-butyl ester (280 mg, 0.64 mmole) was dissolved in dichloromethane (30 ml) and treated with triethylamine (152 mg, 1.51 mmole) and acetic anhydride (78 mg, 0.76 mmole). After 20 minutes at room temperature the solvent was evaporated and the residue was dissolved in ethyl acetate (50 ml), washed with 1N hydrochloric acid (50 ml) and water (2×50 ml). The organic layer was separated, dried over magnesium sulphate and evaporated to give a colourless foam. Chromatography on silica gel eluting with a mixture of methanol and dichloromethane (1:19-1:4 by volume) and evaporation of the appropriate fractions gave the title product as a colourless foam (273 mg, 89%). Found: C,60.09; H,8.68; N,4.99. $C_{26}H_{44}N_2O_5$,0.5 $CH_2Cl_2$ requires, C,60.10; H,8.57; N,5.27%.

EXAMPLE 396

2-(4-Aminobutyl)-3-{1-[(cis-4-carboxy-cyclohexyl)carbamoyl]cyclopentyl}propanoic acid 2-(4-Aminobutyl)-3-{1-[(cis-4-carboxy-cyclohexyl)carbamoyl]cyclopentyl}propanoic acid t-butyl ester (1.0 g, 2.28 mmole) was dissolved in trifluoroacetic acid (8 ml) at 0° C. After 3 days at this temperature the solvent was evaporated and the residue azeotroped with dichloromethane (3×50 ml). The resulting brown oil was purified by passage through ion exchange resin (Bio-Rad AG 50W-X8, 30 ml) eluting with pyridine and water (3:100 by volume), and the appropriate fractions evaporated to give the title product as a colourless foam (700 mg, 80%). Found: C,61.97; H,9.08; N,7.69. $C_{20}H_{34}N_2O_5$, 0.1 $C_5H_5N$, 0.3 $H_2O$ requires C,62.21; H,8.94; N,7.43%.

EXAMPLE 397

2-(4-Acetamidobutyl)-3-{1-[(cis-4-carboxy-cyclohexyl)carbamoyl]cyclopentyl}propanoic acid 2-(4-Acetamidobutyl)-3-{1-[(cis-4-carboxy-cyclohexyl)carbamoyl]cyclopentyl}propanoic acid t-butyl ester (270 mg, 0.58 mmole) was dissolved in trifluoroacetic acid (4 ml) at 0° C. After 20 hours the solvent was evaporated and the resulting oil azeotroped with dichloromethane (3×20 ml). The oil was taken up in ethyl acetate (20 ml) and washed with water (7×20 ml) until the washings were neutral. The organic layer was separated, dried over magnesium sulphate, and evaporated. The residue was dissolved in saturated sodium carbonate solution (20 ml) washed with ethyl acetate (2×20 ml), acidified with 2N hydrochloric acid and then extracted with ethyl acetate (3×20 ml). The organic layer was separated, dried over magnesium sulphate and evaporated. The residue was azeotroped with tetrahydrofuran to give the title product as a colourless foam (110 mg, 45%). Found: C,62.58; H,8.71; N,5.27. $C_{22}H_{36}N_2O_5 \cdot C_4H_8O$ requires C,62.88; H,8.93; N,5.64%.

EXAMPLE 398

3-{1-[(cis-4-Carboxycyclohexyl)carbamoyl]cyclopentyl}-2-(imidazo-2-ylmethyl)propanoic acid 3-{1-[(cis-4-Carboxycyclohexyl)carbamoyl]cyclopentyl}-2-(1-benzyl-imidazol-2-yl-methyl)propanoic acid (Example 330) (800 mg, 1.5 mmole) in aqueous ethanol (80 ml, 1:1 by volume) was hydrogenated for seven hours at 30 p.s.i. (2 bar) pressure over 5% palladium on charcoal (400 mg). The catalyst was removed by filtration and the solvent evaporated under reduced pressure. The product was dissolved in 1N sodium hydroxide (6 ml), and taken up on cation exchange resin (Dow, AG 50W-X8). Elution with aqueous pyridine, increasing in concentration from 0 to 5%, and evaporation of the eluent gave the title diacid as a white foam (270 mg, 34%). Found: C,58.76; H,7.50; N,10.18. $C_{20}H_{29}N_3O_5 \cdot H_2O$ requires C,58.66; H,7.63; N,10.26%.

EXAMPLE 399

3-{1-[(cis-4-Carboxycyclohexyl-carbamoyl]cyclopentyl}-2-[2-(2-thiazolylcarbamoyl)ethyl]propanoic acid 3-{1-[(cis-4-Benzyloxycarbonyl-cyclohexyl)-carbamoyl]cyclopentyl}-2-[2-(2-thiazolylcarbamoyl)ethyl]propanoic acid benzyl ester (120 mg, 0.18 mmole) and anisole (121 mg, 1.1 mmole) were dissolved in dichloromethane (2.5 ml). A solution of aluminium chloride (149 mg, 1.1 mmole) in nitromethane (2.5 ml) was added at 0° C. under nitrogen. After stirring for 16 hours at room temperature the mixture was poured into saturated aqueous sodium hydrogen carbonate, filtered and the aqueous filtrate acidified with dilute hydrochloric acid. The solution was saturated with solid sodium chloride and the product extracted into ethyl acetate, dried ($Na_2SO_4$) and the solvent evaporated under vacuum to yield the title compound (50 mg, 58%). Rf. 0.4 (silica; $CH_2Cl_2$, $CH_3OH$, $CH_3CO_2H$, 90:10:1).

EXAMPLE 400

2-Amino-3-{1-[cis-4-carboxy-cyclohexyl)carbamoyl]-cyclopentyl}propanoic acid

2-Benzyloxycarbonylamino-3-{1-[cis-4-carboxycyclohexyl)carbamoyl]cyclopentyl}-propanoic acid (260 mg, 0.56 mmole) was dissolved in a mixture of ethanol (20 ml) and water (2 ml) and hydrogenated at 30 p.s.i. (2 bar) and room temperature for 3 hours. Filtration through Arbacell and evaporation of the solvent gave crude product which was dissolved in methanol, filtered and the filtrate evaporated. The residue was washed with dichloromethane and dried under vacuum to give the title compound as a cream-solid (33 mg, 18%). Found: C,55.72; H,8.00; N,7.65. $C_{16}H_{26}N_2O_5 \cdot 0.2$ $CH_3OH \cdot 1.0$ $H_2O$ requires C,55.46; H,8.27; N,7.99%.

EXAMPLE 401

3-{1-[(cis-4-Carboxy-cyclohexyl)carbamoyl]-cyclopentyl}-2-[2-(hydroxy)ethoxymethyl]propanoic acid 3-{1-[(cis-4-Carboxy-cyclohexyl)carbamoyl]-cyclopentyl}-2-[2-(methoxy)ethoxymethyl]propanoic acid (0.80 g, 2 mmole) was dissolved in dry dichloromethane (15 ml) and treated with trimethylsilyl iodide (1.4 ml, 10 mmole) at 0° C. under nitrogen. After 6 hours at 0° C., the reaction was poured into ice-cold dilute sodium hydrogen carbonate and washed with dichloromethane. The aqueous phase was acidified with concentrated hydrochloric acid and extracted with ethyl acetate (3×50 ml). The first extract contained starting material, the second and third extracts were combined, washed with dilute sodium thiosulphate, dried ($Na_2SO_4$) and evaporated to give an orange oil. The residue was azeotroped with dichloromethane and washed with dichloromethane to give the title compound as a glassy foam (0.22 g, 29%). Found: C,57.24; H,8.07; N,3.42. $C_{19}H_{31}NO_7 \cdot 0.1$ $CH_2Cl_2$ $0.25$ $H_2O$ requires C,57.58; H,8.02; N,3.52%.

EXAMPLE 402

3-{1-[(cis-4-Carboxycyclohexyl)carbamoyl]cyclopent-3-enyl}-2-propylpropanoic acid Hexamethyldisilane (1.78 g, 12.19 mmole) and iodine (2.8, 11.05 mmole) were heated at 65° C. with stirring under nitrogen for one hour. The mixture was cooled and cyclohexene (30 ml, 300 mmole) added followed by 3-{1-[(cis-4-benzyloxycarbonylcyclohexyl) carbamoyl]-cyclopent-3-enyl}-2-propylpropanoic acid benzyl ester (1.78 g, 3.35 mmole) in carbontetrachloride (30 ml) and the mixture was stirred at 65°-70° C., the progress of the reaction being followed by thin layer chromatography. After 18 hours trimethylsilyl iodide (2.0 g, 10.05 mmole) was added followed by a further addition (4.0 g, 20 mmole) 24 hours later. After a further 7 hours the mixture was cooled and poured onto a mixture of methylene chloride and water. The organic phase was washed with saturated brine and extracted with 0.1N sodium hydroxide. The alkaline extract was washed with diethyl ether, acidified to pH 1-2 with concentrated hydrochloric acid and extracted with methylene chloride. The organic extract was washed with saturated brine, dried ($MgSO_4$) and the solvent evaporated under vacuum to yield the title diacid as a yellow foam (1.05 g). Chromatography on silica gel, eluting with methylene chloride containing increasing proportions of methanol (1 to 5% by volume) gave the pure product as a pale yellow foam (650 mg, 55%). Found: C,62.69; H,8.11; N,3.99. $C_{19}H_{29}NO_5 \cdot 0.6$ $H_2O$ requires C,62.99; H,8.40; N,3.87%.

EXAMPLES 403-405

The following compounds were prepared from the appropriate dibenzyl ester following the procedure of Example 402.

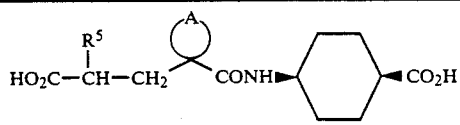

| Example No | R⁵ | A | Analysis % (Theoretical in brackets) | | |
|---|---|---|---|---|---|
| | | | C | H | N |
| 403 | $CH_3O(CH_2)_2$ | (cyclopropyl) | 61.40 (61.35 | 8.03 7.99 | 3.78 3.77)[1] |
| 404 | $CH_3O(CH_2)_2-$ | (cyclohexyl) | 63.15 (62.97 | 8.36 8.19 | 3.60 3.67) |
| 405 | HO—〔 〕—$CH_2-$ | (cyclopentyl) | 66.87 (61.09 | 7.20 7.47 | 2.65 3.09) |

[1] 0.25 $H_2O$.

EXAMPLE 406

3-{1-[(cis-4-Carboxycyclohexyl)carbamoyl]cyclopentyl}-2-(2-methoxyethoxymethyl)propanoic acid 1-(2,2-diethylbutyryloxy)ethyl ester (a) 3-{1-[cis-4-Benzyloxycarbonyl-cyclohexyl)carbamoyl]cyclopentyl}2-[(2-methoxyethoxymethyl]-propanoic acid (0.5 g, 1.02 mmole) was dissolved in a mixture of acetonitrile (20 ml) and water (10 ml). A solution of caesium carbonate (1.0 g) in water (10 ml) was added dropwise until the pH of the solution was about 8. The resulting caesium salt solution was stirred at room temperature for 15 minutes and evaporated to dryness under vacuum. The residue was freed from water by azeotroping with toluene (3×) then with acetonitrile (4×). The resulting pale yellow foam was dissolved in dry dimethylformamide (40 ml) and a solution of 1-(2,2-diethylbutyryloxy)chloroethane (232 mg, 1.12 mmole) in dimethylformamide (1 ml) was added and the mixture stirred at room temperature overnight. The solvent was evaporated under reduced pressure and traces of dimethylformamide removed by azeotroping with toluene. The residue was dissolved in ethyl acetate (20 ml) and washed with 2M hydrochloric acid (3×10 ml). The organic phase was dried over magnesium sulphate, the solvent evaporated under reduced pressure and the residue chromatographed on silica. Elution with a mixture of diethyl ether and dichloromethane (9:1) afforded the required diester as colourless gum (355 mg, 53%). Found: C, 67.53; H, 8.87; N, 2.23. $C_{37}H_{57}NO_9$ requires C,67.35; H,8.71; N,2.12%.

(b) The product from (a) above (318 mg, 0.482 mmole) was dissolved in a mixture of ethanol (27 ml) and water (3 ml) and hydrogenated at 50 p.s.i. (3.45 bar) over 10% palladium on charcoal catalyst (30 mg) for 4 hours. The reaction mixture was filtered and the solvent evaporated under vacuum. The residue was azeotroped with dichloromethane (4×50 ml) to afford the required compound as a white foam (275 mg, 100%). Found: C,63.60; H,9.22; N,2.46. $C_{30}H_{51}NO_9$ requires C,63.24; H,9.02; N,2.46%.

EXAMPLES 407–418

The following compounds were prepared by the procedure of Example 406 by reaction of the caesium salt with the appropriate chloro compound. The products were obtained as foams or gums:

$$CH_3OCH_2CH_2OCH_2\text{-CH-CH}_2\text{-}[cyclopentyl]\text{-CONH-}[cyclohexyl]\text{-}CO_2H$$
$R^{17}O_2C$

| Example No. | $R^{17}$ | Analysis % (Theoretical in brackets) | | |
|---|---|---|---|---|
| | | C | H | N |
| 407 | $(CH_3CH_2)_2CHCO_2CH_2-$ | 61.12 (61.46 | 9.04 8.59 | 2.53 2.65) |
| 408 | $(CH_3CH_2)_2CHCO_2CH-$<br>                   $CH_3$ | 61.92 (62.08 | 9.41 8.75 | 2.47 2.59) |
| 409 | 2,4-dimethylphenyl-$CO_2CH(CH_3)-$ | 64.63 (64.67 | 8.09 7.88 | 2.62 2.43) |
| 410 | diphenyl-$CH-O_2C-$ | 67.08 (66.98 | 7.25 7.11 | 2.04 2.30) |
| 411 | phenyl-$CO_2CH(CH_3)-$ | 62.41 (62.57 | 7.55 7.60 | 2.60 2.51) |
| 412 | $CH_3CH_2CO_2-CH-$<br>                   $CH(CH_3)_2$ | 60.96 (60.46 | 8.64 8.60 | 2.82 2.65) |
| 413 | 2,4,6-trimethylphenyl-$CO_2CH_2-$ | 64.54 (64.67 | 7.90 7.88 | 2.31 2.43) |
| 414 | 2,4,6-trimethylphenyl-$CO_2CH(CH_3)-$ | 63.68 (63.71 | 7.86 8.11 | 2.20 2.32)[1] |
| 415 | $(CH_3)_3CCO_2CH_2-$ | 60.42 (60.80 | 8.37 8.44 | 2.68 2.73) |
| 416 | phenyl-$(CH_2)_2-$ | 64.21 (64.47 | 8.05 8.31 | 2.66 2.69)[2] |
| 417 | phenyl-$(CH_2)_3-$ | 66.86 (67.28 | 8.37 8.37 | 2.65 2.71) |

-continued

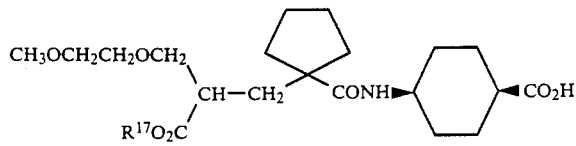

| Example No. | R[17] | Analysis % (Theoretical in brackets) | | |
|---|---|---|---|---|
| | | C | H | N |
| 418 | CF₃CH₂— | 54.80 (54.87 | 7.25 7.12 | 2.57 2.91) |

[1] 0.75 Hydrate
[2] Monohydrate

EXAMPLE 419

3-{1-[(cis-4-Carboxycyclohexyl)carbamoyl]cyclopentyl}-2-(2-methoxyethoxymethyl)propanoic acid 1-naphthyl ester hemihydrate (a) 2-(2-Methoxyethoxymethyl)-3-[(1-phenacyloxycarbonyl)cyclopentyl]propanoic acid t-butyl ester Anhydrous potassium carbonate (18.0 g, 0.130 mole) was added to a stirred solution of phenacyl bromide (13.0 g, 0.0653 mole) and 3-(1-carboxycyclopentyl)-2-(2-methoxyethoxymethyl)propanoic acid t-butyl ester (21.34 g, 0.0645 mole) in dry dimethylformamide (100 ml). The resulting suspension was stirred at room temperature for 18 hours, then the bulk of the solvent was removed under vacuum and the residue partitioned between ethyl acetate (150 ml) and water (100 ml). The organic phase was separated, washed successively with water (50 ml), 1N hydrochloric acid (3×50 ml), and saturated aqueous sodium bicarbonate solution (50 ml), then dried over anhydrous magnesium sulphate. The solvent was removed by evaporation under vacuum to afford an oil which was purified by chromatography on silica gel eluting with a hexane-ethyl acetate gradient. The appropriate fractions were combined and the solvent evaporated under vacuum to give the title compound as a colourless oil (16.0 g, 55%), Rf (silica) 0.71 (ethyl acetate/toluene, 1:1); 0.91 (diethyl ether).

(b) 2-(2-Methoxyethoxymethyl)-3-[(1-phenacyloxycarbonyl)cyclopentyl]propanoic acid Dry trifluoroacetic acid (40 ml) was added dropwise over 20 minutes to a stirred solution of the previous product (8.0 g, 0.0178 moles) in dry methylene chloride (50 ml) at 0° C. The cooling bath was then removed and stirred was continued for 3 hours, during which time the reaction mixture darkened considerably. Evaporation under vacuum provided a dark oil which was azeotroped with methylene chloride (3×50 ml), and dissolved in saturated aqueous sodium bicarbonate solution (100 ml). The resulting solution was washed with diethylether (2×50 ml), acidified to pH3 with concentrated hydrochloric acid and extracted with ethyl acetate (2×50 ml). The combined organic extracts were washed with saturated brine (2×50 ml), dried over anhydrous magnesium sulphate and filtered. The filtrate was evaporated under vacuum to give the title compound as a pale yellow oil (6.98 g, 100%), Rf (silica) 0.89 (methylene chloride/methanol/ammonia, 80:20:1).

(c) 2-(2-Methoxyethoxymethyl)-3-[(1-phenacyloxycarbonyl)cyclopentyl]propanoic acid 1-naphthyl ester To a stirred, ice-cold solution of the previous product 1.0 g, 2.55 mmole) in dry methylene chloride (30 ml) were added, successively, 1-hydroxybenzotriazole (0.38 g, 2.80 mmole), 1-naphthol (1.83 g, 12 mmole), N-methylmorpholine (0.33 g, 3.31 mmole) and 1-ethyl-3-(3-dimethylaminopropyl)carbodiimide hydrochloride (0.64 g, 3.31 mmole). After 10 minutes, the solution was concentrated to an oil which was stirred at room temperature for 18 hours and then dissolved in methylene chloride (200 ml). The latter solution was washed with water (50 ml), 2N hydrochloric acid (2×25 ml), saturated aqueous sodium bicarbonate solution (2×25 ml) and saturated brine (2×25 ml), then dried over anhydrous magnesium sulphate and filtered. Evaporation of the filtrate under vacuum gave an oil which was purified by chromatography on silica gel eluting with a hexane-ethyl acetate gradient. The appropriate fractions were combined and the solvent evaporated under vacuum to furnish the title diester as an oil (0.90 g, 68%), Rf (silica) 0.57 (ethyl acetate/hexane, 1:1).

(d) 3-[(1-Carboxycyclopentyl]-2-(2-methoxyethoxymethyl)propanoic acid 1-naphthyl ester Activated zinc dust (0.9 g, 13 mmole) was added to a stirred solution of the above diester, (0.9 g, 1.74 mmole) in glacial acetic acid (10 ml) at room temperature. After 18 hours, the reaction mixture was filtered and the filter pad washed with glacial acetic acid (2×10 ml) followed by methylene chloride (2×20 ml). The combined mother liquor and washings were evaporated under vacuum and the resulting oil azeotroped first with toluene (3×20 ml), then with methylene chloride (3×20 ml), and dissolved in diethyl ether (50 ml). The ether solution was washed with saturated aqueous sodium bicarbonate solution (3×20 ml), dried over anhydrous magnesium sulphate and filtered. Evaporation of the filtrate under vacuum provided an oil which was purified by chromatography on silica gel using a chloroform to 5% methanol in chloroform elution gradient. Evaporation of the appropriate fractions afforded the title compound as an oil (0.63 g, 91%), Rf (silica) 0.18–0.36 (ethyl acetate/hexane, 1:1).

(e) 3-{1-[(cis-4-Benzyloxycarbonyl-cyclohexyl)carbamoyl]cyclopentyl}-2-(2-methoxyethoxymethyl)-propanoic acid 1-naphthyl ester To a stirred, ice-cold solution of the previous product (0.77 g, 1.92 mmole) in dry methylene chloride (20 ml) were added successively, 1-hydroxybenzotriazole (0.29 g, 2.11 mmole), cis-4-amino-cyclohexane-carboxylic acid benzyl ester p-toluenesulphonate (0.78 g, 1.92 mmole), N-methylmorpholine (0.45 g, 4.42 mmole) and 1-ethyl-3-(3-dimethylaminopropyl)carbodiimide hydrochloride (0.48 g, 2.50 mmole). After 10 minutes, the resulting solution was concentrated to an oil which was stirred at room temperature for 18 hours. The product was dissolved in ethyl acetate (200 ml) and washed with water (2×25 ml); 1N hydrochloric acid (2×25 ml), saturated aqueous sodium bicarbonate solution (2×25 ml) and saturated brine (2×25 ml), then dried over anhydrous magnesium sulphate and filtered. Evaporation of the filtrate under vacuum gave an oil which was purified by chromatography on silica gel using hexane-ethyl acetate (3:2) as eluent. The appropriate fractions were combined and the solvent evaporated under vacuum to furnish the title compound as an oil (0.94 g, 79%), Rf (silica) 0.20 (ethyl acetate/hexane, 2:3), 0.77 (ethyl acetate).

(f) 3-{1-[(cis-4-Carboxycyclohexyl)carbamoyl]cyclopentyl}-2-(2-methoxyethoxymethyl)propanoic acid 1-naphthyl ester hemihydrate A stirred solution of the previous product (0.80 g, 1.3 mmole) in 5% aqueous ethanol was hydrogenated over 10% palladium on charcoal catalyst (80 mg) at 60 p.s.i. (4.1 bar) and room temperature for 4.5 hours. The catalyst was removed by filtration and the filtrate evaporated under vacuum. The resulting residue was azeotroped with methylene chloride (3×20 ml) to provide the title ester as a tacky white foam (0.64 g, 92%). Found: C,67.81; H,7.62; N,2.68. $C_{30}H_{39}NO_7$, 0.5 $H_2O$ requires C,67.39; H,7.54; N,2.62%.

EXAMPLES 420–423

The following compounds were prepared following the procedure of Example 419, using the appropriate aromatic alcohol for the esterification in Step 419(c).

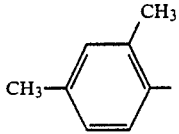

| Example No. | R[17] | Analysis % (Theoretical in brackets) | | |
|---|---|---|---|---|
| | | C | H | N |
| 420 | 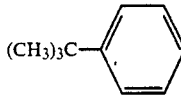 | 65.50 (66.77 | 8.23 8.20 | 2.74 2.78) |
| 421 | 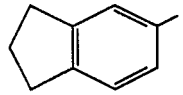 | 67.10 (67.76 | 8.62 8.53 | 2.72 2.63) |
| 422 | 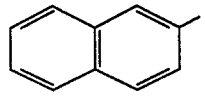 | 67.75 (67.55 | 8.07 8.02 | 2.67 2.72) |
| 423 |  | 66.65 (66.82 | 7.62 7.57 | 2.41 2.60)[1] |

[1] 0.75 hydrate

EXAMPLE 424

3-{1-[(cis-4-{S-Indanyloxycarbonyl}cyclohexyl)carbamoyl]cyclopentyl}-2-(2-methoxyethoxymethyl)-propanoic acid (a) Preparation of cis-4-benzyloxycarbonylaminocyclohexane carboxylic acid Sodium carbonate (4.03 g, 38 mmole) was added in small portions to a stirred solution of cis-4-aminocyclohexane carboxylic acid (10.0 g, 69 mmole) in a mixture of dioxane (80 ml) and water (40 ml). After 15 minutes a solution of dibenzyl dicarbonate (19.47 g, 68 mmole) in dioxane (40 ml) was added dropwise followed by water (40 ml). The mixture was stirred for 18 hours at room temperature, the solvent evaporated under vacuum and the residue partitioned between diethyl ether and water. The organic phase was washed with dilute hydrochloric acid and water, dried over sodium sulphate and evaporated under vacuum to give cis-4-benzyloxycarbonylaminocyclohexane carboxylic acid as an oil (14.5 g, 75%). Found: C,64.88; H,6.98; N,5.13. $C_{15}H_{19}NO_4$ requires C,64.97; H,6.91; N,5.05%.

(b) cis-4-Benzyloxycarbonylamino-cyclohexanecarboxylic acid 5-indanyl ester

To a stirred, ice-cold solution of the product from part (a) (1.70 g, 6.13 mmole) in dry methylene chloride (30 ml) were added sequentially, 1-hydroxybenzotriazole (0.92 g, 6.77 mmole), 5-indanol (2.0 g, 15 mmole), N-methylmorpholine (0.80 g, 7.92 mmole) and 1-ethyl-3-(3-dimethylaminopropyl)carbodiimide hydrochloride (1.53 g, 7.98 mmole). After 10 minutes, the resulting solution was concentrated to an oil which was stirred at room temperature for 18 hours and then dissolved in methylene chloride (150 ml). The latter solution was washed in turn with water (2×50 ml), saturated aqueous sodium bicarbonate solution (2×25 ml), 2N hydrochloric acid (2×25 ml) and saturated brine (2×25 ml), then dried over anhydrous magnesium sulphate and filtered. Evaporation of the solvent under vacuum, gave an oil which was purified by chromatography on silica gel eluting with hexane-ethyl acetate (4:1). The appropriate fractions were combined and the solvent evaporated under vacuum to furnish the title compound as a white solid (2.20 g, 91%), which was crystallised from a mixture of diethyl ether and n-pentane, m.p. 68°–69° C. Found: C,73.30; H,7.04; N,3.43. $C_{24}H_{27}NO_4$ requires C,73.26; H,6.92; N,3.56%.

(c) cis-4-Aminocyclohexanecarboxylic acid 5-indanyl ester hydrochloride ¼ hydrate A stirred solution of the previous product (1.10 g, 2.8 mmole) in ethanol (50 ml) and concentrated hydrochloric acid (3 ml) was hydrogenated over 10% palladium on charcoal catalyst (110 mg) at 60 p.s.i. (4.1 bar) and room temperature for 2 hours. The catalyst was removed by filtration and the filtrate evaporated under vacuum to provide the title compound as a cream solid (0.77 g, 91%), which was crystallised from hexane-tetrahydrofuran, m.p. 163°–164° C. Found: C,63.86; H,7.52; N,4.70. $C_{16}H_{21}NO_2$; HCl; 0.25 $H_2O$ requires C,63.98; H,7.54; N,4.66%.

(d) 2-(2-Methoxyethoxymethyl)-3-[(1-phenacyloxycarbonyl)cyclopentyl]propanoic acid benzyl ester Anhydrous potassium carbonate (10.55 g, 0.076 mole) was added to a stirred solution of 2-(2-methoxyethoxymethyl)-3-[(1-phenacyloxycarbonyl)cyclopentyl]-propanoic acid (Example 419 (b), 15.0 g, 0.038 mole) and benzyl bromide (6.53 g, 0.038 m) in dry dimethylformamide (100 ml). The resulting suspension was stirred at room temperature for 18 hours, then the bulk of the solvent was removed under vacuum and the residue partitioned between ethyl acetate (150 ml) and water (100 ml). The organic phase was separated, washed successively with water (50 ml), 1N hydrochloric acid (50 ml), and saturated aqueous sodium bicarbonate solution (50 ml), then dried over anhydrous magnesium sulphate. Filtration, followed by evaporation of the solvent under vacuum afforded the title benzyl ester as an oil (16.2 g, 88%), Rf (silica) 0.69 (ethyl acetate/toluene, 1:1), 0.88 (ethyl acetate).

(e) 3-(1-Carboxycyclopentyl)-2-(2-methoxyethoxymethyl)propanoic acid benzyl ester Activated zinc dust (5.0 g, 0.076 mole) was added to a stirred solution of the previous product (8.0 g, 0.0165 mole) in glacial acetic acid (50 ml) at room temperature. After 3 hours, the reaction mixture was filtered and the filter pad washed with glacial acetic acid. The combined mother liquor and washings were evaporated under vacuum and the oily residue first azeotroped with toluene (3×40 ml), then dissolved in saturated aqueous sodium bicarbonate solution (100 ml). This aqueous solution was washed with n-hexane (3×50 ml), acidified to pH 3-4 with 2M hydrochloric acid and extracted with diethyl ether (2×100 ml). The combined ether extracts were dried over anhydrous magnesium sulphate and evaporated under vacuum. The residue was azeotroped with methylene chloride (2×40 ml) to afford the title compound as a yellow oil (5.15 g, 84%), Rf (silica) 0.25-0.50 (ethyl acetate), 0.85 (methylene chloride/methanol/ammonia, 80:20:1).

(f) 3-{1-[(cis-4-{5-Indanyloxycarbonyl}cyclohexyl)-carbamoyl]cyclopentyl}-2-(2-methoxyethoxymethyl)-propanoic acid benzyl ester To a stirred, ice-cold solution of the previous product (0.91 g, 2.52 mmole) in dry methylene chloride (30 ml) were added, sequentially, 1-hydroxybenzotriazole (0.38 g, 2.74 mmole), a solution of cis-4-aminocyclohexanecarboxylic acid 5-indanyl ester hydrochloride ¼ hydrate from part (c) (0.77 g, 2.52 mmole) in dry methylene chloride (20 ml), N-methylmorpholine (0.58 g, 5.74 mmole) and 1-ethyl-3-(3-dimethylaminopropyl)carbodiimide hydrochloride (0.63 g, 3.25 mmole). After 10 minutes, the resulting solution was concentrated to an oil which was stirred at room temperature for 72 hours and then diluted with methylene chloride (250 ml). The latter solution was washed in turn with water (2×50 ml), 2N hydrochloric acid (2×50 ml), saturated aqueous sodium bicarbonate solution (2×50 ml) and saturated brine (2×50 ml), then dried over anhydrous magnesium sulphate and filtered. Evaporation of the solvent under vacuum, gave an oil which was purified by chromatography on silica gel eluting with a mixture of hexane and ethyl acetate (2:1). The appropriate fractions were combined and the solvent evaporated under vacuum to furnish the title diester as an oil (1.40 g, 91%), Rf (silica) 0.33 (ethyl acetate/hexane, 1:1).

(g) 3-{1-[(cis-4-{5-Indanyloxycarbonyl}cyclohexyl)-carbamoyl]cyclopentyl}-2-(2-methoxyethoxymethyl)-propanoic acid A stirred solution of the previous product (1.40 g, 2.3 mmole) in ethanol (50 ml) was hydrogenated over 10% palladium on charcoal catalyst (140 mg) at 60 p.s.i. (4.1 bar) and room temperature for 18 hours. The catalyst was removed by filtration and the filtrate evaporated under vacuum to give an oil which was azeotroped with methylene chloride (3×40 ml) to provide the title compound as an oil (0.95 g, 81%), Rf (silica) 0.90 (methylene chloride/methanol/ammonia, 80:20:1). Found: C,66.25; H,7.70; N,2.72. $C_{29}H_{41}NO_7$, 0.2 $CH_2Cl_2$ requires C,65.84; H,7.83; N,2.63%.

EXAMPLE 425

3-{1-[(cis-4-Ethoxycarbonylcyclohexyl)carbamoyl]cyclopentyl}-2-(2-methoxyethoxymethyl)propanoic acid hemihydrate (a) Oxalyl chloride (0.26 g, 2.1 mmole) was added to a stirred, ice-cold solution of 3-(1-carboxycyclopentyl)-2-(2-methoxyethoxymethyl)propanoic acid benzyl ester (0.50 g, 1.37 mmole) in dry methylene chloride (10 ml), followed by 1 drop of dry dimethylformamide. The resulting solution was stirred at room temperature for 3.5 hours, the solvent evaporated under vacuum, and the residue azeotroped with methylene chloride (3×25 ml). The neat acid chloride thus obtained was treated with an ice-cold solution of cis-4-aminocyclohexanecarboxylic acid ethyl ester hydrochloride (0.28 g, 1.37 mmole) in dry methylene chloride (5 ml) followed by the dropwise addition, with stirring, of a solution of triethylamine (0.42 g, 4.11 mmole) in dry methylene chloride (5 ml). The reaction mixture was stirred at room temperature for 18 hours, then diluted with methylene chloride (200 ml) and washed in turn with 2N hydrochloric acid (2×50 ml), saturated aqueous sodium bicarbonate solution (2×50 ml) and saturated brine (2×50 ml) and dried over anhydrous magnesium sulphate. The solvent was evaporated under vacuum to give an oil which was purified by chromatography on silica gel eluting with a mixture of hexane and ethyl acetate (3:2). The appropriate fractions were combined and the solvent evaporated under vacuum to afford 3-{1-[(cis-4-ethoxycarbonylcyclohexyl)carbamoyl]cyclopentyl}-2-(2-methoxyethoxymethyl)propanoic acid benzyl ester as an oil (0.51 g, 72%), Rf (silica) 0.40 (ethyl acetate/hexane, 1:1).

(b) A stirred solution of the product from part (a) (0.50 g, 0.965 mmole) in 5% aqueous ethanol (40 ml) was hydrogenated over 10% palladium on charcoal catalyst (50 mg) at 60 p.s.i. (4.1 bar) and room temperature for 18 hours. The catalyst was removed by filtration and the filtrate evaporated under vacuum to yield a gum which was azeotroped with methylene chloride (3×40 ml) and dried under high vacuum to give the desired ethyl ester as a gum (0.41 g, 100%), Found: C,60.48; H,8.79; N,3.30. $C_{22}H_{37}NO_7$, 0.5 $H_2O$ requires C,60.52; H,8.77; N,3.21%.

EXAMPLE 426

3-{1-[(cis-4-Carboxycyclohexyl)carbamoyl]cyclopentyl}-2-(2-methoxyethoxymethyl)propanoic acid benzyl ester (a) cis-4-Amino-cyclohexanecarboxylic acid t-butyl ester hydrochloride cis-4-Benzyloxycarbonylamino-cyclohexanecarboxylic acid (Example 19(a) (14.5 g, 52 mmole) was dissolved in dichloromethane (100 ml) and cooled to −78° C. Liquid isobutylene (100 ml), and concentrated sulphuric acid (1.0 ml) were added, and the reaction mixture sealed in a pressure bottle and allowed to warm to room temperature with shaking overnight. Excess isobutylene was vented, dilute sodium bicarbonate solution was added and the solvent removed under vacuum. The residue was partitioned between diethyl ether and dilute aqueous sodium bicarbonate and the organic phase dried over anhydrous sodium sulphate and evaporated to give an oil (35 g). Purification by column chromatography on silica gel eluting with a mixture of diethyl ether and dichloromethane followed by crystallisation from n-pentene at 0° C. gave cis-4-benzyloxycarbonylamino-cyclohexane carboxylic acid t-butyl ester as white needles (3.77 g, 22%) m.p. 73°-74° C.. This product was dissolved in ethanol (200 ml) and hydrogenated at 30 p.s.i. (2.0 bar) over 10% palladium on charcoal catalyst for 4 hours at room temperature. The reaction mixture was filtered and the solvent evaporated under reduced pressure. The residue was taken up in dichloromethane, filtered and the solvent evaporated to give an oil which was dissolved in dry diethylether and treated with ethereal hydrogen chloride to pH 3. The resulting precipitate was collected and dried to give the title ester hydrochloride as a white solid (2.34 g, 90%) m.p. 180° (dec.). Found: C,55.95; H,9.35; N,5.68. $C_{11}H_{21}NO_2.HCl$ requires C,56.04; H,9.41; N,5.94%.

(b) 3-{1-[(cis-4-t-Butoxycarbonylcyclohexyl)carbamoyl]cyclopentyl}-2-(2-methoxyethoxymethyl)-propanoic acid benzyl ester The amine hydrochloride from part (a) (1.37 g, 5.76 mmole) was coupled to 3-(1carboxycyclopentyl)-2-(2-methoxyethoxymethyl)propanoic acid benzylester (1.98 g, 5.4 mmole) from Example 434(e) following the procedure of Example 424(f) to give the title diester as an oil (2.33 g 75%). Found: C,68.39; H,8.75, N,2.37. $C_{31}H_{47}NO_7$ requires C,68.22; H,8.68; N,2.57%.

(c) 3-{1-[(cis-4-Carboxycyclohexyl)carbamoyl]cyclopentyl}-2-(2-methoxyethoxymethyl)propanoic acid benzyl ester The product from part (b) above (2.33 g, 4.09 mmol) was dissolved in dry trifluoroacetic acid (20 ml) and the reaction mixture stored at 0°–4′ C. overnight. The trifluoroacetic acid was removed under vacuum and the residue dissolved in aqueous sodium bicarbonate (50 ml) and extracted with diethyl ether (3×100 ml). The aqueous phase was acidified with dilute hydrochloric acid and extracted with ethyl acetate. The ethyl acetate extracts were dried over anhydrous sodium sulphate and evaporated under vacuum. The residue was azeotroped with dichloromethane and dried under vacuum to give an oil which crystallised onstanding to give the title benzyl ester as a white solid (1.40 g, 70%), m.p. 83°–85° C. Found: C,65.97; H,8.17; N,2.87. $C_{27}H_{39}NO_7$ requires C,66.24; H,8.03; N,2.86%.

EXAMPLE 427

3-{1-[cis-4-(2,2-Dimethylpropanoyloxymethoxycarbonyl)cyclohexyl)carbamoyl]cyclopentyl}-2-(2-methoxyethoxymethyl)propanoic acid (a) A solution of caesium carbonate (133 mg, 0.41 mmole) in water (5 ml) was added to a solution of 3-{1-[(cis-4-carboxycyclohexyl)carbamoyl]cyclopentyl}-2-(2-methoxyethoxymethyl)propanoic acid benzyl ester (400 mg, 0.82 mmole) in acetonitrile (15 ml) and the solvent evaporated under reduced pressure. The residue was azeotroped with acetonitrile (2×) to give the caesium salt as a foam. This was suspended in dimethylformamide (2 ml), chloromethyl pivalate (148 mg, 0.98 mmole) added and the mixture was stirred at room temperature overnight. Diethyl ether (30 ml) was added and the solution washed with water, dried over anhydrous magnesium sulphate and the solvent evaporated. The residue was chromatographed on silica eluting with a mixture of ethyl acetate and hexane (1:5) to give 3-{1-[cis-4-(2,2-dimethylpropanoyloxymethoxycarbonyl)cyclohexyl)carbamoyl]cyclopentyl}-2-(2-methoxyethoxymethyl)propanoic acid benzyl ester as a colourless gum (510 mg, 100%). Found: C,65.45, H,8.17; N,2.49. $C_{33}H_{49}NO_9$ requires C,65.65; H,8.18; N,2.32%.

(b) A solution of the diester from (a) above (450 mg, 0.75 mmole) in methanol (18 ml) and water (12 ml) was hydrogenated at 50 p.s.i. (3.45 bar) over 5% palladium on carbon catalyst (50 mg) at room temperature for 5 hours. The catalyst was removed by filtration and the filtrate evaporated under reduced pressure to give the desired pivaloyloxymethyl ester as a colourless gum (265 mg 69%). Found: C,60.56; H,8.50; N,2.8. $C_{26}H_{43}NO_9$ requires C,60.80; H,8.44; N,2.73%.

EXAMPLE 428

3-{1-[(cis-4-{5-Indanyloxycarbonyl}cyclohexyl)carbamoyl]cyclopentyl}-2-(2-methoxyethoxymethyl)-propanoic acid 5-indanyl ester To a stirred, ice-cold solution of 3-{1-[(cis-4-carboxycyclohexyl)carbamoyl]cyclopentyl}-2-(2-methoxyethoxymethyl)propanoic acid (0.50 g, 1.25 mmole) in dry methylene chloride (30 ml) were added, sequentially, 1-hydroxybenzotriazole (0.37 g, 2.76 mmole), 5-indanol (0.67 g, 5.0 mmole), N-methylmorpholine (0.33 g, 3.3 mmole) and 1-ethyl-3-(3-dimethylaminopropyl)carbodiimide hydrochloride (0.62 g, 3.2 mmole). After 10 minutes, the resulting solution was concentrated to an oil which was stirred at room temperature for 18 hours. The reaction mixture was diluted with methylene chloride (120 ml) and the solution was washed in turn with water (2×20 ml), saturated aqueous sodium bicarbonate solution (2×20 ml) and saturated brine (2×20 ml), dried over anhydrous magnesium sulphate and filtered. Evaporation of the filtrate under vacuum gave an oil which was purified by chromatography on silica gel using a hexane-ethyl acetate elution gradient. The appropriate fractions were combined and evaporated under vacuum to afford the title bis-5-indanyl ester as an oil (0.52 g, 65%), Rf (silica) 0.50 (ethyl acetate). Found: C,71.35; H,8.01; N,2.06. $C_{38}H_{49}NO_7$, 0.1 $CH_2Cl_2$ requires C,71.50; H,7.74; N,2.19%.

EXAMPLE 429

3-{1-[(cis-3-Carboxycyclohexyl)carbamoyl]cyclopentyl}-2-(3-chloropropyl)propanoic acid 3-(1-Carboxycyclopentyl)-2-(3-chloropropyl)propanoic acid t-butyl ester was prepared following the procedure of Example 38, using the propanoic ester of Example 35 and 1-chloro-3-iodopropane as starting materials. The product was isolated as an oil (71%), Rf 0.38 (silica; chloroform, hexane, 2-propanol, 2-propylamine, 200:100:20:1).

The above glutaric acid derivative was coupled with cis-3-amino-cyclohexanecarboxyl acid ethyl ester using the procedure of Example 81 to afford 3-{1-[cis-3-ethoxycarbonylcyclohexyl)carbamoyl]cyclopentyl}-2-(3-chloropropyl)propanoic acid t-butyl ester as an oil (77%). Found: C,63.31; H,9.01; N,2.94. $C_{25}H_{42}ClNO_5$ requires C,63.60; H,8.97; N,2.97%.

The above diester was treated with trifluoroacetic acid following the procedure of Example 242 to provide 3-{-1-[cis-3-ethoxycarbonyl-cyclohexyl)carbamoyl]cyclopentyl}-2-(3-chloropropyl)propanoic acid as an oil (76%). Found: C,60.13; H,8.30; N,3.10. $C_{21}H_{34}ClNO_5$ requires C,60.63; H,8.24; N,3.37%.

The above monoester was hydrolysed using the procedure of Example 323 to furnish the title diacid as a gum (80%). Found: C,58.77; H,7.79; N,3.33. $C_{15}H_{30}ClNO_5$ requires C,58.83; H,7.80; N,3.61%.

EXAMPLE 430

3-{1-[(cis-3-Carboxycyclohexyl)carbamoyl]cyclopentyl}-2-[2-(phenylsulphonyl)ethyl]propanoic acid 3-(1-Carboxycyclopentyl)-2-[2-(phenylsulphonyl)ethyl]propanoic acid t-butyl ester was prepared following the procedure of Example 38, using as starting materials the propanoic ester of Example 35 and phenyl vinyl sulphone. The product was isolated as an oil (15%). Found: C,60.25; H,7.24. $C_{21}H_{30}O_6S$. 0.13

CH$_2$Cl$_2$ requires C,60.24; H,7.24%. The above glutaric acid derivative was coupled with cis-3-amino-cyclohexanecarboxylic acid ethyl ester using the general procedure of Example 81 to yield 3-{1-[cis-3-ethoxycarbonylcyclohexyl)carbamoyl]cyclopentyl}-2-[2-(phenylsulphonyl)ethyl]propanoic acid t-butyl ester as a foam (71%). Found: C,63.53; H,8.02; N,2.38. C$_{30}$H$_{45}$NO$_7$S requires C,63.91; H,8.05; N,2.48%. The above diester was treated with trifluoroacetic acid using the procedure of Example 242 to give 3-{1-[(cis-3-ethoxycarbonyl-cyclohexyl)carbamoyl]cyclopentyl}-2-[2-(phenyl-sulphonyl)ethyl]propanoic acid as a foam (96%). Found: C,61.90; H,7.54; N,2.86. C$_{26}$H$_{37}$NO$_7$S requires C,61.51; H,7.35; N,2.76%. The above monoester was hydrolysed using the general procedure of Example 323 to give the title diacid as a foam (95%). Found: C,59.00; H,6.83; N,2.51. C$_{24}$H$_{33}$NO$_7$S. 0.5 H$_2$O. 0.1 CH$_3$CO$_2$C$_2$H$_5$ requires C,58.92; H,7.04; N,2.81%.

EXAMPLE 431

(2S)-(2-Methoxyethoxymethyl)-3-[1-(phenacyloxycarbonyl)cyclopentyl]propanoic acid N-acetyl-(1R,2S)-ephedrine ester N,N'-Dicyclohexylcarbodiimide (5.66 g, 24.5 mmole) was added to an ice cold, stirred solution of N-acetyl-(1R,2S)-ephedrine (4.24 g, 20.46 mmole), 2-(2-methoxyethoxymethyl)-3-[1-(phenacyloxycarbonyl)cyclopentyl]propanoic acid (8.43 g, 21.48 mmole) and 4-dimethylaminopyridine (1.23 g, 10 mmole) in dry methylene chloride (100 ml). After one hour the solution was allowed to warm to ambient temperature and stirred for 2½ days. The suspension was filtered, the solvent evaporated under reduced pressure and the residue partitioned between diethyl ether and water. The organic layer was washed sequentially with 0.5N hydrochloric acid, water, saturated aqueous sodium bicarbonate, and water. Drying (MgSO$_4$) and evaporation gave the crude mixture of diastereoisomers as an oil (12.5 g), which was chromatographed on silica eluting with hexane containing increasing proportions of ethyl acetate (4:6 to 1:9). The faster running component, having Rf 0.45 (silica; ethyl acetate) was the desired diastereoisomer and was obtained following evaporation of the relevant fractions as a gum (5.21 g, 44%). $[\alpha]_D^{25} -34.1°$, $[\alpha]_{365}^{25} -111.0°$ (c=1.0, CH$_2$Cl$_2$). Found: C,68.19; H,7.59; N,2.46. C$_{33}$H$_{43}$NO$_8$ requires C,68.14; H,7.45, N,2.41%

The other diastereoisomer had an Rf of 0.35 (silica; ethyl acetate); $[\alpha]_D^{25} -21.5°$, $[\alpha]_{365}^{25} -67.3°$ (c=1.0, CH$_2$Cl$_2$).

EXAMPLE 432

(2S)-(2-Methoxyethoxymethyl)-3-(1-carboxycyclopentyl)propanoic acid N-acetyl-(1R,2S)-ephedrine ester A solution of (2S)-(2-methoxyethoxymethyl)-3-[1-(phenacyloxycarbonyl)cyclopentyl]propanoic acid N-acetyl-(1R,2S)-ephedrine ester (5.17 g, 8.89 mmole) in glacial acetic acid (40 ml) was stirred with activated zinc dust (3.0 g, 47.7 mmole) at room temperature under nitrogen for two hours. The mixture was filtered and the filtrate evaporated to dryness under vacuum, traces of acetic acid being removed by azeotroping with toluene. The residue was dissolved in diethyl ether and the solution extracted with 1N sodium hydroxide solution (12 ml) and washed with water. The combined extracts were acidified with concentrated hydrochloric acid and extracted with diethyl ether. The ether extracts were washed with saturated brine, dried (MgSO$_4$) and evaporated to give the title product as a thick oil (4.03 g, 98%). Found: C,63.96; H,8.21; N,2.87. C$_{25}$H$_{37}$NO$_7$ (0.3 H$_2$O) requires C,64.03; H,8.08; N,2.99%. $[\alpha]_D^{25} -34.9°$, $[\alpha]_{365}^{25} -115.4°$ (c=1.03, CH$_2$Cl$_2$).

EXAMPLE 433

3-{1-[(cis-4-Ethoxycarbonylcyclohexyl)carbamoyl]cyclopentyl}-(2S)-(2-methoxyethoxymethyl)propanoic acid N-acetyl-(1R,2S)-ephedrine ester 1-Ethyl-3-(3-dimethylaminopropyl)carbodiimide hydrochloride (3.32 g, 17.34 mmole) was added to an ice cold stirred mixture of the product of Example 2 (3.98 g, 8.58 mmole), cis-4-aminocyclohexanecarboxylic acid ethyl ester hydrochloride (2.70 g, 13 mmole), 1-hydroxybenzotriazole (1.17 g, 8.67 mmole) and N-methylmorpholine (3.07 g, 30.34 mmole) in dry methylene chloride (30 ml). After 15 minutes the mixture was allowed to warm to ambient temperature and to stand overnight. The solvent was evaporated under vacuum and the residue partitioned between diethyl ether and water. The organic layer was washed sequentially with water, 2N-hydrochloric acid, water, saturated aqueous sodium bicarbonate and water. The solution was dried (MgSO$_4$) and the solvent evaporated to give a gum which was chromatographed on silica eluting with ethyl acetate. Further chromatography of the product containing fractions on silica eluting with a mixture of hexane and ethyl acetate (15:85) gave the title compound as a gum (4.65 g, 88%). $[\alpha]_D^{25} -30.3°$, $[\alpha]_{365}^{25} -101.3°$ (c=1.01, CH$_2$Cl$_2$). Found: C,66.16; H,8.66; N,4.45. C$_{34}$H$_{52}$N$_2$O$_8$ requires C,66.21; H,8.50; N,4.54%.

EXAMPLE 434

(S)-cis-4-{1-[2-Carboxy-3-(2-methoxyethoxy)propyl]-1-cyclopentanecarboxamido}-1-cyclohexanecarboxylic acid The diester product from Example 433 (4.52 g, 7.33 mmole) in a mixture of ethanol (50 ml) and water (50 ml) was hydrogenated over 10% palladium on charcoal catalyst (2.5 g) at 60 p.s.i. (4.1 bar) at room temperature for 24 hours. The mixture was filtered and the filtrate evaporated under reduced pressure. The residue was taken up in diethyl ether and the mono-ester product was extracted into 1N sodium hydroxide (30 ml) the ether being washed with water (30 ml). The combined aqueous extracts were washed with diethyl ether and allowed to stand at room temperature for three days. The solution was saturated with salt, acidified with concentrated hydrochloric acid and extracted with methylene chloride. The organic extract was washed with saturated brine, dried (MgSO$_4$) and the solvent evaporated. Recrystallisation from a mixture of hexane and ethyl acetate gave the title product as a white solid (2.32 g, 79%), m.p. 107.5°-108° C. $[\alpha]_D^{25} +2.7°$, $[\alpha]_{365}^{25} +5.1°$ (c=1.58 CH$_2$Cl$_2$). Found: C,60.18; H,8.44; N,3.82. C$_{20}$H$_{33}$NO$_7$ requires C,60.13; H,8.33; N,3.51%.

EXAMPLE 435

Phenacyl 1-[2-(5-indanyloxycarbonyl)-3-(2-methoxyethoxy)-propyl]-1-cyclopentanecarboxylate 1-(3-Dimethylaminopropyl)-3-ethylcarbodiimide hydrochloride (31.1 g, 0.1625 mole) was added to a stirred solution of 2-(2-methoxyethoxymethyl)-3-[1-

(phenacyloxycarbonyl)cyclopentyl]propanoic acid (49 g, 0.125 mole), 5-indanol (83.6 g, 0.625 mole), 1-hydroxybenzotriazole hydrate (18.6 g, 0.1375 mole) and N-methylmorpholine (16.3 g, 0.1625 mole), in methylene chloride (100 ml). The solution was stirred at ambient temperature for 18 hours, diluted with further methylene chloride (300 ml) and washed sequentially with water (2×100 ml), 2N hydrochloric acid (2×100 ml) and saturated aqueous sodium bicarbonate (2×100 ml). Drying (MgSO$_4$) and evaporation gave an oil (129 g) which was chromatographed on silica (1 kg) eluting with hexane containing increasing proportions of ethyl acetate (4:1 to 2:1) to give the title diester as a pale yellow oil (54.5 g; 86%), Rf. 0.54 (silica; hexane, ethyl acetate 2:1).

EXAMPLE 436

1-[2-(5-Indanyloxycarbonyl)-3-(2-methoxyethoxy)-propyl]-1-cyclopentanecarboxylic acid Activated zinc dust (36 g, 0.554 mole) was added portionwise over 45 minutes to a stirred solution of the diester from Example 5 (54 g, 0.106 mole) in glacial acetic acid (378 ml), the temperature being allowed to rise to 32° C. After stirring for 18 hours a further portion of activated zinc dust (36 g, 0.554 mole) was added and the mixture stirred for another hour. The reaction mixture was filtered and the filtrate was evaporated to an oil (46 g) which was chromatographed on silica (500 g) eluting with hexane containing increasing proportions of ethyl acetate (4:1 to 1:1) to give the title ester as a colourless oil (37.8 g, 91.5%) Rf. 0.23 (silica; hexane, ethyl acetate 2:1).

This product could be further characterised as its isopropylamine salt m.p. 76°-8° C. (hexane). Found: C,66.19; H,8.64; N,3.04. C$_{23}$H$_{39}$NO$_6$ requires C,66.79; H,8.75; N,3.12%.

EXAMPLE 437

(S)-1-[2-(5-Indanyloxycarbonyl)-3-(2-methoxyethoxy)-propyl]-1-cyclopentanecarboxylic acid A hot solution of (+)pseudoephedrine (1.98 g) in ethyl acetate (6 ml) was run into a cooled and stirred solution of 1-[2-(5-indanyloxycarbonyl)-3-(2-methoxyethoxy)propyl]-1-cyclopentanecarboxylic acid (4.68 g) in toluene (6 ml), the temperature being allowed to rise to 35° C. The resulting clear solution was chilled to induce crystallisation and granulated at 5° C. for several hours. Filtration and drying gave the crude (+)pseudoephedrine salt of the (S)-acid (4.0 g, 60%) as a white solid m.p. 98°-102° C. Recrystallisation of 3.5 g of this material from a mixture of toluene (10.5 ml) and ethyl acetate (10.5 ml) gave the (+)-pseudoephedrine salt of the title compound (2.2 g, 62.8% recovery) as white crystals m.p. 111°-3° C., [α]$_D$+25.1° (c=5, MeOH). Found: C,69.19; H,8.20; N,2.38. C$_{32}$H$_{45}$NO$_7$ requires C,69.16; H,8.16; N,2.51%.

A sample of this salt (2 g) was suspended in a mixture of hexane (5 ml), ethyl acetate (5 ml) and water (10 ml) and concentrated hydrochloric acid was added dropwise to adjust the pH of the aqueous phase to 1.5. The two phases of the solution were separated, and the aqueous phase was washed with a 1:1 ethyl acetate-hexane mixture (10 ml). Evaporation of the combined organic layers gave the title compound as a colourless oil (1.2 g, 85% from salt), [α]$_D$−3.5° (c=5, MeOH), Rf. 0.41 (silica; toluene, acetic acid 8:2). Found: C,67.25; H,7.77. C$_{22}$H$_{30}$O$_6$ requires C,67.67; H,7.74%. A chiral NMR assay of this product showed it to be substantially pure S enantiomer containing only 4% of the R enantiomer.

EXAMPLE 438

(S)-Benzyl cis-4-{1-[2-(5-indanyloxycarbonyl)-3-(2-methoxyethoxy)propyl]-1-cyclopentanecarboxamido}-1-cyclohexanecarboxylate 1-(3-Dimethylaminopropyl)-3-ethylcarbodiimide hydrochloride (337.5 mg, 1.76 mmole) was added to a stirred solution of (S)-1-[2-(5-indanyloxycarbonyl)-3-(2-methoxyethoxy)propyl]-1-cyclopentanecarboxylic acid (625 mg, 1.6 mmole), benzyl cis-4-amino-1-cyclohexanecarboxylate p-toluenesulphonate. (700 mg, 1.73 mmole), 1-hydroxybenzotriazole hydrate (240 mg, 1.78 mmole) and N-methylmorpholine (560 mg, 5.5 mmole) in methylene chloride (3.75 ml). The solution was stirred at ambient temperature for eighteen hours, evaporated under vacuum and the residue partitioned between diethyl ether and water. The organic extract was washed sequentially with 1N hydrochloric acid, saturated aqueous sodium bicarbonate, and water. Drying (MgSO$_4$) and evaporation gave an oil (0.9 g) which was chromatographed on silica (25 g) eluting with hexane containing increasing proportions of ethyl acetate (4:1 to 3:1) to give the required diester as an oil (830 mg, 86%) [α]$_D$−3.3° (c=1, MeOH), Rf. 0.52 (silica; ethyl acetate). Found: C,70.32; H,7.74; N,2.19. C$_{36}$H$_{47}$NO$_7$(0.5 H$_2$O) requires C,70.33; H,7.87; N,2.28%.

EXAMPLE 439

(S)-cis-4-{1-[2-(5-Indanyloxycarbonyl)-3-(2-methoxyethoxy)propyl]-1-cyclopentanecarboxamido}-1-cyclohexanecarboxylic acid A solution of (S)-benzyl cis-4-{1-[2-(5-indanyloxycarbonyl)-3-(2-methoxyethoxy)propyl]-1-cyclopentanecarboxamido}-1-cyclohexanecarboxylate (597 mg, 0.986 mmole) in 5% aqueous ethanol (10 ml) was hydrogenated over 10% palladium on charcoal catalyst (60 mg) at 60 p.s.i. (4.1 bar) and room temperature for 3.5 hours. The catalyst was removed by filtration and the filtrate evaporated under vacuum. The residue was dissolved in diethyl ether (50 ml) and the solution was clarified by filtration, and concentrated to low volume (about 5 ml) when crystallisation occurred. After granulation, filtration and drying gave the title ester (390 mg, 77%) as white crystals m.p. 107°-9° C., [α]$_D$−5.8° (c=1, MeOH), Rf. 0.40 (silica; toluene, dioxan, acetic acid 90:24:5). Found: C,67.45; H,8.18; N,2.63. C$_{29}$H$_{41}$NO$_7$ requires C,67.55; H,8.01; N,2.72%.

EXAMPLE 440

(S)-1-[2-(tert-Butoxycarbonyl)-3-(2-methoxyethoxy)-propyl]-1-cyclopentanecarboxylic acid A solution of 1-[2-(tert-butoxycarbonyl)-3-(2-methoxyethoxy)propyl]-1-cyclopentanecarboxylic acid (110.1 g, 0.333 mole) in hexane (550 ml) was treated with (+) pseudoephedrine (55.1 g, 0.333 mole) and the mixture was heated to reflux. The resulting solution was cooled to induce crystallisation, and stirred at 5° C. for 1 hour to granulate the crystals. After overnight refrigeration at 5° C., filtration, washing with hexane (200 ml) and drying gave the crude (+) pseudoephedrine salt of the (S) acid (89.9 g, 54.4%) as a white solid m.p. 76°-80° C. Recrystallisation of 30 g of this material twice from hexane (225 ml) gave the (+)pseudoephedrine salt of the title compound (21.45 g, 71.5% recovery) as white crystals m.p. 86°-7° C., $[\alpha]_D+34.9°$ (c=1, MeOH). Found: C,65.21; H,9.23; N,2.91. $C_{27}H_{45}NO_7$ requires C,65.42; H,9.15; N,2.82%.

A sample of this salt (10 g) was suspended in hexane (50 ml), and treated with 2N hydrochloric acid (15 ml) (the pH of the aqueous phase was 1.5). The two phases of the solution were separated, and the hexane phase was washed with water (15 ml). Evaporation of the organic layer gave the title compound as a colourless oil (6.3 g, 94% from salt), $[\alpha]_D+2.9°$ (c=2, MeOH), Rf. 0.44 (silica; diethyl ether, hexane, acetic acid 75:25:1) Found: C,61.41; H,9.17. $C_{17}H_{30}O_6$ requires C,61.79; H,9.15%. A chiral NMR assay of this product showed it to be substantially pure (S) enantiomer containing only 3% of the (R) enantiomer.

EXAMPLE 441

(S)-Benzyl cis-4-{1-[2-(tert-butoxycarbonyl)-3-(2-methoxyethoxy)-propyl]-1-cyclopentanecarboxamido}-1-cyclohexanecarboxylate A solution of (S)-1-[2-(tert-butoxycarbonyl)-3-(2-methoxyethoxy)propyl]-1-cyclopentanecarboxylic acid (6.61 g, 0.02 mole) in methylene chloride (40 ml) was treated with benzyl cis-4-amino-1-cyclohexane carboxylate p-toluenesulphonate (8.11 g, 0.02 mole) and water (26 ml) adjusted to pH 8.5 with 5N aqueous sodium hydroxide. To the stirred two phase solution was added propanephosphonic acid cyclic anhydride (17.8 g of commercial 50% w/w solution in methylene chloride, 0.028 mole) over 45 minutes with dropwise addition of 5N aqueous sodium hydroxide solution to maintain the pH at 8.5. The mixture was stirred for 18 hours and treated with further benzyl cis-4-amino-1-cyclohexanecarboxylate p-toluenesulphonate (2.03 g, 0.005 mole) and propanephosphonic acid cyclic anhydride (12.7 g 50% w/w solution, 0.02 mole), maintaining the pH of the aqueous phase at 8.5 by addition of 5N aqueous sodium hydroxide solution. After stirring for another hour the phases were separated and the organic phase was washed with water (20 ml) and evaporated to an oil (13.04 g) which was chromatographed on silica (300 g). Elution with hexane containing increasing proportions of ethyl acetate (4:1 to 7:3) gave the required diester as an oil (8.12 g, 79.1%) $[\alpha]_D-0.4°$ (c=2, MeOH), Rf. 0.55 (silica: ethyl acetate).

EXAMPLE 442

(S)-Benzyl cis-4-{1-[2-carboxy-3-(2-methoxyethoxy)propyl]-1-cyclopentanecarboxamido}-1-cyclohexanecarboxylate To (S)-benzyl cis-4-{1-[2-tert-butoxycarbonyl)-3-(2-methoxyethoxy)propyl]-1-cyclopentanecarboxamido}-1-cyclohexanecarboxylate (50 g, 0.0917 mole) was added trifluoroacetic acid (100 ml; 1.298 mole) with stirring and cooling to maintain the temperature below 25° C. The solution was allowed to stand for 18 hours, evaporated under vacuum, and the residue (50.2 g) dissolved in ethyl acetate (250 ml). The solution was washed with water (250 ml) adjusted to pH 3.0 with a little saturated aqueous sodium carbonate solution, and then with further water (30 ml). The organic layer was evaporated to give the title compound as a pale amber oil (44.19 g, 98.4%), $[\alpha]_D+0.9°$, (c=1, MeOH), Rf. 0.76 (silica; methylene chloride, methanol, acetic acid 90:10:1).

EXAMPLE 443

(S)-Benzyl cis-4-{1-[2-(5-indanyloxycarbonyl)-3-(2-methoxyethoxy)propyl]-1-cyclopentanecarboxamido}-1-cyclohexanecarboxylate A solution of (S)-benzyl cis-4-{1-[2-carboxy-3-(2-methoxyethoxy)propyl]-1-cyclopentanecarboxamido}-1-cyclohexanecarboxylate (12.2 g, 0.025 mole) in methylene chloride (12.2 ml) was treated with 5-indanol (6.7 g, 0.05 mole) and then with 1-propanephosphonic acid cyclic anhydride (52.3 g of commercial 50% w/w solution in methylene chloride, 0.0825 mole). The solution was stirred for 17 hours at ambient temperature, and washed sequentially with water (50 ml), 0.5M aqueous potassium hydroxide (20 ml) and water (12 ml). Drying (MgSO$_4$) and evaporation gave an oil (16.54 g) which was chromatographed on silica (60 g) eluting with hexane containing increasing proportions of ethyl acetate (3:1 to 1:1) to give the title diester as a pale yellow oil (10.9 g; 72.1%), $[\alpha]_D-3.3°$ (c=1, MeOH), Rf. 0.52 (silica; ethyl acetate), Rf. 0.35 (silica; ethyl acetate, toluene 1:1).

This material is identical to that described in Example 438 and is converted in identical manner to (S)-cis-4-{1-[2-(5-indanyloxycarbonyl)-3-(2-methoxyethoxy)-propyl]-1-cyclopentanecarboxamido}-1-cyclohexanecarboxylic acid (as described in Example 439).

EXAMPLE 444

(S)-cis-4-{1-[2-Carboxy-3-(2-methoxyethoxy)propyl]-1-cyclopentanecarboxamido}-1-cyclohexanecarboxylic acid A solution of (S)-benzyl cis-4-{1-[2-carboxy-3-(2-methoxyethoxy)propyl]-1-cyclopentanecarboxamido}-1-cyclohexanecarboxylate (4.0 g, 8.18 mmole) in 5% aqueous ethanol (20 ml) was hydrogenated over 5% palladium on charcoal catalyst (0.4 g 50% wet catalyst) at 60 p.s.i. (4.1 bar) and room temperature for 18 hours. The catalyst was removed by filtration and the filtrate was evaporated under vacuum. The residue (3.42 g) was recrystallised from ethyl acetate (13.7 ml) to give the title diacid (2.15 g, 63%) as white crystals m.p. 108.5°-9.1° C., $[\alpha]_D+1.4°$ (c=1, MeOH), Rf. 0.55 (silica; methylene chloride, methanol, acetic acid 90:10:1). Found C,60.11; H,8.34; N,3.36. $C_{20}H_{33}NO_7$ requires C,60.13; H,8.33; N,3.51%.

This material is identical to that described in Example 434. A chiral NMR assay of this product showed it substantially pure (S) enantiomer containing only 3% of the (R) enantiomer.

EXAMPLE 445

The activity of the racemate and separated enantiomers of the cis-4-{1-[2-carboxy-3-(2-methoxyethoxy)-propyl]-1-cyclopentanecarboxamido}-1-cyclohexanecarboxylic acid was assessed by measuring their ability to inhibit the neutral endopeptidase E.C.3.4.24.11 in vitro or to induce natriuresis in mice in vivo following the procedures described herein.

| Enantiomer | IC$_{50}$ against E.C.3.4.24.11 (molar) | Natriuresis in mouse (i.v.) |
| --- | --- | --- |
| (±) R,S | $4.8 \times 10^{-8}$ | active at 3 mg/kg |
| (+) S | $3.9 \times 10^{-8}$ | active at 1.5 mg/kg |
| (−) R | less than $10^{-6}$ | inactive at 3 mg/kg |

EXAMPLE 446 c-4-Amino-c-2-butyl-r-1-cyclohexanecarboxylic acid ethyl ester hydrochloride (1) cis-2-Butyl-4-oxocyclohexane carboxylic acid ethyl ester 2-Butyl-4-oxocyclohex-2-ene carboxylic acid ethyl ester [Tetrahedron 37 1033 (1981)] (4.48 g; 20 mmole) dissolved in absolute ethanol (15 ml) containing 2N hydrochloric acid (1 ml) was reduced at room temperature over 5% palladium on carbon (150 mg) at 50 p.s.i. (3.45 bar). After one hour the mixture was filtered through avicel and the solvent was evaporated under reduced pressure. The residue was taken up in diethyl ether and washed successively with water, saturated aqueous sodium bicarbonate and water. Drying over MgSO$_4$ and evaporation gave an oil (4.2 g) which was chromatographed on silica. Elution with diethyl ether:hexane (2:8) gave the pure title ester (3.6 g, 80%) as a clear liquid. Found: C,68.86; H,9.84. C$_{13}$H$_{22}$O$_3$ requires C,68.99; H,9.80%.

(2) cis-2-Butyl-4-hydroximinocyclohexanecaboxylic acid ethyl ester

Sodium acetate (1.56 g; 19 mmole) and hydroxylamine hydrochloride (1.32 g; 19 mmole) were dissolved in water (5 ml). Ethanol (50 ml) was added and the mixture was filtered. The above ester (3.57 g; 15.8 mmole) was added and the solution was refluxed for two hours. The solvent was evaporated under reduced pressure and the residue partitioned between diethyl ether and water. The ether extract was washed in turn with saturated aqueous sodium bicarbonate and water, dried (MgSO$_4$) and the solvent evaporated to give the required oxime as an oil (3.8 g; 100%). Found: C,64.64, H,9.48, N,5.91. C$_{13}$H$_{23}$NO$_3$ requires C,64.70; H,9.61; N,5.80%.

(3) c-2-Butyl-c-4-(1,1-dimethylethoxycarbonylamino-r-1-cyclohexane carboxylic acid ethyl ester An aqueous solution of titanium trichloride (37 ml, 15% w/v; 36.5 mmole) was added dropwise at room temperature under nitrogen over 1.5 hours to a stirred solution of the above oxime (4.0 g; 16.57 mmole), ammonium acetate (16 g) and sodium cyanoborohydride (3.12 g; 49.7 mmole) in absolute ethanol (200 ml). After stirring for 14 hours the solvent was evaporated, water was added and the mixture was basified to pH8 with 1N sodium hydroxide. The product was stirred in air to oxidize unreacted reagent, and the suspension was then extracted with ethyl acetate. The organic extract was washed with saturated salt solution, dried (MgSO$_4$) and evaporated to give the crude amine as a clear gum (4.3 g). This product was dissolved in dry methylene chloride (80 ml) containing N-methylmorpholine (1.68 g; 16.6 mmole), di-tert-butyldicarbonate (7.23 g; 33.14 mmole) added and the solution allowed to stand at room temperature for 48 hours. The solvent was evaporated and the residue partitioned between diethyl ether and water. The ether extract was washed successively with 0.5N hydrochloric acid, water, saturated aqueous sodium bicarbonate and water. Drying over MgSO$_4$ and evaporation gave an oil (5.8 g) which was chromotographed on silica (600 g). Elution with diethyl ether:hexane (2:8) gave the required cis compound as an oil (2.72 g; 50%). Rf 0.38 (silica; ether:hexane 3:7). NMR: $\delta=2.66$ (HC—CO$_2$Et), $\delta=3.45$ (HC—NH—). Found: C,66.06; H,10.17; N,4.19. C$_{18}$H$_{33}$NO$_4$ requires C,66.02; H,10.16; N,4.28%. Continued elution then gave the more polar trans-isomer as an oil which solidified on standing (860 mg; 16%) Rf0.27. NMR: $\delta=2.45$ (HC—CO$_2$Et), $\delta=3.68$ (HC—NH—). Found: C,65.75; H, 10.13; N, 4.17. C$_{18}$H$_{33}$NO$_4$ requires C, 66.02; H, 10.16; N,4.28%.

(5) c-4-Amino-c-2-butyl-r-1-cyclohexane carboxylic acid ethyl ester hydrochloride An ice cold solution of the above cis-isomer (3.2 g; 9.8 mmole) in diethyl ether (100 ml) was saturated with HCl. After 3 hours the solvent was evaporated under a stream of nitrogen and the residue triturated with diethyl ether. Filtration gave a white solid (2.43 g; 94%) m.p. 249°-250° C. Found: C,59.16; H,9.83; N,5.38. C$_{13}$H$_{26}$ClNO$_2$ requires C,59.19; H,9.93; N,5.31%.

EXAMPLE 447 c-4-Amino-t-2-butyl-r-1-cyclohexane carboxylic acid ethyl ester hydrochloride (1) cis-7-Butyl-1,4-dioxaspiro[4,5]decane-8-carboxylic acid ethyl ester 2-Butyl-4-oxocyclohex-2-ene carboxylic acid ethyl ester (9.05 g; 40 mmole), ethyleneglycol (2.73 g; 44 mmole) and p-toluenesulphonic acid (100 mg) were refluxed in benzene (80 ml) using a Dean-Stark water trap. After 12 hours the mixture was cooled, diluted with diethyl ether and washed with saturated aqueous sodium bicarbonate followed by water. Drying over MgSO$_4$ and evaporation gave a liquid (10.80 g 100%) which was pure enough to use directly. Found: C,66.71; H,9.79, C$_{15}$H$_{26}$O$_4$ requires C,66.64; H,9.69%.

(2) trans-7-Butyl-1,4-dioxaspiro[4,5]decane-8-carboxylic acid ethyl ester

Potassium-tert-butoxide (1.9 g; 17 mmole) was added to a solution of the above ester (10.75 g; 39.7 mmole) in tert-butanol (90 ml), which had been dried over 3A seive, and the mixture was refluxed under nitrogen for 24 hours. The solution was then neutralised with 2N HCl and evaporated to a small volume under reduced pressure. The residue was taken up in diethyl ether washed with water, dried over MgSO$_4$ and evaporated to give a yellow liquid (10.0 g) which was chromatographed on silica (300 g). Elution with diethyl ether:hexane (2:8) gave the required trans-isomer as a clear liquid (8.80 g, 82%). Found: C,66.58; H,9.67. C$_{15}$H$_{26}$O$_4$ requires C,66.64; H,9.69%.

(3) trans-2-butyl-4-oxocyclohexanecarboxylic acid ethyl ester

The above ester (8.75 g; 32.4 mmole) in absolute ethanol (70 ml) was added to 1N sulphuric acid (50 ml) and the mixture was refluxed for 3 hours. Half the solvent was evaporated and the residual suspension was extracted with diethyl ether. The extract was washed with saturated aqueous sodium bicarbonate followed by water, dried (MgSO$_4$) and evaporated to give a clear liquid (6.85 g). Chromatography on silica (500 g) eluting with diethyl ether:hexane (2:8) gave the required ketone (6.05 g; 83%) as a clear liquid. Found: C,68.73; H,9.85. C$_{13}$H$_{22}$O$_3$ requires C,68.99; H,9.80%.

(4) trans-2-butyl-4-methoximinocyclohexane carboxylic acid ethyl ester

The above ketone (6.02 g, 26.6 mmole), methoxylamine hydrochloride (2.89 g; 34.6 mmole), sodium acetate (2.84 g; 34.6 mmole) were refluxed in absolute ethanol (100 ml) for 3 hours. After standing overnight at room temperature, most of the solvent was evaporated under reduced pressure and the residue was partitioned between diethyl ether and water. The ether extract was washed with saturated aqueous sodium bicarbonate followed by water, dried (MgSO$_4$) and evaporated to give a clear oil (6.77 g, 100%) which was pure enough to use directly. Found: C,65.78; H,9.71; N,5.43. C$_{14}$H$_{25}$NO$_3$ requires C,65.85; H,9.87; N,5.49%.

(5) t-2-Butyl-c-4-(1,1-dimethylethoxycarbonylamino)-1-r-cyclohexane carboxylic acid ethyl ester Trifluoroacetic acid (10.2 ml, 0.13 mmole) in dry tetrahydrofuran (20 ml) was added dropwise under nitrogen to a stirred suspension of sodium borohydride (5.0 g; 0.13 mmole) in dry tetrahydrofuran (120 ml). The temperature was kept between 10°–20° C. with ice cooling and after 15 minutes a solution of the above ester (6.75 g; 26.4 mmole) in tetrahydrofuran (20 ml) was added. The temperature rose to 33° C. and brief cooling was required to return the temperature to 20° C. After 4 hours water was carefully added, with ice cooling, followed by diethyl ether. The organic phase was washed with saturated salt solution, dried (MgSO$_4$) and evaporated to give crude amine (8.2 g). This product was dissolved in dry methylene chloride (100 ml) containing N-methyl morpholine (2.67 g, 26.4 mmole), di-tert-butyldicarbonate (11.52 g; 52.8 mmole) was added and the solution allowed to stand at room temperature for 48 hours. The solvent was evaporated and the residue partitioned between diethyl ether and water. The ether extract was washed successively with 0.5N hydrochloric acid, water, saturated aqueous sodium bicarbonate and water. Drying over MgSO$_4$ and evaporation gave an oil (8.86 g). Chromatography on silica eluting with diethyl ether:hexane (2:8) gave the required cis-isomer as an oil (1.61 g; 19%). Rf 0.35 (silica, ether:hexane 3:7). NMR: δ=2.13 (HC—CO$_2$Et), δ=3.88 (HC—NH—). Found: C,65.96; H,10.14; N,4.20. C$_{18}$H$_{33}$NO$_4$ requires C,66.02; H,10.16; N,4.28%. Continued elution then gave the more polar trans-isomer as a white solid (1.53 g; 18%). Recrystallisation from hexane gave a white solid m.p. 78°–9° C. Rf=0.3. NMR: δ=2.1 (HC—CO$_2$Et), δ=3.49 (HC—NH—). Found: C,66.08; H,10.24; N,4.17. C$_{18}$H$_{33}$NO$_4$ requires C,66.02; H,10.66; N,4.28%.

(6) c-4-Amino-t-2-butyl-r-1-cyclohexane carboxylic acid ethyl ester hydrochloride An ice cold solution of the above cis-isomer (1.58 g; 4.83 mmole) in diethyl ether (50 ml) was saturated with HCl. After 3 hours the solvent was evaporated under a stream of nitrogen and the residue was triturated with diethyl ether. Filtration gave the required amine salt as a white solid (1.17 g; 92%), m.p. 166°–7° C. Found: C,59.18; H,10.27; N,5.19. C$_{13}$H$_{26}$ClNO$_2$ requires C,59.19; H,9.93; N,5.31%.

EXAMPLE 448

3-[1-(c-4-Ethoxycarbonyl-c-3-butylcyclohexyl-r-1-carbamoyl)cyclopentyl]-2S-2-methoxyethoxymethyl)-propanoic acid 1,1-dimethylethyl ester, (diastereoisomers)

1-Ethyl-3-(3-dimethylamimopropyl)carbodiimide (575 mg; 3 mmole) was added to an ice cold stirred solution of 3-(1-carboxycyclopentyl)-2S-(2-methoxyethoxymethyl)propanoic acid 1,1-dimethyl ethyl ester (495 mg; 1.5 mmole), 1-hydroxybenzotriazole (202 mg; 1.5 mmole) N-methylmorpholine (455 mg; 4.5 mmole) and c-4-amino-c-2-butyl-r-1-cyclohexane carboxylic acid ethyl ester hydrochloride (396 mg; 1.5 mmole) in dry methylene chloride (15 ml). After half an hour the mixture was allowed to attain room temperature, and after five hours the solvent was evaporated under reduced pressure. The residue on standing for 20 hours was taken up in diethyl ether and washed successively with 0.5N hydrochloric acid, water, aqueous sodium bicarbonate solution and water. Drying over MgSO$_4$ and evaporation gave a gum (770 mg).

The crude product was chromatographed on silica and the two diastereoisomers were separated by elution with a mixture of diethyl ether:hexane:toluene (10:7:3).

Isomer I was obtained as a gum Rf=0.25 (silica, diethyl ether, hexane, toluene 10:7:3). Found: C,66.90; H,9.89; N,2.53. C$_{30}$H$_{53}$NO$_7$ requires C,66.76; H,9.90; N,2.60%.

Isomer II also obtained as a gum Rf=0.22. Found: C,66.93, H,9.90; N,2.41. C$_{30}$H$_{53}$NO$_7$ required as above.

EXAMPLE 449

3-[1-(c-4-Carboxy-c-3-butylcyclohexyl-r-1-carbamoyl)-cyclopentyl]-2S-(2-methoxyethoxymethyl)propanoic acid, (diastereoisomers)

Isomer A

Trifluoroacetic acid (5 ml) was added to an ice cold solution of isomer I from Example 3 above (350 mg) in dry methylene chloride. After standing at room temperature for 2.5 hours, the solvent was evaporated under reduced pressure and the residue dried azeotropically with toluene. The residue was dissolved in diethyl ether and washed twice with water, 5% aqueous ammonium carbonate being added dropwise to the first washing until the pH of the aqueous phase remained at about 5. The ether solution was then extracted with 1N sodium hydroxide (10 ml×2) and the combined aqueous extracts maintained at 65° C. for two days. The solution was acidified with concentrated hydrochloric acid and extracted with diethyl ether. The ether extract was washed with saturated salt solution, dried (MgSO$_4$) and evaporated to give the title product as a gummy foam (264 mg; 89%). [α]$_D^{25}$+22.1 (c=0.95, CH$_2$Cl$_2$). Found: C,62.93; H,8.87; N,2.90. C$_{24}$H$_{41}$NO$_5$ requires C,63.27; H,9.07; N,3.07%.

Isomer B

Prepared similarly from isomer II of Example 448 (330 mg), and was also obtained as a gummy foam (241 mg; 87%). [α]$_D^{25}$−21.9° (c=0.95, CH$_2$Cl$_2$). Found: C,63.58; H,9.18; N,2.89 C$_{24}$H$_{41}$NO$_7$ requires C,63.27; H,9.07; N,3.07%.

EXAMPLE 450

3-[1-(c-4-Ethoxycarbonyl-t-3-butyl-r-1-carbamoyl)cyclopentyl]-2S-(2-methoxyethoxymethyl)propanoic acid 1,1-dimethylethyl ester The procedure of Example 448 was followed but using the trans-isomer of the amine from Example 447. The diester product, a diastereoisomer mixture, was obtained as a gum (83%). Found: C,66.85; H,9.80; N,2.92. $C_{30}H_{53}NO_7$ requires C,66.76; H,9.90; N,2.60%.

EXAMPLE 451

3-[1-(c-4-Carboxy-t-3-butyl-r-1-carbamoyl)cyclopentyl]-2S-(2-methoxyethoxymethyl)propanoic acid The product of Example 450 was deprotected following the procedure of Example 449 to yield the title diacid product, a mixture of diastereoisomers, as a gum (99%). Found: C,63.28; H,9.15; N,3.07. $C_{24}H_{41}NO_7$ requires C,63.27; H,9.07; N,3.07%.

EXAMPLE 452

3-[1-(c-4-Ethoxycarbonyl-c-3-butylcyclohexyl-r-1-carbamoyl)cyclopentyl]-2-(2-methoxyethyl)propanoic acid benzyl ester Oxalyl chloride (1.55 g; 12.2 mmole) was added to a stirred solution of 3-(1-carboxycyclopentyl)-2-(2-methoxyethyl)propanoic acid benzyl ester (2.04 g; 6.1 mmole) in dry methylene chloride containing two drops of dimethylformide. After 2 hours the mixture was evaporated to dryness under reduced pressure. The residue was dissolved in dry methylene chloride (10 ml) and 5.7 ml of this solution was added to an ice cold stirred solution of c-4-amino-c-2-butyl-r-1-cyclohexane carboxylic acid ethyl ester hydrochloride (605 mg 2.3 mmole) and N-methylmorpholine (607 mg; 6 mmole) in dry methylene chloride (5 ml). After 0.5 hours the ice bath was removed and after a further 1 hour the solvent was evaporated under reduced pressure. The residue was suspended in water, extracted with diethyl ether and the organic extract washed successively with 2N hydrochloric acid, water, saturated aqueous sodium bicarbonate and water. Drying (MgSO$_4$) and evaporation gave an oil (1.64 g) which was chromatographed on silica. Elution with diethyl ether:hexane (1:1) gave the required diester as an oil. (1.07 g; 86%). Found: C,70.83; H,9.11; N,2.44. $C_{32}H_{49}NO_6$ requires C,70.69; H,9.08; N,2.58%.

EXAMPLE 453

3-[1-(c-4-Carboxy-c-3-butylcyclohexyl-r-1-carbamoyl)-cyclopentyl]-2-(2-methoxyethyl)propanoic acid The above diester from Example 452 (1.03 g; 1.89 mmole) was dissolved in a mixture of ethanol (25 ml) and water (10 ml) and hydrogenated over 10% palladium on carbon (200 mg) at room temperature and 50 psi (3.4 bar). After 1.5 hours the mixture was filtered through avicel and evaporated to dryness. The residual gum was dissolved in 1N sodium hydroxide and the solution was kept under nitrogen at 50° C. for two days. Further 1N sodium hydroxide (10 ml) was added and hydrolysis continued for 24 hours. On cooling the solution was acidified with 2N hydrochloric acid and extracted with diethyl ether. The extract was washed with water, dried (MgSO$_4$) and evaporated to give the title product as a white foam (660 mg; 82%). Found: C,63.80; H,9.34; N,3.39. $C_{23}H_{39}NO_6 \cdot 0.4H_2O$ requires C,63.83; H,9.27, N,3.27%.

EXAMPLE 454

The compounds were assessed for their ability to inhibit the neutral endopeptidase E.C.3.4.24.11 following the procedure described herein.

| Compound | IC$_{50}$ |
|---|---|
| Example$^{449}$ isomer A | $3.6 \times 10^{-9}$ |
| Example$^{449}$ isomer B | $5.6 \times 10^{-9}$ |
| Example 451 | $7.9 \times 10^{-9}$ |
| Example 453 | $8.0 \times 10^{-9}$ |
| Example 325 (2S isomer)* | $3.9 \times 10^{-8}$ |
| Example 217 | $5.0 \times 10^{-8}$ |

What is claimed is:

1. A compound of the formula:

or a pharmaceutically acceptable salt thereof, wherein:

A completes a 5- or 6-membered saturated or mono-unsaturated carbocyclic ring which is optionally fused to another 5- or 6-membered saturated carbocyclic ring or is optionally benzofused;

B is —(CH$_2$)$_m$— wherein m is an integer of from one to two;

R and R$^4$ are each independently hydrogen, C$_1$-C$_6$ alkyl or benzyl, or they represent a biolabile ester-forming group other than C$_1$-C$_6$ alkyl or benzyl;

R$^1$ is hydrogen or C$_1$-C$_4$ alkyl;

R$^2$ and R$^3$ are each independently hydrogen, hydroxy, C$_1$-C$_4$ alkyl or C$_1$-C$_4$ alkoxy; and R$^5$ is C$_1$-C$_6$ alkyl, C$_2$-C$_6$ alkenyl, C$_2$-C$_6$ alkynyl, C$_3$-C$_7$ cycloalkyl, C$_3$-C$_7$ cycloalkenyl, aryl(C$_2$-C$_6$ alkynyl), —NR$^6$R$^7$, —NR$^8$COR$^9$, —NR$^8$SO$_2$R$^9$, tetrahydrofuranyl or homodioxanyl; or C$_1$-C$_6$ alkyl substituted by halogen, hydroxy, C$_1$-C$_6$ alkoxy, C$_2$-C$_6$ hydroxyalkoxy, C$_1$-C$_6$ alkoxy(C$_1$-C$_6$ alkoxy), C$_3$-C$_7$ cycloalkyl, C$_3$-C$_7$ cycloalkenyl, aryl, aryloxy, aryloxy(C$_1$-C$_6$ alkoxy), heterocyclyl, heterocyclyloxy, —NR$^6$R$^7$, —NR$^8$COR$^9$, —NR$^8$SO$_2$R$^9$, —CONR$^6$R$^7$, —SH, —S(O)$_p$R$^{10}$, —COR$^{11}$ or —COOR$^{12}$; wherein R$^6$ and R$^7$ are each independently hydrogen, C$_1$-C$_4$ alkyl, aryl, aryl(C$_1$-C$_4$ alkyl), C$_2$-C$_6$ alkoxyalkyl, heterocyclyl or C$_3$-C$_7$ cycloalkyl optionally substituted by hydroxy or C$_1$-C$_4$ alkoxy;

R$^6$ and R$^7$, when taken together with the nitrogen atom to which they are attached, form a pyrrolidinyl, piperidino, morpholino, piperazinyl or N-(C$_1$-C$_4$ alkyl)piperazinyl group;

R$^8$ is hydrogen or C$_1$-C$_4$ alkyl;

R$^9$ is C$_1$-C$_4$ alkyl, C$_1$-C$_4$ alkoxy, trifluoromethyl, aryl, aryl(C$_1$-C$_4$ alkyl), aryl(C$_1$-C$_4$ alkoxy), heterocyclyl or —NR$^6$R$^7$;

R$^{10}$ is C$_1$-C$_4$ alkyl, aryl, heterocyclyl or —NR$^6$R$^7$;

R$^{11}$ is C$_1$-C$_4$ alkyl, C$_3$-C$_7$ cycloalkyl, aryl or heterocyclyl;

R$^{12}$ is hydrogen or C$_1$-C$_4$ alkyl; and p is zero, one or two;

said biolabile ester-forming group other than $C_1-C_6$ alkyl or benzyl in the definition of R and $R^4$ being selected from $C_1-C_8$ alkanoyloxy($C_1-C_8$ alkyl), and the $C_1-C_8$ alkyl and $C_3-C_7$ cycloalkyl-substituted derivatives thereof and the aryl-substituted derivatives thereof, aroyloxy($C_1-C_8$ alkyl), aryl, aryl($C_1-C_8$ alkyl) and halo($C_1-C_8$ alkyl), wherein said aryl groups are phenyl, naphthyl or indanyl with said aryl groups being optionally substituted with halogen, $C_1-C_4$ alkyl or $C_1-C_4$ alkoxy groups;

said aryl groups in the definition of $R^5$, $R^6$, $R^9$, $R^{10}$ and $R^{11}$ having up to ten carbon atoms the nuclear ring, with said groups being optionally substituted with halogen, hydroxy, cyano, trifluoromethyl, $C_1-C_4$ alkyl, $C_1-C_4$ alkoxy, carbamoyl, amino, mono- or di($C_1-C_4$ alkyl)amino or $C_1-C_4$ alkanoylamino groups; and said heterocyclyl groups in the definition of $R^5$ being pyridyl, pyrazinyl, pyrimidinyl, pyridazinyl, pyrrolyl, imidazolyl, pyrazolyl, triazolyl, tetrazolyl, furanyl, tetrahydrofuranyl, tetrahydropyranyl, dioxanyl, thienyl, oxazolyl, isoxazolyl, thiazolyl, indolyl, isoindolinyl, quinolyl, quinoxalinyl, quinazolinyl and benzimidazolinyl, with said groups being optionally substituted with halogen, hydroxy, oxo, $C_1-C_4$ alkyl, benzyl, carbamoyl, amino, mono- or di($C_1-C_4$ alkyl)amino or $C_1-C_4$ alkanoylamino groups.

2. A compound as claimed in claim 1 wherein A is $-(CH_2)_n-$ and n is four or five, and each of R and $R^4$ is independently hydrogen, $C_1-C_6$ alkyl or benzyl.

3. A compound as claimed in claim 1 wherein R and $R^4$ are each hydrogen.

4. A compound as claimed in claim 1 wherein R and $R^4$ are each hydrogen, $C_1-C_6$ alkyl, benzyl or a biolabile ester-forming group other than $C_1-C_6$ alkyl or benzyl, with the proviso that at least one of R and $R^4$ is always other then hydrogen.

5. A compound as claimed in claim 4 wherein one of R and $R^4$ is hydrogen and the other is ethyl or benzyl.

6. A compound as claimed in claim 4 wherein said biolabile ester-forming group is 1-(2,2-diethylbutyryloxy)ethyl, 2-ethylpropionyloxymethyl, 1-(2-ethylpropionyloxy)ethyl, 1-(2,4-dimethylbenzoyloxy)ethyl, α-benzoyloxybenzyl, 1-(benzoyloxy)ethyl, 2-methyl-1-propionyloxy-1-propyl, 2,4,6-trimethylbenzoyloxymethyl, 1-(2,4,6-trimethylbenzoyloxy)ethyl, pivaloyloxymethyl, phenylethyl, phenylpropyl, 2,2,2-trifluoroethyl, 1- or 2-naphthyl, 2,4-dimethylphenyl, 4-tert.-butylphenyl or 5-indanyl.

7. A compound as claimed in claim 6 wherein said biolabile ester-forming group is 5-indanyl.

8. A compound as claimed in claim 1 wherein $R^5$ is $C_2-C_4$ alkyl, $C_2-C_4$ alkenyl, $C_2-C_5$ alkynyl, $C_5-C_6$ cycloalkyl, $C_5-C_6$ cycloalkenyl, $C_1-C_4$ alkylsulphonamido or tetrahydrofuranyl; or $C_1-C_3$ alkyl substituted by $C_1-C_3$ alkoxy, $C_1-C_6$ alkoxy($C_2-C_4$ alkoxy), $C_3-C_6$ cycloalkyl, 4-pyridyl, 2-imidazolyl, $C_2-C_4$ alkanoyl, $C_2-C_4$ alkoxycarbonylamino, $C_1-C_4$ alkylsulphonyl, $C_1-C_4$ alkylsulphonamido, benzenesulphonamido heteroarylsulphonamido or benzoylamino.

9. A compound as claimed in claim 1 wherein A is $(CH_2)_7$, B is $-(CH_2)_2-$ and $R^1$ is hydrogen, said compound being of the formula:

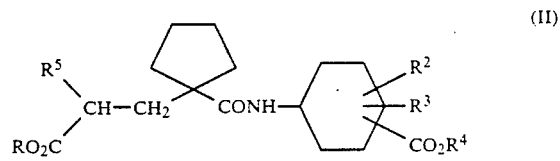

(II)

wherein R, $R^2$, $R^3$, $R^4$ and $R^5$ are each as previously defined in claim 1.

10. A compound as claimed in claim 9 wherein R, $R^2$, $R^3$ and $R^4$ are each hydrogen.

11. A compound as claimed in claim 10 wherein $R^4$ in $COOR^4$ is hydrogen and said carboxy group is attached at the 3- or 4-positions of the cyclohexane ring and has cis-stereochemistry relative to the amide group at the 1-position of the molecule.

12. A compound as claimed in claim 9 wherein R and $R^2$ are each hydrogen, $R^3$ is hydrogen, methyl or ethyl, and $R^4$ is ethyl.

13. A compound as claimed in claim 12 wherein $R^4$ in $-COOR^4$ is ethyl and said ethoxycarbonyl group is attached at the 3-position of the cyclohexane ring and has cis-stereochemistry relative to the amide group at the 1-position of the molecule.

14. A compound as claimed in claim 11 of the formula (II) wherein said carboxy group is attached at the 4-position of the cyclohexane ring and has cis-stereochemistry relative to the amide group at the 1-position of the molecule, $R^3$ is hydrogen and $R^5$ is n-propyl, 2-butynyl, 2-cyclohexenyl, n-propylsulfonamido, tetrahydrofuranyl, methoxyethyl, 2-methoxyethoxymethyl, 4-pyridylmethyl, 2-imidazolylmethyl, acetonyl, 1-methoxycarbonylaminoethyl, ethylsulphonylmethyl or benzenesulphonamidomethyl.

15. A compound as claimed in claim 14 wherein $R^5$ is n-propyl, 2-butynyl, n-propylsulphonamido, 3-tetrahydrofuranyl, 2-methoxyethyl or 2-methoxyethoxymethyl.

16. A compound as claimed in 15 wherein $R^5$ is 2-methoxyethoxymethyl, which is 3-{1-[(cis-4-carboxycyclohexyl)carbamoyl]cyclopentyl}-2-(2-methoxyethoxymethyl)propanoic acid.

17. A compound as claimed in claim 15 wherein $R^5$ is 2-methoxyethyl, which is 3-{1-[(cis-4-carboxycyclohexyl)carbamoyl]cyclopentyl}-2-(2-methoxyethyl)propionic acid.

18. A compound as claimed in claim 11 of the formula (II) wherein said carboxy group is attached at the 3-position of the cyclohexane ring and has cis-stereochemistry relative to the amide group at the 1-position of the molecule, $R^3$ is hydrogen and $R^5$ is n-propyl, 2-propenyl, 2-butenyl, 2-butynyl, cyclopentyl, cyclohexyl, 2-cyclohexenyl, n-propylsulphonamido, tetrahydrofuranyl, 2-methoxyethoxymethyl, cyclopropylmethyl, 4-pyridylmethyl, benzensulphonamidomethyl or benzoylaminomethyl.

19. A compound as claimed in claim 18 wherein $R^5$ is n-propyl, 2-butynyl, n-propylsulphonamido or 2-methoxyethoxymethyl.

20. A compound as claimed in claim 13 of the formula (II) wherein $R^3$ is hydrogen and $R^5$ is n-propyl, 2-propenyl, 2-butynyl, cyclopentyl, cyclohexyl, cyclohexenyl, tetrahydrofuranyl, 2-methoxyethoxymethyl, cyclopropylmethyl, 4-pyridylmethyl, n-propylsulphonamido, benzenesulphonamidomethyl or benzoylaminomethyl.

21. A compound as claimed in claim 20 wherein $R^5$ is n-propyl 2-butynyl, n-propylsulphonamido or 2-methoxyethoxymethyl.

22. A compound as claimed in claim 9 of the formula (II) wherein R and $R^4$ are each hydrogen or 5-indanyl, with the proviso that at least one of R and $R^4$ is other than hydrogen.

23. A compound as claimed in claim 22 wherein $R^2$ and $R^3$ are each hydrogen, and said —$COOR^4$ group is attached at the 4-position of the cyclohexane ring and has cis-stereochemistry relative to the amide group at the 1-position of the molecule.

24. A compound as claimed in claim 23 wherein R is 5-indanyl, $R^4$ is hydrogen and $R^5$ is 2-methoxyethoxymethyl, which is 3-{1-[(cis-4-carboxycyclohexyl)carbamoyl]cyclopentyl}-2-(2-methoxyethoxymethyl)-propanoic acid 5-indanyl ester.

25. A compound as claimed in claim 9 wherein R, $R^3$ and $R^4$ are each hydrogen, and $R^2$ is butyl or $C_3$–$C_4$ alkoxy.

26. A compound as claimed in claim 25 wherein $R^4$ in —$COOR^4$ is hydrogen and said carboxy group is attached at the 4-position of the cyclohexane ring and has cis-stereochemistry relative to the amide group at the 1-position of the molecule.

27. A compound as claimed in claim 26 of the formula (II) wherein $R^2$ is butyl and $R^5$ is n-propyl, 2-methoxyethoxymethyl, 2-methoxyethyl, methoxymethyl or allyl.

28. A compound as claimed in claimed 27 wherein $R^2$ is n-butyl attached at the 3-position of the cyclohexane ring and $R^5$ is 2-methoxyethoxymethyl or 2-methoxyethyl.

29. A compound as claimed in claim 28 wherein $R^2$ is cis-n-butyl and $R^5$ is 2-methoxyethoxymethyl.

30. A compound as claimed in claim 28 wherein $R^2$ is trans-n-butyl and $R^5$ is 2-methoxyethoxymethyl.

31. A compound as claimed in claim 28 wherein $R^2$ is cis-n-butyl and $R^5$ is 2-methoxyethyl, which is 3-{1-[(cis-4-carboxy-cis-3-n-butylcyclohexyl)-rel-1-carbamoyl]cyclopentyl}-2-(2-methoxyethyl)propionic acid.

32. A compound as claimed in claim 9 wherein $R^2$ and $R^3$ are each hydrogen and $R^5$ is 2-methoxyethoxymethyl, said compound being an (S)-enantiomer of a cis-isomeric acid of the formula:

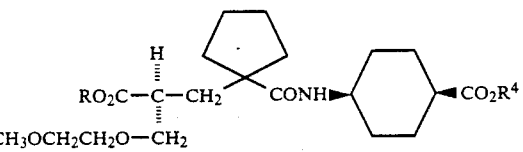

wherein each of R and $R^4$ is hydrogen, or one of R and $R^4$ is hydrogen and the other is a biolabile ester-forming group, said enantiomeric compound being substantially free of the R-enantiomer.

33. A compound as claimed in claim 32 wherein said biolabile ester-forming group is benzyl or 5-indanyl.

34. A compound as claimed in claim 32 wherein R and $R^4$ are each hydrogen, which is (S)-cis-4-{1-[2-carboxy-3-(2-methoxyethoxy)propyl]-1-cyclopentanecarboxamido}-1-cyclohexanecarboxylic acid.

35. A compound as claimed in claim 33 wherein R is 5-indanyl and $R^4$ is hydrogen, which is (S)-cis-4-{1-[2-(5-indanyloxycarbonyl)-3-(2-methoxyethoxy)propyl]-1-cyclopentanecarboxamido}-1-cyclohexanecarboxylic acid.

36. A pharmaceutical composition suitable for oral or parenteral administration comprising a pharmaceutically acceptable inert carrier or diluent and an effective antihypertensive/diuretic amount of a compound as claimed in claim 1.

37. The composition according to claim 36 wherein the compound is (S)-cis-4-{1-[2-(5-indanyloxycarbonyl)-3-(2-methoxyethoxy)propyl]-1-cyclopentanecarboxamido}-1-cyclohexanecarboxylic acid.

38. The composition according to claim 36 wherein the compound is (S)-cis-4-{1-[2-carboxy-3-(2-methoxyethoxy)propyl]-1-cyclopentanecarboxamido}-1-cyclohexanecarboxylic acid.

* * * * *